(12) United States Patent
Biere-Citron et al.

(10) Patent No.: US 8,414,893 B2
(45) Date of Patent: Apr. 9, 2013

(54) ANTI-AMYLOID ANTIBODIES AND USES THEREOF

(75) Inventors: Anja Leona Biere-Citron, Indianapolis, IN (US); Frederick W. Jacobsen, Newbury Park, CA (US); Stephen J. Wood, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/809,563

(22) PCT Filed: Dec. 19, 2008

(86) PCT No.: PCT/US2008/013881
§ 371 (c)(1),
(2), (4) Date: Jun. 18, 2010

(87) PCT Pub. No.: WO2009/085200
PCT Pub. Date: Jul. 9, 2009

(65) Prior Publication Data
US 2011/0044986 A1    Feb. 24, 2011

Related U.S. Application Data

(60) Provisional application No. 61/016,167, filed on Dec. 21, 2007.

(51) Int. Cl.
*A61K 39/395* (2006.01)
*C07K 16/18* (2006.01)
*C12P 21/08* (2006.01)
*C07H 21/04* (2006.01)
*C12N 15/13* (2006.01)
*C12N 5/07* (2010.01)

(52) U.S. Cl. ........... 424/142.1; 424/139.1; 424/130.1; 424/135.1; 50/388.15; 50/387.9; 50/387.3; 50/387.1; 536/23.53; 435/320.1; 435/331; 435/69.6

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. |
| 4,301,144 A | 11/1981 | Iwashita et al. |
| RE30,985 E | 6/1982 | Cartaya |
| 4,495,285 A | 1/1985 | Shimizu et al. |
| 4,496,689 A | 1/1985 | Mitra |
| 4,560,655 A | 12/1985 | Baker |
| 4,609,564 A | 9/1986 | Pinkhasov |
| 4,640,835 A | 2/1987 | Shimizu et al. |
| 4,657,866 A | 4/1987 | Kumar |
| 4,666,829 A | 5/1987 | Glenner et al. |
| 4,670,417 A | 6/1987 | Iwasaki et al. |
| 4,766,106 A | 8/1988 | Katre et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,892,538 A | 1/1990 | Aebischer et al. |
| 4,927,762 A | 5/1990 | Darfler |
| 5,122,469 A | 6/1992 | Mather et al. |
| 5,200,339 A | 4/1993 | Abraham |
| 5,229,275 A | 7/1993 | Goroff |
| 5,283,187 A | 2/1994 | Aebischer et al. |
| 5,455,169 A | 10/1995 | Mullan |
| 5,530,101 A | 6/1996 | Queen et al. |
| 5,562,903 A | 10/1996 | Co et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,591,828 A | 1/1997 | Bosslet et al. |
| 5,693,762 A | 12/1997 | Queen et al. |
| 5,744,346 A | 4/1998 | Chrysler et al. |
| 5,766,886 A | 6/1998 | Studnicka et al. |
| 5,795,963 A | 8/1998 | Mullan |
| 5,877,293 A | 3/1999 | Adair et al. |
| 5,939,598 A | 8/1999 | Kucherlapati et al. |
| 5,942,400 A | 8/1999 | Anderson et al. |
| 6,054,287 A | 4/2000 | Gao et al. |
| 6,171,586 B1 | 1/2001 | Lam et al. |
| 6,221,645 B1 | 4/2001 | Chrysler et al. |
| 6,245,884 B1 | 6/2001 | Hook |
| 6,313,268 B1 | 11/2001 | Hook |
| 6,331,408 B1 | 12/2001 | Zaczek et al. |
| 6,489,123 B2 | 12/2002 | Osbourn et al. |
| 6,545,127 B1 | 4/2003 | Tang et al. |
| 6,583,268 B2 | 6/2003 | Lin |
| 6,737,038 B1 | 5/2004 | Zaczek et al. |
| 6,743,427 B1 | 6/2004 | Schenk |
| 6,787,637 B1 | 9/2004 | Schenk |
| 6,790,610 B2 | 9/2004 | Gurney et al. |
| 6,797,487 B2 | 9/2004 | Gurney et al. |
| 6,818,448 B2 | 11/2004 | Mullan |
| 6,852,482 B1 | 2/2005 | Chrysler et al. |
| 6,864,290 B2 | 3/2005 | Schostarez et al. |
| 7,033,812 B2 | 4/2006 | Zhong et al. |
| 7,041,870 B2 | 5/2006 | Tomizuka et al. |
| 7,087,399 B1 | 8/2006 | Zhong et al. |

(Continued)

FOREIGN PATENT DOCUMENTS

EP    0315456 A2    5/1989
EP    061307 A2    8/1994

(Continued)

OTHER PUBLICATIONS

U.S. Appl. No. 60/474,654, filed May 30, 2003, Basi, Guriq.

(Continued)

*Primary Examiner* — Elizabeth C Kemmerer
*Assistant Examiner* — Kimberly A Ballard
(74) *Attorney, Agent, or Firm* — Nisan A. Steinberg

(57) ABSTRACT

Compositions for treating neurodegenerative or amyloidogenic disorders such as Alzheimer's disease (AD) are provided. More particularly, anti-amyloid-beta antibodies, compositions containing such antibodies, corresponding nucleic acids, vectors and host cells, and methods of making such antibodies are provided.

20 Claims, 3 Drawing Sheets

U.S. PATENT DOCUMENTS

| | | | |
|---|---|---|---|
| 7,119,166 B2 | 10/2006 | Lin | |
| 7,153,491 B2 | 12/2006 | Zaczek et al. | |
| 7,169,901 B2 | 1/2007 | Baca et al. | |
| 7,179,892 B2 | 2/2007 | Basi et al. | |
| 7,183,390 B2 | 2/2007 | Vasquez et al. | |
| 7,241,873 B2 | 7/2007 | Uede et al. | |
| 7,244,708 B2 | 7/2007 | Tang et al. | |
| 7,256,273 B2 | 8/2007 | Basi et al. | |
| 7,320,790 B2 | 1/2008 | Hinton et al. | |
| 7,335,632 B2 | 2/2008 | Ghosh et al. | |
| 7,351,803 B2 | 4/2008 | Johnson et al. | |
| 7,538,258 B2 | 5/2009 | Mullan | |
| 7,732,399 B2 | 6/2010 | Goldenberg et al. | |
| 2002/0055459 A1 | 5/2002 | Chopra et al. | |
| 2002/0086847 A1 | 7/2002 | Chain | |
| 2002/0115600 A1 | 8/2002 | Koelsch et al. | |
| 2002/0157122 A1 | 10/2002 | Wong et al. | |
| 2003/0044772 A1 | 3/2003 | Watkins et al. | |
| 2003/0073655 A1 | 4/2003 | Chain | |
| 2003/0082191 A1 | 5/2003 | Poduslo et al. | |
| 2003/0082735 A1 | 5/2003 | McGrew et al. | |
| 2003/0092125 A1 | 5/2003 | Davis et al. | |
| 2003/0113316 A1 | 6/2003 | Kaisheva et al. | |
| 2004/0043418 A1 | 3/2004 | Holtzman et al. | |
| 2004/0132680 A1 | 7/2004 | Wong et al. | |
| 2004/0167075 A1 | 8/2004 | Tang et al. | |
| 2004/0171815 A1 | 9/2004 | Schenk et al. | |
| 2004/0171816 A1 | 9/2004 | Schenk et al. | |
| 2004/0220079 A1 | 11/2004 | Koelsch et al. | |
| 2004/0248232 A1 | 12/2004 | Hook | |
| 2004/0248766 A1 | 12/2004 | LeBlanc | |
| 2005/0019255 A1 | 1/2005 | Zaczek et al. | |
| 2006/0034848 A1 | 2/2006 | Kinoshita et al. | |
| 2006/0182684 A1 | 8/2006 | Beliveau | |
| 2006/0189515 A1 | 8/2006 | Beliveau et al. | |
| 2006/0198851 A1 | 9/2006 | Basi et al. | |
| 2006/0228349 A1 | 10/2006 | Acton et al. | |
| 2007/0099185 A1 | 5/2007 | Hagen et al. | |
| 2008/0021196 A1 | 1/2008 | Tang et al. | |
| 2008/0292639 A1 | 11/2008 | Shen et al. | |

FOREIGN PATENT DOCUMENTS

| | | | |
|---|---|---|---|
| EP | 1431310 A1 | 6/2004 | |
| EP | 1129355 B1 | 7/2005 | |
| EP | 1327143 B1 | 2/2007 | |
| EP | 1255769 B1 | 5/2007 | |
| WO | WO-87/00195 A1 | 1/1987 | |
| WO | WO-87/05330 A1 | 9/1987 | |
| WO | WO-90/03430 A1 | 4/1990 | |
| WO | WO-90/14363 A1 | 5/1990 | |
| WO | WO-91/00741 A1 | 1/1991 | |
| WO | WO-91/17271 A1 | 1/1991 | |
| WO | WO-92/01047 A1 | 1/1992 | |
| WO | WO-92/11018 A1 | 7/1992 | |
| WO | WO-93/11161 A1 | 6/1993 | |
| WO | WO-93/25673 A1 | 12/1993 | |
| WO | WO-94/02602 A1 | 2/1994 | |
| WO | WO-96/25435 A1 | 8/1996 | |
| WO | WO-96/32478 A1 | 10/1996 | |
| WO | WO-96/33735 A1 | 10/1996 | |
| WO | WO-96/34096 A1 | 10/1996 | |
| WO | WO-96/04885 A3 | 12/1996 | |
| WO | WO-96/40885 A2 | 12/1996 | |
| WO | WO-97/34631 A1 | 9/1997 | |
| WO | WO-98/24893 A2 | 6/1998 | |
| WO | WO-98/44955 A1 | 10/1998 | |
| WO | WO-99/60024 C2 | 1/1999 | |
| WO | WO-99/27944 A1 | 6/1999 | |
| WO | WO-99/27944 C2 | 6/1999 | |
| WO | WO-00/17369 A2 | 3/2000 | |
| WO | WO-00/23576 A2 | 4/2000 | |
| WO | WO-00/24782 A2 | 5/2000 | |
| WO | WO-00/47618 C2 | 8/2000 | |
| WO | WO-01/23533 A2 | 4/2001 | |
| WO | WO-02/25276 A1 | 3/2002 | |
| WO | WO-02/46237 A2 | 6/2002 | |
| WO | WO-02/088307 A2 | 11/2002 | |
| WO | WO-03/016467 A2 | 2/2003 | |
| WO | WO-03/020212 A2 | 3/2003 | |
| WO | WO-03/027151 A1 | 4/2003 | |
| WO | WO-03/070760 A2 | 8/2003 | |
| WO | WO-2004/032868 A2 | 4/2004 | |
| WO | WO-2004/060403 A2 | 7/2004 | |
| WO | WO-2004/065423 A2 | 8/2004 | |
| WO | WO-2004/080419 A2 | 9/2004 | |
| WO | WO-2004/084830 A2 | 10/2004 | |
| WO | WO-2004/108895 A2 | 12/2004 | |
| WO | WO-2004/108895 A3 | 12/2004 | |
| WO | WO-2004/110369 A2 | 12/2004 | |
| WO | WO-2006/055178 A2 | 5/2006 | |
| WO | WO-2006/066089 A1 | 6/2006 | |
| WO | WO-2006/066171 A1 | 6/2006 | |
| WO | WO-2006/081171 A1 | 8/2006 | |
| WO | WO 2006104677 A2 * | 10/2006 | |
| WO | WO-2007/009229 A1 | 1/2007 | |
| WO | WO-2007/113172 A2 | 10/2007 | |
| WO | WO-2007/113172 A3 | 10/2007 | |
| WO | WO-2008/046228 A1 | 4/2008 | |
| WO | WO 2009040134 A1 * | 4/2009 | |

OTHER PUBLICATIONS

U.S. Appl. No. 60/621,776, filed Oct. 25, 2004, Lambert et al.
U.S. Appl. No. 60/636,776, filed Dec. 15, 2004, Basi et al.
U.S. Appl. No. 60/646,658, filed Jan. 24, 2005, Shen et al.
U.S. Appl. No. 60/652,538, filed Feb. 14, 2005, Shughrue et al.
Anderson, Human gene therapy, Nature, 392:25-30, 1998.
Aplin et al., Preparation, properties, and applications of carbohydrate conjugates of proteins and lipids, CRC Crit. Rev. Biochem., 10:259-306:1981.
Ballas et al., Liposomes bearing a quaternary ammonium detergent as an efficient vehicle for functional transfer of TMV-RNA into plant protoplasts, BBA, 939:3-18, 1988.
Banks, William A., Are the Extracelluar Pathways A Conduit for the Delivery of Therapeutics to the Brain?, Current Pharmaceutical Design, 10: 1365-1370, 2004.
Bard et al., Peripherally administered antibodies against amyloid beta-peptide enter the central nervous system and reduce pathology in a mouse model of Alzheimer disease, Nat. Med., 6:916-919, 2000.
Barnes et al., Methods for growth of cultured cells in serum-free medium, Anal. Biochem., 102:255-270, 1980.
Begley, Delivery of therapeutic agents to the central nervous system; the problems and the possibilities, Pharmacol. Ther, 104:29-45, 2004.
Behr et al., Efficient gene transfer into mammalian primary endocrine cells with lipopolyamine-coated DNA, PNAS USA, 86;6982-6986, 1989.
Behr, DNA strongly binds to micelles and vesicles containing lipopolyamines or lipointercalants, Tetrahedron Lett., 27:5861-5864, 1986.
Behr, Gene transfer with synthetic cationic amphiphiles: prospects for gene therapy, Bioconj. Chem., 5:382-389, 1994.
Better et al., *Escherichia coil* secretion of an active chimeric antibody fragment, Science, 240:1041-1043, 1988.
Bhatnagar et al., Structure-activity relationships of novel hematoregulatory peptides, J. Med. Chem, 39:3814-3819, 1996.
Boulianne et al., Production of functional chimaeric mouse/human antibody, Nature, 312:643-646, 1984.
Burton et al., Human antibodies from combinatorial libraries, Adv. Immunol., 57:191-280, 1994.
Caron et al., Engineered humanized dimeric forms of IgG are more effective antibodies, J. Exp. Med., 176:1191-1195, 1992.
Carpenter et al., Interactions of stabilizing additives with proteins during freeze-thawing and freeze-drying, Dev. Biol. Standardization, 74:225-239, 1991.
Carter et al., High level *Escherichia coil* expression and production of a bivalent humanized antibody fragment, Biotechnology, 10:163-167, 1992.
Cassett et al., A peptide mimetic of an anti-CD4 monoclonal antibody by rational design, Biochemical and Biophysicai Research Communciations, vol. 307, pp. 198-205, 2003.

Caton et al., Influenza virus hemagglutinin-specific antibodies isolated from a combinatorial expression library are closely related to the immune response of the donor, PNAS USA, 87:6450-6454, 1990.

Chen, Formulation concern of protein drugs, Drug Dev. Indust. Pharm., 18:1311-1354, 1992.

Cherny et al,, Treatment with a copper-zinc chelator markedly and rapidly inhibits beta-amyloid accumulation in Alzheimer's disease transgenic mice, Neuron, 30:665-666, 2001.

Chothia et al., Canonical structures for the hypervariable regions of immunoglobulins, J. Mol. Biol., 196:901-917, 1987.

Chung et al., Uptake, degradation, and release of fibrillar and soluble forms of Alzheimer's amyloid beta-peptide by microglial cells, J. Biol. Chem., 274:32301-32308, 1999.

Clackson et al., In vitro selection from protein and peptide libraries, Trends Biotechnol., 12:173-184, 1984.

Clackson et al., Making antibody fragments using phage display libraries, Nature, 352:624-628, 1991.

Co et al., A humanized antibody specific for the platelet integrin gpIIb/IIIa, J. Immunol., 152:2968-2976, 1994.

Cunningham et al., High-resolution epitope mapping of hGH-receptor interactions by alanine-scanning mutagenesis, Science, 244:1081-1085, 1989.

Cuthbertson et al., Design of low molecular weight hematoregulatory agents from the structure-activity relationship of a dimeric pentapeptide, J. Med. Chem., 40:2876-2882, 1997.

Davies et al., Affinity improvement of single antibody VH domains: residues in all three hypervariable regions affect antigen binding, Immunotechnology, 2:169-179, 1996.

Demattos et al., Peripheral anti-A beta antibody alters CNS and plasma A beta clearance and decreases brain A beta burden in a mouse model of Alzheimer's disease, PNAS USA, 93:8850-3855, 2001.

Doody, Therapeutic standards in Alzheimer disease, Alzheimer Dis. Assoc. Disord., 13:S20-S26, 1999.

Edge et al., Deglycosylation of glycoproteins by trifluoromethanesulfonic acid, Anal. Biochem., 118:131-137, 1981.

Evan et al., Isolation of monoclonal antibodies specific for human c-myc proto-oncogene product, Mol. Cell. Biol., 5:3610-3616, 1985.

Fassbender et al., Simvastatin strongly reduces levels of Alzheimer's disease β-amyloid peptides Aβ42 and Aβ40 in vitro and in vivo, PNAS, 98:5856-5861, 2000.

Felgner et al., Lipofection: a highly efficient, lipid-mediated DNA-transfection procedure, PNAS USA, 84:7413-7417, 1987.

Fermér et al., Specificity rescue and affinity maturation of a low-affinity IgM antibody against pro-gastrin-releasing peptide using phage display and DNA shuffline, Tumor Biol., 25:7-13, 2004.

Field et al., Purification of a RAS-responsive adenylyl cyclase complex from *Saccharomyces cerevisiae* by use of an epitope addition method, Mol. Cell. Biol., 3:2159-2165, 1988.

Friedmann, Progress toward human gene therapy, Science, 244:1275-1281, 1989.

Gervais et al., A low molecular weight GAG mimetic compound reduces brain amyloid burden in hAPP transgenic mice, 7th International Geneva/Springfield Symposium on Advances in Alzheimer Therapy, 2002.

Golde et al., Cholesterol modulation as an emerging strategy for the treatment of Alzheimer's disease, Drug Discov. Today, 6:1049-1055, 2001.

Golde, Todd E., Alzheimer disease therapy: Can the amyloid cascade be halted?, The Journal of Clinical Investigation, 111 (1): 11-18, 2003.

Graham et al., Characteristics of a human cell line transformed by DNA from human adenovirus type 5, J. Gen. Virol., 36:59-74, 1977.

Guss et al., EMBO J., 5:1567-1575, 1986.

Ham et al., Media and growth requirements, Methods Enzymol., 58:44-93, 1979.

Hardy et al., Amyloid deposition as the central event in the aetiology of Alzheimer's disease, Trends Pharmacol. Sci., 23:333-388, 1991.

Hollinger et al., "Diabodies": small bivalent and bispecific antibody fragments, PNAS USA, 90:6444-6448, 1993.

Holt et al., Domain antibodies: proteins for therapy, Trends Biotechnol., 21:484-490, 2003.

Hoogenboom et al., By-passing immunization: human antibodies from synthetic repertoires of germline VH gene segments rearranged in vitro, J. Mol. Biol., 227:381-388, 1991.

Ito et al., Synthetic cationic anlphiphiles for liposome-mediated DNA transfection, Biochem. Int., 22:235-241, 1990.

Jermutus et al., Tailoring in vitro evolution for protein affinity or stability, PNAS USA, 98:75-80, 2001.

Jespers et al., Guiding the selection of hurnan antibodies from phage display repertoires to a single epitope of an antigen, Biotechnology, 12:899-903, 1994.

Jick et al., Statins and the risk of dementia, Lancet, 356:1627-1631, 2000.

Joachim et al., The seminal role of β-amyloid in the pathogenesis of Alzheimer disease, Alzheimer Dis. Assoc. Disord., 6:7-34, 1992.

Jones et al., Replacing the complementarity-determining regions in a human antibody with those from a mouse, Nature, 321:522-525, 1986.

Kettleborough et al., Humanization of a mouse monoclonal antibody by CDR-grafting: the importance of framework residues on loop conformation, Protein Eng., 4:773-783, 1991.

Kilpatrick et al., Rapid development of affinity matured monoclonal antibodies using RIMMS, Hybridoma, 16:381-389, 1997.

Kirschner et al., Synthetic peptide homologous to beta protein from Alzheimer disease forms amyloid-like fibrils in vitro, PNAS USA, 84:6953-6957, 1987.

Köhler et al., Continuous cultures of fused cells secreting antibody of predefined specificity, Nature, 256:495-497, 1975.

Kowall et al., An in vivo model for the neurodegenerative effects of Beta amyloid and by substance P, Proc. Natl. Acad, Sci. USA, 88: 7247-7251, 1991.

Kozbor, A human hybrid myeloma for production of human monoclonal antibodies, J. Immunol., 133:3001-3005, 1984.

Letsinger, Cholesteryl-conjugated oligonucleotides: synthesis, properties, and activity as inhibitors of replication of human immunodeficiency virus in cell culture, PNAS USA, 86:6553-6556, 1989.

Leventis et al., Interactions of mammalian cells with lipid dispersions containing novel metabolizable cationic amphiphiles, Biochem. Biophys. Acta, 1023:124-132, 1990.

Lichtlen et al., "Antibody-based approaches in Alzheimer's research: safety, pharmacokinetics, metabolism, and analytical tools", Journal of Neurochemistry, 104: 859-874 (2008).

Lindmark et al., Binding of immunoglobulins to protein A and immunoglobulin levels in mammalian sera, J. Immunol. Methods, 62;1-13, 1983.

Lowman, Bacteriophage display and discovery of peptide leads for drug development, Ann. Rev. Biophys. Biomol. Struct., 26:401-424, 1997.

Malone et al., Cationic liposome-mediated RNA transfection, PNAS USA, 86:6077-6081, 1989.

Marks et al., By-passing immunization: human antibodies from V-gene libraries displayed on phage, J. Mol. Biol., 222:581-597, 1991.

Mather et al., Culture of testicular cats in hormone-supplemented serum-free medium, Ann. N.Y. Acad. Sci., 383:44-68, 1982.

Mather, Establishment and characterization of two distinct mouse testicular epithelial cell lines, Biol. Reprod, 23:243-251, 1980.

McGeer et al., Inflammation, autotoxicity and Alzheimer disease, Neurobiol. Aging, 22:799-889, 2001.

Miller, Human gene therapy comes of age, Nature, 357:455-460, 1992.

Misra et al., Drug delivery to the central nevous sysem: a review, J. Pharm. Pharmaceut. Sci., 6:252-273, 2003.

Morrison et al., Chimeric human antibody molecules: mouse antigen-binding domains with human constant region domains, PNAS USA, 81:6851-6855, 1984.

Morrison et al., Genetically engineered antibody molecules, Adv. Immunol., 44:65-92, 1988.

Ohmori et al., The enhancing effect of anionic alpha-helical peptide on cationic peptide-mediating transfection systems, Biochem. Biophys. Res. Commun., 235:726-729, 1997.

Paborsky et al., Mammalian Cell transient expression of tissue factor for the production of antigen, Protein Eng., 3:547-553, 1990.

Padlan, A possible procedure for reducing the immunogenicity of antibody variable domains while preserving their ligand-binding properties, Molec. Immunol., 28;489-498, 1991.

Padlan, Anatomy of the antibody molecule, Molec. Immunol., 31:169-217, 1994.

Pan et al., Efficient transfer of receptor-associated protein (RAP) across the blood-brain barrier, J. Cell Sci., 117:5071-5078, 2004.

Pan et al., Why study transport of peptides and proteins at the neurovascular interface?, Brain Res. Rev., 46:32-43, 2004.

Parasce et al., Slow degradation of aggregates of the Alzheimer's disease amyloid beta-protein by microglial cells, J. Biol. Chem., 272:29390-29397, 1997.

Park et al., Metabolic impairment induces oxidative stress, compromises inflammatory responses, and inactivates a key mitochondrial enzyme in microglia, J. Neurochem., 72:1948-1958, 1999.

Paul, Fundamental Immunology, (textbook), pp. 292-295, 1993.

Pinnaduwage et al., Use of a quaternary ammonium detergent in liposome mediated DNA transfection of mouse L-cells, Biochim. Biophys. Acta, 985:33-37, 1989.

Poduslo et al., Amyloid β peptide as a vaccine for Alzheimer's disease involves receptor-mediated transport at the blood-brain barrier, Clin. Neurosci., 12:3197-3200, 2001.

Poduslo et al., Design and chemical synthesis of a magnetic resonance contrast agent with enhanced in vitro binding, high blood-brain barrier permeability, and in vivo targeting to Alzheimer's disease amyloid plaques, Biochem., 43:6064-6075, 2004.

Pollard et al., Polyethylenimine but not cationic lipids promotes transgene delivery to the nucleus in mammalian cells, J. Biol. Chem., 273:7507-7511, 1998.

Riechmann et al., Reshaping human antibodies for therapy, Nature, 332:323-327, 1988.

Rose et al., A new cationic liposome reagent mediating nearly quantitative transfection of animal cells, Biotechniques, 10:520-525, 1991.

Rudikoff et al., Single amino acid substitution altering antigen-binding specificity, Proc. Natl. Acad. Sci. USA, 79:1979-1983, 1982.

Sanger et al., DNA sequencing with chain-terminating inhibitors, PNAS USA, 74:5463-5467, 1977.

Sarmay et al., Mapping and comparison of the interaction sites on the Fc region of IgG responsible for triggering antibody dependent cellular cytotoxicity (ADCC) through different types of human Fc gamma receptor, Molec. Immunol., 29:633-639, 1992.

Schenk et al., Current progress in beta-amyloid immunotherapy, Curr. Opin. Immunol., 16:599-606, 2004.

Schenk et al., Immunization with amyloid-β attenuates Alzheimer-disease-like pathology in the PDAPP mouse, Nature, 400:173-177, 1999.

Selkoe, Translating cell biology into therapeutic advances in Alzheimer's disease, Nature, 399:A23-A31, 1999.

Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276:6591-6604, 2001.

Shopes, A genetically engineered human IgG mutant with enhanced cytolytic activity, J. Immunol., 148:2918-2922, 1992.

Sinha et al., Purification and cloning of amyloid precursor protein beta-secretase from human brain, Nature, 402:537-540, 1999.

Sisodia et al., A role for the Beta-amyloid precursor protein in memory?, Proc Natl. Acad. Sci. USA, 95: 12074-12076, 1998.

Skerra et al., Assembly of a functional immunoglobulin Fv fragment in *Escherichia coil*, Science, 240:1038-1041, 1988.

Sojar et al., A chemical method for the deglycosylation of proteins, Arch. Biochem. Biophys., 259:52-57, 1987.

Soto et al., β-Sheet breaker peptides for the treatment of amyloidosis in Alzheimer disease, 7th International Geneva/Springfield Symposium on Advances in Alzheimer Therapy, 2002.

Steinberg, Testing potential Alzheimer vaccines, The Scientist, 16:22-23, 2002.

Stevenson et al., A chimeric antibody with dual Fc regions (bisFabFc) prepared by manipulations at the IgG hinge, Anti-cancer Drug Design, 3:219-230, 1989.

Studnicka et al., Human-engineered monoclonal antibodies retain full specific binding activity by preserving non-CDR complementarity-modulating residues, Protein Eng., 7:805-814, 1994.

Thotakura et al., Enzymatic deglycosylation of glycoproteins, Methods Enzymol., 138:350-359, 1987.

Urlaub et al., Isolation of Chinese hamster cell mutants deficient in dihydrofolate reductase activity, PNAS USA, 77:4216-4220, 1980.

Vajdos et al., Comprehensive functional maps of the antigen-binding site of an anti-ErbB2 antibody obtained with shotgun scanning mutagenesis, Journal of Molecular biology, vol. 320, pp. 415-428, 2002.

Verhoeyer et al., Reshaping human antibodies: grafting an antilysozyme activity, Science, 239:1534-1536, 1988.

Verma, Gene therapy, Sci. Am., 263:68-84, 1990.

Vinters, Cerebral amyloid angiopathy: a critical review, Stroke, 18:311-324, 1987.

Watkins, Screening of phage-expressed antibody libraries by capture lift, Methods Molec. Biol., 178:187-193, 2002.

Williams et al., The lyophilizaton of pharmaceuticals: a literature review, J. Parenter. Sci. Tech., 38:48-59, 1984.

Winter et al., Making antibodies by phage display technology, Annu. Rev. Immunol., 12:433-455, 1994.

Wolff et al., Monoclonal antibody homodimers: enhanced antitumor activity in nude mice, Cancer Res., 53:2560-2565, 1993.

Wolozin et al., Decreased prevalence of Alzheimer disease associated with 3-hydroxy-3-methyglutaryl coenzyme A reductase inhibitors, Arch. Neurol., 57:1439-1443, 2000.

Yan et al., Immunocytochemical localization of TrkB in the central nervous system of the adult rat., J. Comp. Neurol., 378:135-157, 1997.

Younkin, The role of A beta 42 in Alzheimer's disease, J. Physiol., 92:289-292, 1998.

Zapata et al., Engineering linear F(ab')2 fragments for efficient production in *Escherichia coli* and enhanced antiproliferative activity, Protein Eng., 8:1057-1062, 1995.

Zhou et al., Lipophilic polylysines mediate efficient DNA transfection in mammalian cells, Biochim. Biophys. Acta, 1065:8-14, 1991.

Internatonal Preliminary Report on Patentability, PCT/US2006/002259, International Bureau of WIPO. mated Jul. 24, 2007.

International Search Report, PCT/US2006/002259, European Patent Office, mailed Apr. 7, 2006.

Written Opinion of the International Searching Authority, PCT/US2006/002259, European Patent Office, mailed Apr. 7, 2006.

Tamura, M. et al., "Structural correlates of an anticarcinoma antibody: identification of specificity-determining residues (SDRs) and development of a minimally immunogenic antibody variant by retention of SDRs only", *J of Immunology*, 164: 1432-1441 (2000).

* cited by examiner

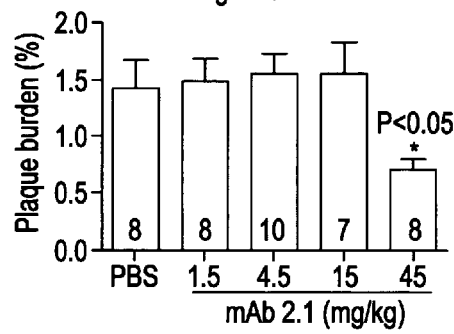
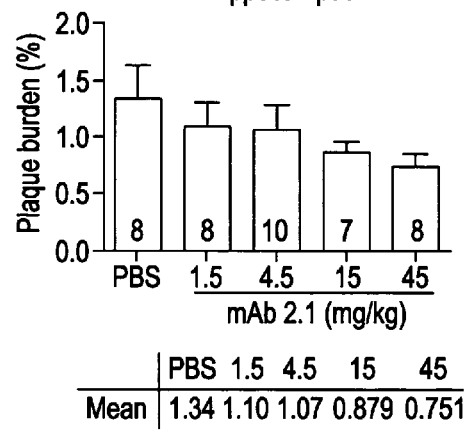
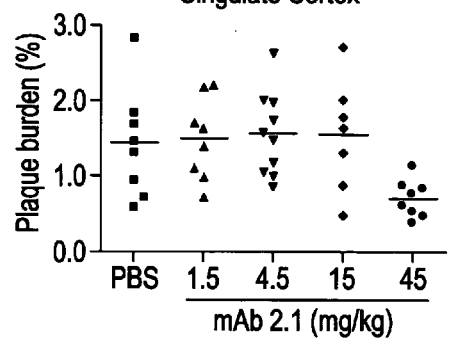
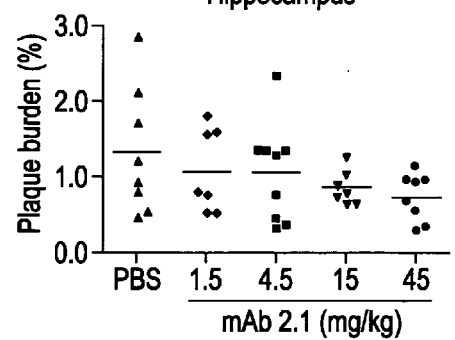

Cingulate Cortex

Hippocampus

Cingulate Cortex

Hippocampus

ANTI-AMYLOID ANTIBODIES AND USES THEREOF

This application is a national stage application under 35 U.S.C. 371 of International Application No. PCT/US2008/013881, having an international filing date of Dec. 19, 2008, which claims the benefit of U.S. Provisional Application No. 61/016,167, filed Dec. 21, 2007, which is hereby incorporated by reference in its entirety.

The instant application contains an ASCII "txt" compliant sequence listing submitted via EFS-WEB on Jun. 18, 2010, which serves as both the computer readable form (CRF) and the paper copy required by 37 C.F.R. Section 1.821(c) and 1.821(e), and is hereby incorporated by reference in its entirety. The name of the "txt" file which was created on Dec. 18, 2008, is: A-1388-WO-PCT SeqList-Off of 43034_Prov seq.txt, and is 127 kb in size.

TECHNICAL FIELD

This invention relates to compositions for treating neurodegenerative or amyloidogenic disorders such as Alzheimer's disease (AD), and more particularly, to compositions containing anti-amyloid-beta antibodies.

BACKGROUND OF THE INVENTION

Alzheimer's disease (AD) affects more than 12 million patients worldwide, accounting for most dementia diagnosed after the age of 60. The disease is clinically characterized by a global decline of cognitive function that progresses slowly and leaves end-stage patients bedridden, incontinent and dependent on custodial care; death occurs, on average, nine years after diagnosis (Davis et al., in Pharmacological Management of Neurological and Psychiatric Disorders, pp. 267-316, 1998). In addition to its direct effects on patients, advanced AD puts a tremendous burden on family caregivers and causes high nursing home costs for society. Age is the major risk factor for AD, and a health care crisis is likely in countries with aging populations if treatments that protect against the disease or delay or stop its progression cannot be introduced within the next decade. The current standard of care for mild to moderate AD includes treatment with acetylcholine-esterase inhibitors to improve cognitive function (Doody, R., *Alzheimer Dis. Assoc. Disord.*, 13:S20-S26, 1999). These drugs are safe, but of limited benefit to most patients.

SUMMARY OF THE INVENTION

The invention relates to specific binding agents, including antibodies, that bind with high affinity to amyloid-β (Aβ) and exhibit amyloid plaque reduction activity. The invention provides such specific binding agents, materials and methods for producing such specific binding agents, and methods of using such specific binding agents.

In a different aspect, the invention relates to specific binding agents, including antibodies, that exhibit pharmacokinetic parameters associated with a reduction in adverse effects or the incidence of adverse effects. Such pharmacokinetic parameters include: (a) high Cmax or a high initial concentration at about time zero ($C_0$), (b) low initial volume of distribution ($V_0$), or (c) low volume of distribution at steady state ($V_{ss}$). Specific binding agents that exhibit one, two or all of these pharmacokinetic properties are contemplated as an aspect of the invention.

Experiments performed in cynomolgus monkeys administered a humanized anti-amyloid antibody 2.1A (containing light chain amino acid sequence of SEQ ID NO: 45 and heavy chain amino acid sequence of SEQ ID NO: 47) at doses of ≦15 mg/kg resulted in an adverse event that appears to be associated with the antibody's pharmacokinetic parameters. When administered to cynomolgus monkeys at a dose of about 4.5 mg/kg, the humanized 2.1A antibody exhibited an initial serum concentration ($C_0$) of about 6.5 μg/mL an initial volume of distribution ($V_0$) of about 700 mL/kg), a volume of distribution at steady-state (Vss) of about 2410 mL/kg, and a clearance rate (CL) of greater than about 10 mL/kg/hr. Antibodies with different pharmacokinetic parameters are expected to produce fewer or less severe adverse effects.

Thus, in one aspect, the invention contemplates the use of specific binding agents characterized by reduced systemic effects and by one or more pharmacokinetic parameters (as measured in cynomolgus monkeys at a dose of about 4.5 mg/kg), including any one, two, three or all of the following:

(a) at least about [5-fold, 10-fold, 15-fold, 20-fold, 25-fold, 30-fold, 35-fold, or 40-fold] higher $C_0$ (or $C_{max}$) values compared to that obtained with humanized antibody 2.1 A, (b) at least about [3-fold, 4-fold, 5-fold, 10-fold, 15-fold, 20-fold, 25-fold, or 30-fold] lower $V_0$ values compared to that obtained with humanized antibody 2.1A, (c) at least about [3-fold, 4-fold, 5-fold, 10-fold, 15-fold, 20-fold, 25-fold, or 30-fold] lower $V_{ss}$ values compared to that obtained with humanized antibody 2.1A, (d) at least about [3-fold, 4-fold, 5-fold, 10-fold, 15-fold, 20-fold, 25-fold, 30-fold, 35-fold, 40-fold, 45-fold, or 50-fold] lower CL values compared to that obtained with humanized antibody 2.1A.

In some embodiments, the specific binding agents have higher $C_0$ (or $C_{max}$) and/or a lower $V_0$ values. In other embodiments, the specific binding agents have higher $C_0$ (or $C_{max}$), lower $V_0$ and lower $V_{ss}$ values. In exemplary embodiments, the specific binding agents are antibodies with pharmacokinetic values (as measured in cynomolgus monkeys given a dose of about 4.5 mg/kg) within the following ranges: $C_0$ ranging from about 35 μg/mL to 90 μg/mL, $V_0$ ranging from about 50 mL/kg to 150 mL/kg, and optionally $V_{ss}$ ranging from about 120 mL/kg to 600 mL/kg, and further optionally clearance values (CL) ranging from about 0.3 mL/kg/hr to 2 mL/kg/hr and reduced systemic effects such as vasculitis.

The specific binding agents, including antibodies, of the present invention can be used in the manufacture of a pharmaceutical composition or medicament. Exemplary embodiments of the invention include a pharmaceutical composition or medicament to treat an amyloidogenic disease, such as, but not limited to, Alzheimer's disease or primary systemic amyloidosis, in a human comprising a therapeutically effective amount of an antibody that when administered intravenously to a cynomolgus in a single dose of about 4.5 mg/kg is characterized by an initial concentration value ($C_0$) greater than about 10, about 20, about 30, about 40, about 50, about 60, or about 70 μg/mL, and/or up to 100, 125 or 150 μg/mL, and a sterile pharmaceutically acceptable diluent, carrier or excipient. In some embodiments, the antibody in the pharmaceutical composition may, alternatively, or in addition, be characterized by an initial volume of distribution ($V_0$) value less than about 600, about 500, about 400, about 300, about 200, or about 100 mL/kg. In some embodiments, the antibody in the pharmaceutical composition may, alternatively, or in addition to the preceding characteristics, produce a volume of distribution at steady state (Vss) value less than about 1000, about 900, about 800, about 700, about 600, about 500, about 400, about 300, or about 200 mL/kg.

In yet another aspect, the invention relates to specific binding agents that preferentially bind to certain forms of amyloid. For example, the invention contemplates specific binding agents that bind with 3-fold, 4-fold, 5-fold, 6-fold, 7-fold, 8-fold, 9-fold, 10-fold, 11-fold, 12-fold, 13-fold, 14-fold or 15-fold higher affinity to Aβ42 monomers compared to Aβ40 monomers.

In one embodiment, the invention provides isolated antibodies that specifically bind to amino acid residues 1-42 of amyloid beta (SEQ ID NO: 43) with a $k_d$ of about $1\times10^{-4}$ $s^{-1}$ or less as measured by BIAcore, and that comprises at least one amino acid sequence selected from the group consisting of SEQ ID NOs: 5-10, SEQ ID NOs: 15-20, SEQ ID NOs: 25-30, SEQ ID NOs: 35-40, SEQ ID NOs: 56-61, SEQ ID NOs: 66-71, SEQ ID NOs: 76-81, SEQ ID NOs: 86-91, SEQ ID NOs: 96-101, SEQ ID NOs: 106-111, SEQ ID NOs: 116-121, and SEQ ID NOs: 126-131.

In some embodiments, the isolated antibody comprises the amino acid sequences set forth in SEQ ID NOs: 5-10. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 2 and/or SEQ ID NO: 4.

In some embodiments, the isolated antibody comprises the amino acid sequences set forth in SEQ ID NOs: 15-20. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 12 and/or SEQ ID NO: 14.

In some embodiments, the isolated antibody comprises the amino acid sequences set forth in SEQ ID NOs: 25-30. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 22 and/or SEQ ID NO: 24.

In some embodiments, the isolated antibody comprises the amino acid sequences set forth in SEQ ID NOs: 35-40. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 32 and/or SEQ ID NO: 34.

In some embodiments, the isolated antibody comprises the amino acid sequences set forth in SEQ ID NOs: 56-61. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 53 and/or SEQ ID NO: 55.

In some embodiments, the isolated antibody comprises the amino acid sequences set forth in SEQ ID NOs: 66-71. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 63 and/or SEQ ID NO: 65.

In some embodiments, the isolated antibody comprises the amino acid sequences set forth in SEQ ID NOs: 76-81. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 73 and/or SEQ ID NO: 75.

In some embodiments, the isolated antibody comprises the amino acid sequences set forth in SEQ ID NOs: 86-91. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 83 and/or SEQ ID NO: 85.

In some embodiments, the isolated antibody comprises the amino acid sequences set forth in SEQ ID NOs: 96-101. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 93 and/or SEQ ID NO: 95.

In some embodiments, the isolated antibody comprises the amino acid sequences set forth in SEQ ID NOs: 106-111. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 103 and/or SEQ ID NO: 105.

In some embodiments, the isolated antibody comprises the amino acid sequences set forth in SEQ ID NOs: 116-121. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 113 and/or SEQ ID NO: 115.

In some embodiments, the isolated antibody comprises the amino acid sequences set forth in SEQ ID NOs: 126-131. In a related embodiment, the isolated antibody comprises and amino acid sequence at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identical to SEQ ID NO: 123 and/or SEQ ID NO: 125.

In some embodiments, the isolated antibody comprises a polypeptide comprising an at least one amino acid sequence selected from the group consisting of SEQ ID NO: 2, SEQ ID NO: 4, SEQ ID NO: 12, SEQ ID NO: 14, SEQ ID NO: 22, SEQ ID NO: 24, SEQ ID NO: 32, SEQ ID NO: 34, SEQ ID NO: 53, SEQ ID NO: 55, SEQ ID NO: 63, SEQ ID NO: 65, SEQ ID NO: 73, SEQ ID NO: 75, SEQ ID NO: 83, SEQ ID NO: 85, SEQ ID NO: 93, SEQ ID NO: 95, SEQ ID NO: 103, SEQ ID NO: 105, SEQ ID NO: 113, SEQ ID NO: 115, SEQ ID NO: 123 and SEQ ID NO: 125.

Also provided is an isolated antibody that comprises a first amino acid sequence of SEQ ID NO: 59; a second amino acid sequence selected from the group consisting of SEQ ID NO: 60, SEQ ID NO: 80 and SEQ ID NO: 160, with the proviso that when $X^1$ of SEQ ID NO: 160 is serine, $X^2$ of SEQ ID NO: 160 is not serine and $X^3$ of SEQ ID NO: 160 is not threonine; and a third amino acid sequence selected from the group consisting of SEQ ID NO: 61, SEQ ID NO: 81 and SEQ ID NO: 161.

Also provided is an isolated antibody that comprises a first amino acid sequence selected from the group consisting of SEQ ID NO: 5, SEQ ID NO: 15, SEQ ID NO: 35 and SEQ ID NO: 66; a second amino acid sequence selected from the group consisting of SEQ ID NO: 6 and SEQ ID NO: 67); and a third amino acid sequence selected from the group consisting of SEQ ID NO: 7, SEQ ID NO: 17, SEQ ID NO: 37 (LCDR3 Ab 1.9) and SEQ ID NO: 68.

Also provided is an isolated antibody that comprises a first amino acid sequence selected from the group consisting of SEQ ID NO: 56, SEQ ID NO: 126 and SEQ ID NO: 162, with the proviso that when $X^1$ of SEQ ID NO: 162 is serine, $X^3$ of SEQ ID NO: 162 is not serine, arginine or asparagine; a second amino acid sequence selected from the group consisting of SEQ ID NO: 57, SEQ ID NO: 77 and SEQ ID NO: 127; and a third amino acid sequence selected from the group consisting of SEQ ID NO: 58 and SEQ ID NO: 128.

Also provided is an isolated antibody that comprises a first amino acid sequence selected from the group consisting of SEQ ID NO: 86 and SEQ ID NO: 116; a second amino acid sequence selected from the group consisting of SEQ ID NO: 87 and SEQ ID NO: 117; and a third amino acid sequence selected from the group consisting of SEQ ID NO: 88 and SEQ ID NO: 118.

Nucleic acids encoding any of the preceding antibodies are also provided. In a related embodiment, a vector comprising any of the aforementioned nucleic acid sequences is provided. In still another embodiment, a host cell is provided comprising any of the aforementioned nucleic acids or vectors.

Numerous methods are contemplated in the present invention. For example, a method of producing an aforementioned specific binding agent is provided comprising culturing the aforementioned host cell such that the nucleic acid is expressed to produce the specific binding agent. Such methods may also comprise the step of recovering the specific binding agent from the host cell culture. In a related embodiment, an isolated specific binding agent produced by the aforementioned method is provided.

The invention further provides methods of using any of the preceding specific binding agents, for example, to treat or prevent a neurodegenerative or CNS disorder associated with amyloid-beta by administering an effective amount thereof, or to treat or prevent an amyloidogenic disease by administering an effective amount thereof.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIGS. 2A-2D illustrate quantitative morphological analysis of the plaque burden in cingulate cortex after treatment (1× per week) with mAb 2.1 IgG.

DETAILED DESCRIPTION

Figure 1:
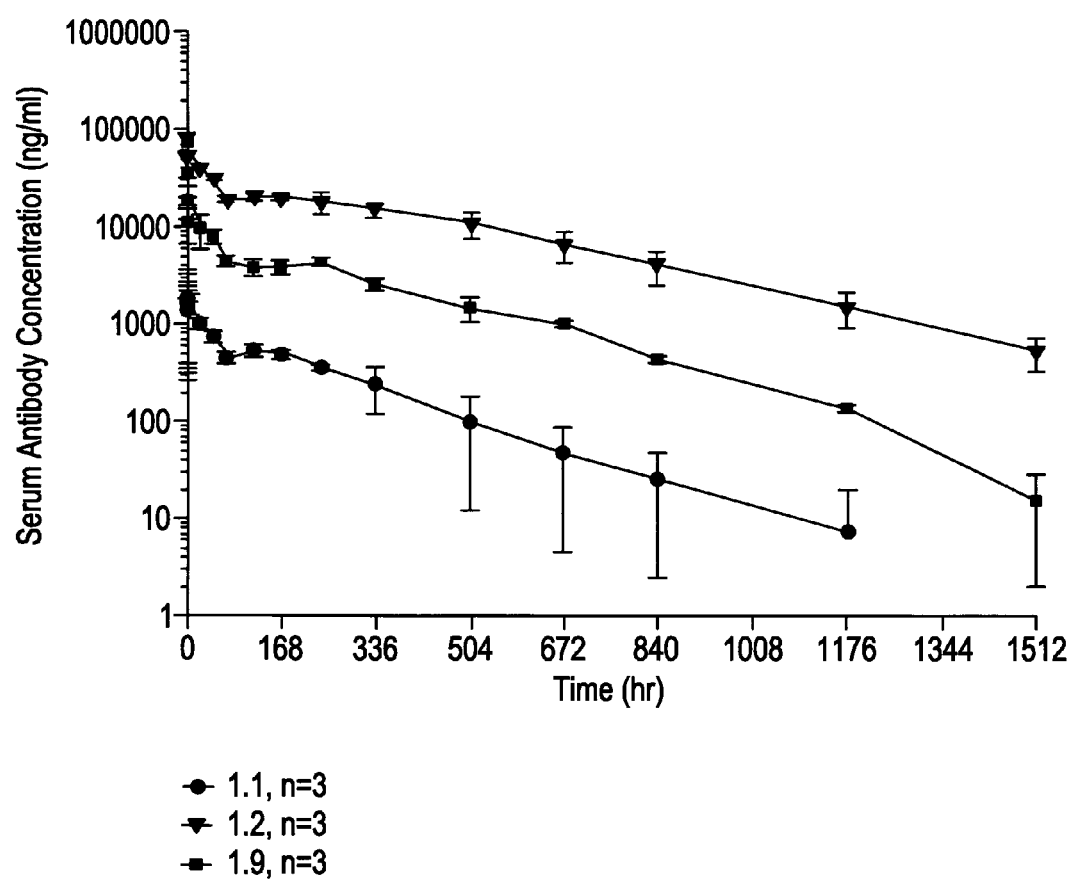
FIG. 1 shows the mean serum antibody concentration-time profiles following a single intravenous administration of 4.5 mg/kg of anti-Aβ antibody 1.1, 1.2 and 1.9 to male cynomolgus monkeys.

Deposits of aggregated amyloid β-peptide (Aβ) in parenchymal amyloid plaques are a defining criterion of Alzheimer's disease (AD) pathology, and Aβ aggregates (soluble or insoluble, oligomeric or fibrillar) are thought to trigger a pathogenic cascade resulting in the pathologic and clinical manifestations of AD. The primary component of amyloid plaques is a fibrillar aggregate comprising a 40 or 42 amino acid version of Aβ. Amyloid fibrils prepared in vitro from synthetic Aβ are morphologically indistinguishable from amyloid fibrils extracted from AD brain tissue (Kirschner et al., Proc. Natl. Acad. Sci. USA, 84:6593-6597, 1987). A number of antibody candidates prepared against the 40 or 42 amino acid version of Aβ were evaluated for their ability to bind to in vitro prepared Aβ40 and Aβ42 monomers, fibrils and/or aggregates.

In exemplary embodiments of the invention, antibodies to Aβ were produced using transgenic mice in which genes responsible for endogenous antibody production have been inactivated and into which large segments of human genes responsible for antibody production have been inserted. A number of antibody candidates prepared against the 40 or 42 amino acid version of Aβ were evaluated for their ability to bind to in vitro prepared Aβ 40 and Aβ42 monomers, fibrils and/or aggregates. Antibodies were also evaluated for in vitro and ex vivo activity on plaque reduction and other histologic features characteristic of Alzheimer's disease. For human origin antibodies that would elicit a mouse anti-human immune response, surrogate antibodies of murine origin, with similar binding avidity and affinity for Aβ monomers and fibrils compared to their human antibody counterparts, were tested in vivo in murine models of disease.

The amino acid sequences of the heavy chain of each of antibody 1.1, 1.2 and 1.9, respectively, are set forth in SEQ ID NOS: 135, (of which residues 20-138 are the variable region, and residues 139-468 are the constant region) 139, (of which residues 20-140 are the variable region, and residues 141-140 are the constant region) and 143 (of which residues 20-140 are the variable region, and residues 141-470 are the constant region. The amino acid sequences of the heavy chain variable region of each of antibodies 1.1, 1.2, 1.7, 1.9, 1.14, 1.15, 6.18, 6.27, 7.2, 7.11, 7.28 and 8.57, respectively, are set forth in SEQ ID NOS: 2, 12, 22, 32, 53, 63, 73, 83, 93, 103, 113 and 123. The cDNA sequences encoding the heavy chain of each of antibodies 1.1, 1.2 and 1.9, respectively, are set forth in SEQ ID NOS: 134 (of which residues 58-414 are the variable region, and residues 415-1,404 are the constant region), 138 (of which residues 58-420 are the variable region, and residues 421-1,410 are the constant region) and 142 (of which residues 58-420 are the variable region, and residues 421-1, 410 are the constant region). The amino acid sequences of the light chain of each of antibodies 1.1, 1.2 and 1.9, respectively, are set forth in SEQ ID NOS: 133 (of which residues 21-132 are the variable region, and residues 133-239 are the constant region), 137 (of which residues 21-132 are the variable region, and residues 133-239 are the constant region) and 141 (of which residues 21-132 are the variable region, and residues 133-239 are the constant region). The amino acid sequences of the light chain variable region of each of antibody 1.1, 1.2, 1.7, 1.9, 1.14, 1.15, 6.18, 6.27, 7.2, 7.11, 7.28 and 8.57, respectively, are set forth in SEQ ID NOS: 4, 14, 24, 34, 55, 65, 75, 85, 95, 105, 115 and 125. The cDNA sequences encoding the light chain of each of antibodies 1.1, 1.2 and 1.9, respectively, are set forth in SEQ ID NOS: 132 (of which residues 61-396 are the variable region, and residues 397-717 are the constant region), 136 (of which residues 61-396 are the variable region, and residues 397-717 are the constant region) and 140 (of which residues 61-396 are the variable region, and residues 397-717 are the constant region). The light and heavy chain CDRs (CDRL1, CDRL2, CDRL3, CDRH1, CDRH2, CDRH3) of antibodies 1.1, 1.2, 1.7, 1.9, 1.14, 1.15, 6.18, 6.27, 7.2, 7.11, 7.28 and 8.57, respectively are set forth in SEQ ID NOs: 5-10; SEQ ID NOs: 15-20; SEQ ID NOs: 25-30; SEQ ID NOs: 35-40; SEQ ID NOs: 56-61; SEQ ID NOs: 66-71; SEQ ID NOs: 76-81; SEQ ID NOs: 86-91; SEQ ID NOs: 96-101; SEQ ID NOs: 106-111; SEQ ID NOs: 116-121 and SEQ ID NOs: 126-131.

In one embodiment, the antibody comprises amino acids 20-468 of SEQ ID NO: 135 and amino acids 21-239 of SEQ ID NO: 133. In another embodiment, the antibody comprises amino acids 20-470 of SEQ ID NO: 139 and amino acids 21-239 of SEQ ID NO: 137. In another embodiment, the antibody comprises amino acids 20-470 of SEQ ID NO: 143 and amino acids 21-239 of SEQ ID NO: 141.

Antibody-antigen interactions can be characterized by the association rate constant in $M^{-1}s^{-1}$ ($k_a$), or the dissociation rate constant in $s^{-1}$ ($k_d$), or alternatively the dissociation equilibrium constant in M ($K_D$).

The present invention provides a variety of specific binding agents, including but not limited to human Aβ-specific antibodies, that exhibit desirable characteristics such as binding affinity as measured by $K_D$ (dissociation equilibrium constant) for Aβ aggregates in the range of $10^{-9}$ M or lower, ranging down to $10^{-12}$ M or lower, or avidity as measured by $k_d$ (dissociation rate constant) for Aβ aggregates in the range of $10^4$ $s^{-1}$ or lower, or ranging down to $10^{-10}$ $s^{-1}$ or lower, and/or amyloid-reducing activity and/or therapeutic efficacy for neurodegenerative or amyloidogenic disorders such as Alzheimer's disease or primary systemic amyloidosis. The invention also provides nucleic acids encoding such specific binding agent polypeptides, vectors and recombinant host cells comprising such nucleic acids, methods of producing such specific binding agents, pharmaceutical formulations including such specific binding agents, methods of preparing the pharmaceutical formulations, and methods of treating patients with the pharmaceutical formulations and compounds.

In some embodiments, the specific binding agents exhibit desirable characteristics such as binding avidity as measured by $k_d$ (dissociation rate constant) for Aβ or Aβ aggregates of about $10^{-2}$, $10^{-3}$, $10^{-4}$, $10^{-5}$, $10^{-6}$, $10^{-7}$, $10^{-8}$, $10^{-9}$, $10^{-10}$ $s^{-1}$ or lower (lower values indicating higher binding avidity), and/or binding affinity as measured by $K_D$ (dissociation equilibrium constant) for Aβ or Aβ aggregates of about $10^{-9}$, $10^{-10}$, $10^{-11}$, $10^{-12}$, $10^{-13}$, $10^{-14}$, $10^{-15}$, $10^{-16}$ M or lower (lower values indicating higher binding affinity). In some embodiments, the specific binding agents induce amyloid plaque phagocytosis in an assay such as described in Example 5 below with an $EC_{50}$ of 1 μg/mL. Preferably, the specific binding agents of the invention bind to unfixed plaques with high affinity ($K_D$ of about $10^{-10}$ M or better affinity) and avidity (kd of about $10^4$ $s^{-1}$ or better avidity). Dissociation rate constants or dissociation equilibrium constants may be readily determined using kinetic analysis techniques such as surface plasmon resonance (BIAcore), or KinExA using general procedures outlined by the manufacturer or other methods known in the art. The kinetic data obtained by BIAcore or KinExA may be analyzed by methods described by the manufacturer.

In some embodiments, the antibodies exhibit specificity for Aβ or Aβ aggregates or Aβ plaques. As used herein, an antibody is "specific for" an antigen when it has a significantly higher binding affinity for, and consequently is capable of distinguishing, that antigen compared to other unrelated proteins in different families. In some embodiments, the antibodies that bind to human Aβ cross-react with APP; while in other embodiments, the antibody binds only to Aβ and not to APP. In some embodiments, the antibodies that bind to human Aβ cross-react with Aβ of other species, such as murine, rat, or primate Aβ; while in other embodiments, the antibodies bind only to human or primate Aβ and not significantly to rodent Aβ. In some embodiments, antibodies specific for Aβ cross-react with other proteins in the same family, while in other embodiments, the antibodies distinguish Aβ from other related family members, such as amyloid precursor-like proteins.

In specific exemplary embodiments, the invention contemplates:

1) a monoclonal antibody that retains any one, two, three, four, five, or six of CDRH1, CDRH2, CDRH3, CDRL1, CDRL2 or CDRL3 of any of antibody 1.1, 1.2, 1.7, 1.9, 1.14, 1.15, 6.18, 6.27, 7.2, 7.11, 7.28 or 8.57, optionally including one or two mutations (insertion, deletion or substitution) in such CDR(s), 2) a monoclonal antibody that retains all of CDRH1, CDRH2, CDRH3, or the heavy chain variable region of any of antibody 1.1, 1.2, 1.7, 1.9, 1.14, 1.15, 6.18, 6.27, 7.2, 7.11, 7.28 or 8.57, optionally including one or two mutations in such CDR(s), 3) a monoclonal antibody that retains all of CDRL1, CDRL2, CDRL3, or the light chain variable region of any of antibody 1.1, 1.2, 1.7, 1.9, 1.14, 1.15, 6.18, 6.27, 7.2, 7.11, 7.28 or 8.57, optionally including one or two mutations in such CDR(s), 4) a monoclonal antibody that binds to the same epitope of Aβ as antibody 1.1, 1.2, 1.7, 1.9, 1.14, 1.15, 6.18, 6.27, 7.2, 7.11, 7.28 or 8.57, e.g. as determined through X-ray crystallography, or linear epitope binding; and/or 5) a monoclonal antibody that competes with antibody 1.1, 1.2, 1.7, 1.9, 1.14, 1.15, 6.18, 6.27, 7.2, 7.11, 7.28 or 8.57 for binding to Aβ by more than about 75%, more than about 80%, or more than about 81%, 82%, 83%, 84%, 85%, 86%, 87%, 88%, 89%, 90%, 91%, 92%, 93%, 94% or 95%.

In one embodiment, the antibody comprises at least one, two, three, four, five or all of the antibody 1.1 CDRs (SEQ ID NOS: 5-10). In another embodiment, the antibody comprises at least one, two, three, four, five or all of the antibody 1.2 CDRs (SEQ ID NOS: 15-20). In another embodiment, the antibody comprises at least one, two, three, four, five or all of the antibody 1.7 CDRs (SEQ ID NOS: 25-30). In another embodiment, the antibody comprises at least one, two, three, four, five or all of the antibody 1.9 CDRs (SEQ ID NOS: 35-40). In another embodiment, the antibody comprises at least one, two, three, four, five or all of the antibody 1.14 CDRs (SEQ ID NOS: 56-61). In another embodiment, the antibody comprises at least one, two, three, four, five or all of the antibody 1.15 CDRs (SEQ ID NOS: 66-71). In another embodiment, the antibody comprises at least one, two, three, four, five or all of the antibody 6.18 CDRs (SEQ ID NOS: 76-81). In another embodiment, the antibody comprises at least one, two, three, four, five or all of the antibody 6.27 CDRs (SEQ ID NOS: 86-91). In another embodiment, the antibody comprises at least one, two, three, four, five or all of the antibody 7.2 CDRs (SEQ ID NOS: 96-101). In another embodiment, the antibody comprises at least one, two, three, four, five or all of the antibody 7.11 CDRs (SEQ ID NOS: 106-111). In another embodiment, the antibody comprises at least one, two, three, four, five or all of the antibody 7.28 CDRs (SEQ ID NOS: 116-121). In another embodiment, the antibody comprises at least one, two, three, four, five or all of the antibody 8.57 CDRs (SEQ ID NOS: 126-131).

In some embodiments, the antibody comprises all three light chain CDRs, all three heavy chain CDRs, or all six CDRs. In some exemplary embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

Consensus CDRs may also be used. In an exemplary embodiment, the antibody comprises one or more of the amino acid sequences set forth in SEQ ID NOs: 31 or 32, wherein X is any amino acid and * can be absent or any amino acid. In another exemplary embodiment, the antibody comprises the amino acid sequence YISX$^1$X$^2$SSX$^3$IYYADSVKG (SEQ ID NO: 160), where X$^1$-X$^3$ are any amino acid, with the proviso that when X$^1$ is serine, X$^2$ is not serine and X$^3$ is not threonine. In another exemplary embodiment, the antibody comprises the amino acid sequence EX$^1$TX$^2$TTRX$^3$YYYYYGX$^4$DV (SEQ ID NO: 161), where X$^1$-X$^4$ o are any amino acid. In another exemplary embodiment, the antibody comprises the amino acid sequence RASQX$^1$X$^2$SSX$^3$X$^4$LA (SEQ ID NO: 162), where X$^1$-X$^4$ are any amino acid, with the proviso that when X$^1$ is serine, X$^3$ is not serine, arginine or asparagine.

In one embodiment, the antibody comprises a first amino acid sequence of SEQ ID NO: 59; a second amino acid sequence selected from the group consisting of SEQ ID NO: 60 and SEQ ID NO: 80 and SEQ ID NO: 160, with the proviso that when X$^1$ of SEQ ID NO: 160 is serine, X$^2$ of SEQ ID NO: 160 is not serine and X$^3$ of SEQ ID NO: 160 is not threonine; and a third amino acid sequence selected from the group consisting of SEQ ID NO: 61 and SEQ ID NO: 81.

In another embodiment the antibody comprises a first amino acid sequence of SEQ ID NO: 59; a second amino acid sequence selected from the group consisting of SEQ ID NO: 60 and SEQ ID NO: 80, and a third amino acid sequence selected from the group consisting of SEQ ID NO: 61, SEQ ID NO: 81 and SEQ ID NO: 161.

In another embodiment, the antibody comprises a first amino acid sequence selected from the group consisting of SEQ ID NO: 5, SEQ ID NO: 15 (LCDR11.2), SEQ ID NO: 35 and SEQ ID NO: 66; a second amino acid sequence selected from the group consisting of SEQ ID NO: 6 and SEQ ID NO: 67; and a third amino acid sequence selected from the group consisting of SEQ ID NO: 7 (LCDR3Ab 1.1), SEQ ID NO: 17, SEQ ID NO: 37 and SEQ ID NO: 68.

In yet another embodiment, the antibody comprises a first amino acid sequence selected from the group consisting of SEQ ID NO: 56, SEQ ID NO: 126 and SEQ ID NO: 162, with the proviso that when X' of SEQ ID NO: 162 is serine, X$^3$ of SEQ ID NO: 162 is not serine, arginine or asparagine; a second amino acid sequence selected from the group consisting of SEQ ID NO: 57, SEQ ID NO: 77 and SEQ ID NO: 127; and a third amino acid sequence selected from the group consisting of SEQ ID NO: 58 and SEQ ID NO: 128.

In yet another embodiment, the antibody comprises a first amino acid sequence selected from the group consisting of SEQ ID NO: 86 and SEQ ID NO: 116; a second amino acid sequence selected from the group consisting of SEQ ID NO: 87 and SEQ ID NO: 117; and a third amino acid sequence selected from the group consisting of SEQ ID NO: 88 and SEQ ID NO: 118.

In another embodiment, the antibody comprises a first amino acid sequence selected from the group consisting of SEQ ID NO: 8, SEQ ID NO: 18 and SEQ ID NO: 32; a second amino acid sequence selected from the group consisting of SEQ ID NO: 9, SEQ ID NO: 19 and SEQ ID NO: 33; and a third amino acid sequence selected from the group consisting of SEQ ID NO: 10 and SEQ ID NO: 20.

In yet another exemplary embodiment, the antibody comprises the light and/or heavy chain variable region, or both, of any of antibodies 1.1, 1.2, 1.7, 1.9, 1.14, 1.15, 6.18, 6.27, 7.2, 7.11, 7.28 or 8.57. In some embodiments, the antibody comprises (a) the light chain variable region of an antibody selected from the group consisting of 1.1, 1.2, 1.7, 1.9, 1.14, 1.15, 6.18, 6.27, 7.2, 7.11, 7.28 and 8.57 and (b) the heavy chain variable region of any of an antibody selected from the group consisting of 1.1, 1.2, 1.7, 1.9, 1.14, 1.15, 6.18, 6.27, 7.2, 7.11, 7.28 and 8.57. In some embodiments, the antibody comprises an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light and/or heavy chain variable region, or both, of any of antibodies 1.1, 1.2, 1.9, 1.14, 1.15, 6.18, 6.27, 7.2, 7.11, 7.28 or 8.57, and may comprise one, two or all three of the light chain CDRs and/or one, two, or all three of the heavy chain CDRs. In any of the foregoing embodiments, the specific binding agent or antibody polypeptide includes a sequence comprising one or two mutations to any of such CDRs.

In another exemplary embodiment, the antibody comprises the heavy chain variable region of any of antibodies 1.1, 1.2, 1.7, 1.9, 1.14, 1.15, 6.18, 6.27, 7.2, 7.11, 7.28 or 8.57 and optionally comprises a constant region selected from the group consisting of a human IgG1 heavy chain constant region (SEQ ID NOs: 144-145) and a human IgG2 heavy chain constant region (SEQ ID NOs: 146-147). In another exemplary embodiment, the antibody comprises the light chain variable region of any of antibodies 1.1, 1.2, 1.7, 1.9, 1.14, 1.15, 6.18 and 8.57 and optionally comprises a human kappa light chain constant region (SEQ ID NOs: 148-149). In another exemplary embodiment, the antibody comprises the light chain variable region of any of antibodies 6.27, 7.2, 7.11 and 7.28 and optionally comprises a constant region selected from the group consisting of a human lambda light chain constant region type C1 (SEQ ID NOs: 150-151), a human lambda light chain constant region type C2 (SEQ ID NOs: 152-153), a human lambda light chain constant region type C3 (SEQ ID NOs: 154-155), a human lambda light chain constant region type C6 (SEQ ID NOs: 156-157) and a human lambda light chain constant region type C7 (SEQ ID NO: 158-159).

The term "amyloid-beta" or "Aβ" refers to the naturally-occurring human amyloid-beta polypeptide set forth in SEQ ID NO: 43. Naturally-occurring human Aβ polypeptide ranges in length from 39 to 43 amino acids (residues 1 to 39, 1 to 40, 1 to 41, 1 to 42, or 1 to 43 of SEQ ID NO: 43) and is a proteolytic cleavage product of the amyloid precursor protein (APP).

The term "amyloidogenic disease" includes any disease associated with (or caused by) the formation or deposition of insoluble amyloid fibrils. Exemplary amyloidogenic disease include, but are not limited to Alzheimer's disease (AD), mild cognitive impairment, Parkinson's Disease with dementia, Down's Syndrome, Diffuse Lewy Body (DLB) disease, Cerebral Amyloid Angiopathy (CAA), vascular dementia and mixed dementia (vascular dementia and AD), amyloidosis associated with multiple myeloma, primary systemic amyloidosis (PSA), and secondary systemic amyloidosis with evidence of coexisting previous chronic inflammatory or infectious conditions. Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. PSA involves the deposition of insoluble monoclonal immunoglobulin (Ig) light (L) chains or L-chain fragments in various tissues, including smooth and striated muscles, connective tissues, blood vessel walls, and peripheral nerves.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "therapeutically effective amount" is meant to refer to an amount of Aβ-specific binding agent (including antibody) that provides a reduction in the number, size or complexity of amyloid plaques or amyloid aggregates in brain, or that provides a reduction in the severity or progression of symptoms associated with disease (i.e. that provides "therapeutic efficacy").

The phrase "amyloid-reducing activity" is meant to refer to the ability to inhibit, fully or partially, amyloid fibril formation, aggregation, or plaque formation or to remove or reduce existing amyloid fibrils, aggregates, or plaques.

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

The term "specific binding agent" includes antibodies as defined above and recombinant peptides or other compounds that contain sequences derived from CDRs having the desired antigen-binding properties.

An "isolated" antibody is one that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab', F'(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628[1991] and Marks et al., J. Mol. Biol., 222:581-597 (1991), for example.

An "immunoglobulin" or "native antibody" is a tetrameric glycoprotein. In a naturally-occurring immunoglobulin, each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies, the constant region is the same among different antibodies. Within the variable region of each heavy or light chain, there are three hypervariable subregions that help determine the antibody's specificity for antigen. The variable domain residues between the hypervariable regions are called the framework residues and generally are somewhat homologous among different antibodies. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1 m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10):1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')2 fragment that has two "Single-chain Fv" or "scFv" antibody fragments comprising the VH and VL domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 1 13, Rosenburg and Moore eds., Springer-Verlag, New York, pp. 269-315 (1994).

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

The term "modification" when used in connection with specific binding agents, including antibodies, of the invention, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. Modified specific binding agents of the invention will retain the binding properties of unmodified molecules of the invention.

The term "derivative" when used in connection with specific binding agents (including antibodies) of the invention refers to specific binding agents that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention.

Thus, the invention provides a variety of compositions comprising one, two, and/or three CDRs of a heavy chain variable region and/or a light chain variable region of an antibody including modifications or derivatives thereof. Such compositions may be generated by techniques described herein or known in the art.

As provided herein, the compositions for and methods of treating neurodegenerative disorders may utilize one or more anti-Aβ specific binding agents used singularly or in combination with other therapeutics to achieve the desired effects.

I. Production of Antibodies

Polyclonal Antibodies

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg of the protein or conjugate (for mice) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods.

In the hybridoma method, a mouse or other appropriate host animal, such as rats, hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by BIAcore or Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Recombinant Production of Antibodies

The invention provides isolated nucleic acids encoding any of the antibodies (polyclonal and monoclonal), including antibody fragments, of the invention described herein, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Similar materials and methods apply to production of polypeptide-based specific binding agents.

Relevant amino acid sequence from an immunoglobulin or polypeptide of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the specific binding agent (e.g., antibody) where, for example, the nucleic acid molecule is in a chromosomal location different from that of natural cells.

Once isolated, the DNA may be operably linked to expression control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

"Expression control sequences" refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia*

*marcescans*, and *Shigella*, as well as *Bacilli* such as *B. subtilis* and *B. licheniformis, Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Host cells for the expression of glycosylated specific binding agent, including antibody, can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of specific binding agent (including antibody) from such cells has become routine procedure. Examples of useful mammalian host cell lines are Chinese hamster ovary cells, including CHOK1 cells (ATCC CCL61), DXB-11, DG-44, and Chinese hamster ovary cells/–DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TR1 cells (Mather et al., Annals N.Y. Acad. Sci. 383: 44-68 (1982)); MRC 5 cells or FS4 cells; or mammalian myeloma cells.

Host cells are transformed or transfected with the above-described nucleic acids or vectors for production specific binding agents and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of specific binding agents.

The host cells used to produce the specific binding agents of the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the specific binding agent can be produced intracellularly, in the periplasmic space, or directly secreted into the medium. If the specific binding agent is produced intracellularly, as a first step, the particulate debris, either host cells or lysed fragments, is removed, for example, by centrifugation or ultrafiltration.

The specific binding agent can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., *J. Immunol. Meth.* 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric, Humanized and Human Engineered™ Antibodies

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217

(1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety.

Antibodies to Aβ can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); Mendez et al., *Nat. Genet.* 15:146-156 (1997); and U.S. Pat. No. 5,591,669, U.S. Pat. No. 5,589,369, U.S. Pat. No. 5,545,807; and U.S Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

Antibody Fragments

As noted above, antibody fragments comprise a portion of an intact full length antibody, preferably an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, maxibodies, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., *Science* 242:423-426, 1988, and Huston et al., *Proc. Natl. Acad. Sci. USA* 85:5879-5883, 1988). An Fd fragment consists of the $V_H$ and $C_H1$ domains.

Additional antibody fragments include a domain antibody (dAb) fragment (Ward et al., *Nature* 341:544-546, 1989) which consists of a $V_H$ domain.

"Linear antibodies" comprise a pair of tandem Fd segments ($V_H$-$C_H1$-$V_H$-$C_H1$) which form a pair of antigen binding regions. Linear antibodies can be bispecific or monospecific (Zapata et al. Protein Eng. 8:1057-62 (1995)).

A "minibody" consisting of scFv fused to $CH_3$ via a peptide linker (hingeless) or via an IgG hinge has been described in Olafsen, et al., Protein Eng Des Sel. 2004 April; 17(4):315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CuI domain. Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Camelized $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Methods for generating antibodies having camelized heavy chains are described in, for example, in U.S. Patent Publication Nos. 2005/0136049 and 2005/0037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001).

Intrabodies are single chain antibodies which demonstrate intracellular expression and can manipulate intracellular protein function (Biocca, et al., *EMBO J.* 9:101-108, 1990; Colby et al., *Proc Natl Acad Sci USA*. 101:17616-21, 2004). Intrabodies, which comprise cell signal sequences which retain the antibody contruct in intracellular regions, may be produced as described in Mhashilkar et al (EMBO J. 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med. Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Various techniques have been developed for the production of antibody fragments. Traditionally, these fragments were derived via proteolytic digestion of intact antibodies, but can also be produced directly by recombinant host cells. See, for example, Better et al., Science 240: 1041-1043 (1988); Skerra et al. Science 240: 1038-1041 (1988); Carter et al., Bio/Technology 10:163-167 (1992).

Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the anti-Aβ antibodies of the present invention can also be constructed to fold into multivalent forms, which may improve binding affinity, specificity and/or increased half-life in blood. Multivalent forms of anti-Aβ antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody.

Various techniques for making and isolating bispecific or multispecific antibody fragments directly from recombinant cell culture have also been described. For example, bispecific antibodies have been produced using leucine zippers, e.g. GCN4. (See generally Kostelny et al., J. Immunol. 148(5): 1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., Proc. Natl. Acad. Sci. USA, 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., J. Immunol. 152: 5368 (1994). One approach has been to link two scFv antibodies with linkers or disulfide bonds (Mallender and Voss, J. Biol. Chem. 269:199-2061994, WO 94/13806, and U.S. Pat. No. 5,989, 830, the disclosures of which are incorporated herein by reference in their entireties).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol*. 246:367-73, 1995).

Production of bispecific Fab-scFv ("bibody") and trispecific Fab-(scFv)(2) ("tribody") are described in Schoonjans et al. (*J Immunol*. 165:7050-57, 2000) and Willems et al. (*J Chromatogr B Analyt Technol Biomed Life Sci*. 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

Specific Binding Agents

Other Aβ-specific binding agents can be prepared, for example, based on CDRs from an antibody or by screening libraries of diverse peptides or organic chemical compounds for peptides or compounds that exhibit the desired binding properties for Aβ. Aβ-specific binding agent include peptides containing amino acid sequences that are at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more identical to one or more CDRs of human antibody 1.1 (SEQ ID NOs: 5-10); human antibody 1.2 (SEQ ID NOs: 15-20); human antibody 1.7 (SEQ ID NOs: 25-30) or human antibody 1.9 (SEQ ID NOs: 35-40), SEQ ID NOs: 56-61 (Ab 1.14), SEQ ID NOs: 66-71 (Ab 1.15), SEQ ID NOs: 76-81 (Ab 6.18), SEQ ID NOs: 86-91 (Ab 6.27), SEQ ID NOs: 96-101 (Ab 7.2), SEQ ID NOs: 106-111 (Ab 7.11), SEQ ID NOs: 116-121 (Ab 7.28) and SEQ ID NOs: 126-131 (Ab 8.57).

Aβ-specific binding agents also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be cappe, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

II. Production of Specific Binding Agent Variants

Amino acid sequence variants of the desired specific binding agent may be prepared by introducing appropriate nucleotide changes into the encoding DNA, or by peptide synthesis. Such variants include, for example, deletions and/or insertions and/or substitutions of residues within the amino acid sequences of the specific binding agents or antibodies. Any combination of deletion, insertion, and substitution is made to arrive at the final construct, provided that the final construct possesses the desired characteristics. The amino acid changes also may alter post-translational processes of the specific binding agent, such as changing the number or position of glycosylation sites. In certain instances, specific binding agent variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

Nucleic acid molecules encoding amino acid sequence variants of the specific binding agent or antibody are prepared by a variety of methods known in the art. Such methods include oligonucleotide-mediated (or site-directed) mutagenesis, PCR mutagenesis, and cassette mutagenesis of an earlier prepared variant or a non-variant version of the specific binding agent.

A useful method for identification of certain residues or regions of the specific binding agent that are preferred locations for mutagenesis is called "alanine scanning mutagenesis," as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Ordinarily, amino acid sequence variants of the specific binding agent will have an amino acid sequence having at least 60% amino acid sequence identity with the original specific binding agent or antibody amino acid sequences of either the heavy or the light chain variable region, or at least 65%, or at least 70%, or at least 75% or at least 80% identity, more preferably at least 85% identity, even more preferably at least 90% identity, and most preferably at least 95% identity, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the original sequence, after aligning the sequences and introducing gaps, if necessary, to achieve the maximum percent sequence identity, and not considering any conservative substitutions (as defined in Table I below) as part of the sequence identity. None of N-terminal, C-terminal, or internal extensions, deletions, or insertions into the specific binding agent or antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include a specific binding agent with an N-terminal methionyl residue or the specific binding agent (including antibody or antibody fragment) fused to an epitope tag or a salvage receptor epitope. Other insertional variants of the specific binding agent or antibody molecule include the fusion to a polypeptide which increases the serum half-life of the specific binding agent, e.g. at the N-terminus or C-terminus.

Examples of epitope tags include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.) are well known and routinely used in the art.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the specific binding agent molecule removed and a different residue inserted in its place. Substitutional mutagenesis within any of the hypervariable or CDR regions or framework regions is contemplated. Conservative substitutions are shown in Table 1. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the specific binding agent are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the specific binding agent also may be substituted, generally with serine, to improve the oxidative stability of the molecule and prevent aberrant crosslinking. Conversely, cysteine bond(s) may be added to the specific binding agent to improve its stability (particularly where the specific binding agent is an antibody fragment such as an Fv fragment).

In certain instances, specific binding agent variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which specific binding agent amino acid residues are important for epitope recognition and binding, alanine scanning mutagenesis can be performed to produce substitution variants. See, for example, Cunningham et al., Science, 244:1081-1085 (1989), the disclosure of which is incorporated herein by reference in its entirety. In this method, individual amino acid residues are replaced one-at-a-time with an alanine residue and the resulting anti-Aβ specific binding agent is screened for its ability to bind its specific epitope relative to the unmodified polypeptide. Modified specific binding agents with reduced binding capacity are sequenced to determine which residue was changed, indicating its significance in binding or biological properties.

Substitution variants of specific binding agents can be prepared by affinity maturation wherein random amino acid changes are introduced into the parent polypeptide sequence. See, for example, Ouwehand et al., Vox Sang 74 (Suppl 2):223-232, 1998; Rader et al., Proc. Natl. Acad. Sci. USA 95:8910-8915, 1998; Dall'Acqua et al., Curr. Opin. Struct. Biol. 8:443-450, 1998, the disclosures of which are incorporated herein by reference in their entireties. Affinity maturation involves preparing and screening the anti-Aβ specific binding agents, or variants thereof and selecting from the resulting variants those that have modified biological properties, such as increased binding affinity relative to the parent anti-Aβ specific binding agent. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA.* 102:8466-71, 2005). Nonstochastic techniques often use alanine-scanning or site-directed mutagenesis to generate limited collections of specific muteins. Some methods are described in further detail below.

Affinity maturation via panning methods—Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA.* 97:2029-34, 2000).

Look-through mutagenesis—Look-through mutagenesis (LTM) (Rajpal et al., *Proc Natl Acad Sci USA.* 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol. Biol. 226:889-96, 1992). After the mutation cycles, clones with improved affinity for the antigen are selected using routine methods in the art.

Techniques utilizing gene shuffling and directed evolution may also be used to prepare and screen anti-Aβ specific binding agents, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

Specific Binding Agents with Modified Carbohydrate

Specific binding agent variants can also be produced that have a modified glycosylation pattern relative to the parent polypeptide, for example, adding or deleting one or more of the carbohydrate moieties bound to the specific binding agent, and/or adding or deleting one or more glycosylation sites in the specific binding agent.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent by inserting or substituting one or more serine or threonine residues to the sequence of the original specific binding agent or antibody.

Altered Effector Function

Cysteine residue(s) may be removed or introduced in the Fc region of an antibody or Fc-containing polypeptide, thereby eliminating or increasing interchain disulfide bond formation in this region. A homodimeric specific binding agent thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric specific binding agents or antibodies may also be prepared using heterobifunctional cross-linkers as described in Wolff et al., Cancer Research 53: 2560-2565 (1993). Alternatively, a specific binding agent can be engineered which has dual Fc regions and may thereby have enhanced complement lysis and ADCC capabilities. See Stevenson et al., *Anti-Cancer Drug Design* 3: 219-230 (1989).

It has been shown that sequences within the CDR can cause an antibody to bind to MHC Class II and trigger an unwanted helper T-cell response. A conservative substitution can allow the specific binding agent to retain binding activity yet reduce its ability to trigger an unwanted T-cell response. It is also contemplated that one or more of the N-terminal 20 amino acids of the heavy or light chain are removed.

Modifications to increase serum half-life also may desirable, for example, by incorporation of or addition of a salvage receptor binding epitope (e.g., by mutation of the appropriate region or by incorporating the epitope into a peptide tag that is then fused to the specific binding agent at either end or in the middle, e.g., by DNA or peptide synthesis) (see, e.g., WO96/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the specific binding agent or fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the specific binding agent or antibody. Alternatively, the epitope is taken from the CH2 domain of the Fc region and transferred to the $C_L$ region or $V_L$ region, or both, of the specific binding agent fragment. See also International applications WO 97/34631 and WO 96/32478 which describe Fc variants and their interaction with the salvage receptor.

Other sites and amino acid residue(s) of the constant region have been identified that are responsible for complement dependent cytotoxicity (CDC), such as the C1q binding site, and/or the antibody-dependent cellular cytotoxicity (ADCC) [see, e.g., Molec. Immunol. 29 (5): 633-9 (1992); Shields et al., J. Biol. Chem., 276(9):6591-6604 (2001); Lazar et al., Proc. Nat'l. Acad. Sci. 103(11): 4005 (2006) which describe the effect of mutations at specific positions, each of which is incorporated by reference herein in its entirety]. Mutation of residues within Fc receptor binding sites can result in altered (i.e. increased or decreased) effector function, such as altered affinity for Fc receptors, altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

The invention also contemplates production of specific binding agent molecules, including antibodies) with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 2004 Sep. 5; 87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol. Immunol. 1989 December; 26(12):1113-23). Some host cell strains, e.g. Lec13 or rat hybridoma YB2/0 cell line naturally produce antibodies with lower fucosylation levels. Shields et al., J Biol. Chem. 2002 Jul. 26; 277(30):26733-40; Shinkawa et al., J Biol. Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. 1999 February; 17(2):176-80. It has been predicted that the absence of only one of the two fucose residues may be sufficient to increase ADCC activity. (Ferrara et al., J Biol. Chem. 2005 Dec. 5).

Other Covalent Modifications

Covalent modifications of a specific binding agent, are also included within the scope of this invention. They may be made by chemical synthesis or by enzymatic or chemical cleavage of the specific binding agent or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd..C.dbd.N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the specific binding agent in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the specific binding agent may be accomplished chemically or enzymatically. Chemical deglycosylation requires exposure of the specific binding agent to the compound trifluoromethanesulfonic acid, or an equivalent compound. This treatment results in the cleavage of most or all sugars except the linking sugar (N-acetylglucosamine or N-acetylgalactosamine), while leaving the specific binding agent intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a specific binding agent can be achieved by the use of a variety of endo- and exo-glycosidases as described by Thotakura et al. Meth. Enzymol. 138: 350 (1987).

Another type of covalent modification of the specific binding agents of the invention (including anti-Aβ antibodies) comprises linking the specific binding agent to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

III. Gene Therapy

Delivery of a therapeutic specific binding agent to appropriate cells can be effected via gene therapy ex vivo, in situ, or in vivo by use of any suitable approach known in the art. For example, for in vivo therapy, a nucleic acid encoding the desired specific binding agent or antibody, either alone or in conjunction with a vector, liposome, or precipitate may be injected directly into the subject, and in some embodiments, may be injected at the site where the expression of the specific binding agent compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl. Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC)(Leventis et al. (1990) Biochim. Inter. 22, 235-241); 3beta[N—(N',N'-dimethylaminoethane)-carbamoyl]cholesterol (DC-Chol), dioleoylphosphatidyl ethanolamine (DOPE)/3beta[N—(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutypere-soxy] ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include specific binding agents specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, specific binding agents for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

IV. Administration and Preparation of Pharmaceutical Formulations

The anti-Aβ specific binding agents or antibodies used in the practice of a method of the invention may be formulated into pharmaceutical compositions and medicaments comprising a carrier suitable for the desired delivery method. Suitable carriers include any material which, when combined with the anti-Aβ specific binding agent or antibody, retains the high-affinity binding of Aβ and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary specific binding agent concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the specific binding agent may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the specific binding agent, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the specific binding agent formulation to reduce aggregation of the formulated specific binding agent and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. specific binding agent, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the specific binding agent are prepared for storage by mixing the specific binding agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of specific binding agents are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the specific binding agent, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The specific binding agent is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific binding agent is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the specific binding agent of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

Administration to Brain

A variety of approaches are known in the art to effect administration of compounds to the brain. For example, a compound may be administered by direct intraventricular or intrathecal injection, preferably via slow infusion to minimize impact on brain parenchyma. The desired drug may also be delivered using a slow release implant in the brain, or (where the drug is a polypeptide) implanted recombinant cells that produce the drug. The blood brain barrier (BBB) may be permeabilized concomitant with drug administration, to permit movement of the drug across the BBB. Permeabilizing agents include osmotic agents, such as hypertonic mannitol, or another permeabilizing agent such as bradykinin, an alkylglycerol, ultrasound, electromagnetic radiation or parasympathetic innervation.

Alternatively, receptor-mediated transport may be utilized to administer drug to the brain. It is known in the art that peptides and proteins that directly cross the BBB may serve as carriers for selective therapeutic agents that allow the therapeutic agents to cross the BBB after delivery into the bloodstream (Pan et al., Brain Research Reviews, 46:32-43, 2004; Misra et al., J. Pharm. Pharmaceut. Sci., 6:252-273, 2003; Begley, Pharmacol Ther. 2004 October; 104(1):29-45; Poduslo, US App. Pub. No. 2003/0082191; Poduslo et al., Biochem., 43:6064-6075, 2004). For example, Poduslo, WO 03/020212 describes conjugation of antibodies to amyloid-beta protein fragments which are then taken up by low-density lipoprotein receptor related protein-1, a transporter at the BBB. Other examples of peptides which cross the BBB include transferrin which binds to the transferrin receptor, a transporter at the BBB; monoclonal antibodies to the transferrin receptor such as OX26; cell penetrating peptides such as TAT transduction domain, penetratin, or Syn B1; and RAP which binds to low-density lipoprotein receptor related protein-2, another transporter at the BBB (see Pan et al., J Cell Sci. 2004 Oct. 1; 117(Pt 21):5071-8).

Receptor-mediated drug delivery to the brain may employ chimeric peptide technology, wherein a non-transportable drug is conjugated to a BBB transport vector. The latter may be a modified protein or receptor-specific monoclonal antibody that undergoes receptor-mediated transcytosis through the BBB in-vivo. Conjugation of drug to transport vector is facilitated with chemical linkers, avidin-biotin technology, polyethylene glycol linkers, or liposomes. Multiple classes of therapeutics have been delivered to the brain with the chimeric peptide technology, including peptide-based pharmaceuticals, anti-sense therapeutics including peptide nucleic acids (PNAs), and small molecules incorporated within liposomes. Alternatively, the drug may be encapsulated in a liposome or nanoparticle which is then linked to the BBB transport vector.

Administration with Other Agents

The specific binding agents of the invention also may be concurrently administered with other anti-amyloidogenic therapeutic agents. Concurrent administration includes administration of the two different therapeutic agents at different times and at different routes, as long as there is some overlap in the time during which the agents are exerting their therapeutic effects.

Exemplary anti-amyloidogenic agents known in the art include other anti-amyloid-beta antibodies (U.S. Pat. No. 6,787,637 and U.S. Patent Publication Nos. 2004/0171815 and 2004/0171816), anti-inflammatories known in the art (e.g., NSAIDs and Cox-2 inhibitors) that reduce the pathogenic effects of amyloid accumulation, cholesterol lowering drugs, β-secretase inhibitors, γ-secretase inhibitors, peptidic β-secretase inhibitors (Sinha et al., Nature, 402:537-540, 1999), small-molecule inhibitors of the interaction between Aβ and glycosaminoglycans (F. Gervais et at., 7th International Geneva/Springfield Symposium on Advances in Alzheimer Therapy, 2002), short peptidic Aβ derivatives (C. Soto et al., 7th International Geneva/Springfield Symposium on Advances in Alzheimer Therapy, 2002), chelating zinc with the antibiotic clioquinol (Chemy et al., Neuron, 30:665-66, 2001; Bush et al., PNAS, 98:8850-8855, 2001) or anti-inflammatories that reduce the inflammatory response due to the administration of anti-Aβ specific binding agent or that allow monitoring of the side effects of the anti-Aβ specific binding agent.

The invention is illustrated by the following examples, which are not intended to be limiting in any way.

EXAMPLES

Example 1

Production and Purification of Anti-Amyloid Antibodies

Xenomouse® IgG$_1$-κ, IgG$_1$-κλ, and IgG$_4$-κλ mice were generated generally as described previously in Mendez et al., Nat. Genet. 15:146-156 (1997) and immunized with Aβ$_{40}$ fibrils, Aβ$_{42}$ fibrils, Aβ$_{40}$ monomer and Aβ$_{42}$ monomer, respectively, emulsified in complete Freund's adjuvant for primary immunization and in incomplete Freund's adjuvant for subsequent injections using standard methods. The mice were immunized twice weekly, via footpad administration, with each mouse receiving 100 μg fibrillar Aβ or 20 μg monomeric Aβ per injection. Serum antibody titers were measured every 2 weeks. Monomeric Aβ elicited a weaker immune response compared to Aβ fibrils.

Hybridomas were generated by fusing spleen and/or lymph node cells from seropositive animals with sp2/0 myeloma cell line as described in MendeZ et al., supra. Supernatants from hybridomas were screened for binding to fibrillar Aβ (mixture of Aβ$_{40}$ and Aβ$_{42}$) in an ELISA format. Supernatants were collected from all positive hybridoma cell lines and were purified using Protein A affinity chromatography.

Several antibodies were selected for further analysis, including antibodies designated 1.1, 1.2, 1.7 and 1.9.

Example 2

In Vitro Binding of Antibodies

This example evaluates the in vitro binding of the antibodies 1.1, 1.2, 1.7 and 1.9 to Aβ (monomer and fibrils) and to collagen fibrils. All candidates were run at multiple concentrations in order to obtain concentration response information (where response=binding). From the concentration response curve one can determine an EC50 (the concentration that provokes a response halfway between baseline and maximum response). The EC$_{50}$ is reflective of binding affinity; however, under the conditions used here, it is not a direct measure of K$_D$. As a negative control, collagen fibrils were used to assess non-specific binding of antibodies.

The fibrils (Aβ or collagen) were diluted to 10 μg/ml in water and mixed thoroughly. The solution was aliquoted into the wells of a microtiter plate (Immulon-2; VWR; Cat #62404-972) at 50 μl per well (resulting in 0.5 μg fibrils/well final). The plate was dried overnight by being placed uncovered in a 37° C. incubator.

The same techniques were used for the coating of the microtiter plate for monomer ELISA. The fibrils Aβ monomer were diluted to 2.5 μg/ml in Coating buffer and mixed thoroughly. The solution was aliquoted into the wells of a microtiter plate [Immulon-2; VWR; Cat.#62404-972] at 100 μl per well. The plate was sealed and incubated overnight at 4° C. The plate was washed 5-10× to remove Aβ coating solution prior to starting the assay.

The wells were blocked with 200 μl of blocking solution and incubated for ≧1 hour at room temperature (RT) with shaking. The blocking solution was flicked out and gently dried on a paper towel. 100 μl of primary antibody diluted in PBS containing 10% blocking solution was added to each well and the plate was incubated at RT for 1 hour with shaking. The plate was washed with 5-10× in TBS, pH 7.5+0.05% Tween 20. 100 μl of secondary antibodies (each diluted 1-2,000-fold in PBS) was added to each well and the plate was incubate at RT for 1 hour with shaking. The plate was washed with 5-10× in TBS, pH 7.5+0.05% Tween 20. 100 μl Streptavidin-Europium reagent (1-1,000-fold dilution) was added (100 μL/well) and the plate was incubated at room temperature for 45 minutes with shaking. The plate was washed 5-10× in TBS, pH 7.5+0.05% Tween 20. 120 μl Enhance Solution was added and the plate was incubated at room temperature for 15-30 minutes with shaking. The plate was read on a Victor TRF plate reader (Europium program).

Antibodies 1.1, 1.2, 1.7 and 1.9 all demonstrated strong binding to Aβ 40 and Aβ 42 fibrils, with EC$_{50}$s ranging from 90 to 200 μM on Aβ$_{40}$ fibrils and from 70 to 100 μM on Aβ$_{42}$ fibrils. Antibodies 1.1, 1.2, 1.7 and 1.9 also showed binding to Aβ$_{42}$ monomer, with EC$_{50}$s ranging from 30 to 60 μM. Antibodies 1.1 and 1.9 also showed binding to Aβ$_{40}$ monomer, with an EC$_{50}$ ranging from 40 to 60 μM. None of the antibodies tested showed any binding in the collagen fibril counter-screen. (See Table 2 below).

TABLE 2

| ELISA Assay | 1.1 (EC50) | 1.2 (EC50) | 1.7 (EC50) | 1.9 (EC50) |
|---|---|---|---|---|
| Fibrillar Aβ40 | $13.3 \times 10^{-11}$ M | $11.5 \times 10^{-11}$ M | $9.0 \times 10^{-11}$ M | $19.5 \times 10^{-11}$ M |
| Fibrillar Aβ42 | $8.2 \times 10^{-11}$ M | $8.6 \times 10^{-11}$ M | $7.1 \times 10^{-11}$ M | $9.6 \times 10^{-11}$ M |
| Fibrillar collagen | No binding | No binding | No binding | No binding |
| Aβ40 monomer | $5.4 \times 10^{-11}$ M | $68.9 \times 10^{-11}$ M | $61.5 \times 10^{-11}$ M | $4.2 \times 10^{-11}$ M |
| Aβ42 monomer | $4.5 \times 10^{-11}$ M | $5.6 \times 10^{-11}$ M | $5.2 \times 10^{-11}$ M | $3.7 \times 10^{-11}$ M |

The in vitro binding assay described above was repeated using various other human anti-Aβ antibodies (1.14, 1.15, 5.1, 5.2, 5.3, 6.14, 6.18, 6.27, 6.7, 7.2, 7.11, 7.28, 7.29, 7.32, 8.53, 8.50 and 8.57) using mAb 2.1 chimera as a positive control. (The cDNA and amino acid sequences of the light and heavy variable regions of mAb 2.1 chimera are set forth in SEQ ID NOs: 163-164 and 165-166, respectively. The cDNA and amino acid sequences of the light and heavy chains of mAb 2.1 chimera are set forth in SEQ ID NOs: 167-168 and 169-170, respectively). A visual qualitative assessment of ELISA results for these antibodies indicated that antibodies 7.2, 7.28, 8.50 and 8.57 bound to amyloid monomers and aggregates with as good affinity as mAb 2.1 Chimera (all scored 5/5). Antibodies 1.15 and 7.11 scored 4/5. Antibodies 1.14, 5.3, 6.7, 6.14, 6.18, 6.27, 7.29, 7.32 and 8.53 scored 3/5. Antibodies 5.1, 5.2 scored 2/5.

Example 3

Kinetic Analysis of Antibody Binding to Human Aβ-Peptides

Kinetic binding analysis was performed using BIAcore to study the interaction of antibodies 1.1, 1.2, 1.7 and 1.9 with human Aβ40 and Aβ42 fibrils and monomers.

Preparation of Biacore Chip Surfaces: Immobilization of Proteins to a BIAcore sensor chip (CM5) was performed according to manufacturer's instructions. Briefly, carboxyl groups on the sensor chip surfaces were activated by injecting 60 μL of a mixture containing 0.2 M N-ethyl-N'-(dimethylaminopropyl) carbodiimide (EDC) and 0.05 M N-hydroxysuccinimide (NHS). Specific surfaces were obtained by injecting rProtein G (Pierce), goat anti-mouse Fc (Jackson Immuno Research Lab) or Aβ aggregates diluted in 10 mM acetate, pH 4.0 at concentrations between 5 and 20 μg/mL. Excess reactive groups on the surfaces were deactivated by injecting 60 μL of 1 M ethanolamine. Final immobilized levels were about 10000 resonance units (RU) for the Protein G and anti-mouse Fc surfaces, and 400 RU for the Aβ fibrils surfaces. A blank, mock-coupled reference surface was also prepared on the sensor chips for background subtraction.

Kinetic analysis of antibodies binding to immobilized Aβ fibrils: Avidity measurements to Aβ fibrils were made by immobilizing amyloid fibrils on the sensor chip surface followed by injection of antibody solutions over the surface, and injection of antibody solutions over a blank surface for background subtraction. Antibodies were diluted in PBS+0.005% P-20+0.1 mg/mL BSA at concentrations varying from 100 nM to 0.2 nM. Results are displayed in Table 3 below.

Kinetic analysis of Aβ monomers binding to protein G captured antibodies: The kinetic analysis of the interaction between Aβ monomers and antibodies was performed as follows: Antibodies to be tested were diluted in PBS+0.005% P-20+0.1 mg/mL BSA and injected over the immobilized protein G Fc surface. Aβ monomers were diluted in PBS+ 0.005% P-20+0.1 mg/mL BSA from 1000 nM to 2 nM, and each concentration was injected over the captured antibody surfaces. Results are displayed in Table 4 below.

Kinetic data analysis of the sensorgrams was performed using BIAevaluation, v. 3.2 (Biacore, Inc., Uppsala, Sweden) to extract $k_a$ and $k_d$. $K_D$ was estimated as $k_d/k_a$. Note that antibodies with off rates smaller than $5 \times 10^{-5}$ s$^{-1}$ could not be differentiated in this assay.

Results: Both Aβ monomers and fibrils were tested for binding with antibodies 1.1, 1.2, 1.7 and 1.9 using BIAcore. The $K_D$ of the antibodies binding to the monomers varied from 6 nM to over 200 nM, as determined in the kinetic analysis. The binding between the Aβ fibrils and the antibodies was much stronger that the binding between the Aβ monomers and the antibodies. Tables 3 and 4 below summarize the results of the antibodies binding to Aβ monomers and fibrils.

TABLE 3

Avidities of antibodies 1.1, 1.2, 1.7 and 1.9 to Aβ$_{40}$ and Aβ$_{42}$ amyloid fibrils.

| | Aβ$_{40}$ Fibrils | | | Aβ$_{42}$ Fibrils | | |
|---|---|---|---|---|---|---|
| Antibody | $K_D$ (nM) | $k_a$ (1/Ms) | $k_d$ (1/s) | $K_D$ (nM) | $k_a$ (1/Ms) | $k_d$ (1/s) |
| 1.1 | 0.02 | $4.2 \times 10^6$ | $8.1 \times 10^{-5}$ | 0.8 | $2.0 \times 10^5$ | $1.6 \times 10^{-4}$ |
| 1.2 | 0.06 | $2.9 \times 10^6$ | $1.7 \times 10^{-4}$ | 1.7 | $1.7 \times 10^5$ | $1.9 \times 10^{-4}$ |
| 1.7 | 0.1 | $3.8 \times 10^6$ | $4.2 \times 10^{-4}$ | 2.9 | $1.7 \times 10^5$ | $5.0 \times 10^{-4}$ |
| 1.9 | 0.03 | $5.3 \times 10^6$ | $1.7 \times 10^{-4}$ | 1.8 | $1.1 \times 10^5$ | $1.9 \times 10^{-4}$ |

TABLE 4

Affinities of antibodies 1.1, 1.2, 1.7 and 1.9 to soluble $A\beta_{40}$ and $A\beta_{42}$.

| Antibody | $A\beta_{40}$ Monomer | | | $A\beta_{42}$ Monomer | | |
|---|---|---|---|---|---|---|
| | $K_D$ (nM) | $k_a$ (1/Ms) | $k_d$ (1/s) | $K_D$ (nM) | $k_a$ (1/Ms) | $k_d$ (1/s) |
| 1.1 | 117 | $1.3 \times 10^5$ | $1.5 \times 10^{-2}$ | 16 | $2.4 \times 10^5$ | $3.9 \times 10^{-3}$ |
| 1.2. | >200 | n.d. | n.d. | 14 | $7.8 \times 10^4$ | $1.1 \times 10^{-3}$ |
| 1.7 | >200 | n.d. | n.d. | >20 | n.d. | n.d. |
| 1.9 | >200 | n.d. | n.d. | 47 | $6.1 \times 10^4$ | $2.9 \times 10^{-3}$ |

A slower dissociation rate ($k_d$) is helpful to the antibodies' ability to bind to plaques in brain tissue and induce phagocytosis of amyloid.

The kinetic analysis assay as described above was repeated using various other human anti-Aβ antibodies (1.14, 1.15, 5.1, 5.2, 5.3, 6.14, 6.18, 6.27, 6.7, 7.2, 7.11, 7.28, 7.29, 7.32, 8.53, 8.50 and 8.57). Table 5 summarizes the results of anti-Aβ antibodies binding to Aβ fibrils.

TABLE 5

Binding of Human to Aβ 40 and Aβ 42 fibrils

| Antibody | Aβ 40 fibrils $k_d$(1/s) | Aβ 42 fibrils $k_d$(1/s) |
|---|---|---|
| 1.14 | $1.3 \times 10^{-3}$ | $8.7 \times 10^{-4}$ |
| 1.15 | $9.6 \times 10^{-4}$ | $1.1 \times 10^{-3}$ |
| 5.1 | $1.9 \times 10^{-3}$ | $8.8 \times 10^{-4}$ |
| 5.2 | $2.4 \times 10^{-3}$ | $1.2 \times 10^{-3}$ |
| 5.3 | $7.8 \times 10^{-4}$ | $5.0 \times 10^{-4}$ |
| 6.14 | $2.6 \times 10^{-3}$ | $2.9 \times 10^{-3}$ |
| 6.18 | $4.0 \times 10^{-3}$ | $2.6 \times 10^{-3}$ |
| 6.27 | $5.0 \times 10^{-3}$ | $2.1 \times 10^{-3}$ |
| 6.7 | $1.6 \times 10^{-3}$ | $1.8 \times 10^{-3}$ |
| 7.2 | $1.4 \times 10^{-4}$ | $2.9 \times 10^{-4}$ |
| 7.11 | $8.0 \times 10^{-4}$ | $4.9 \times 10^{-4}$ |
| 7.28 | $8.2 \times 10^{-5}$ | $2.1 \times 10^{-4}$ |
| 7.29 | $7.1 \times 10^{-4}$ | $6.5 \times 10^{-4}$ |
| 7.32 | $3.2 \times 10^{-3}$ | $2.8 \times 10^{-3}$ |

The kinetic analysis assay as described above was performed using various other human anti-Aβ antibodies (8.53, 8.50 and 8.57). Antibodies 8.53, 8.50 and 8.57 have comparable binding to Aβ40 fibrils and Aβ42 fibrils as antibodies 1.14, 1.15, 5.1, 5.2, 5.3, 6.14, 6.18, 6.27, 6.7, 7.2, 7.11, 7.28, 7.29 and 7.32.

Example 4

Analysis of Antibody Binding to Aβ Oligomer

Aβ42 oligomers were prepared according to published methods (Lambert et al, 1998). Briefly, Aβ42 peptide (dry powder) was suspended in HFIP to a concentration of 2 mg/mL and the solution was allowed to evaporate to dryness in a fume hood. Residual HFIP was removed by vacuum centrifugation for 10 minutes. Dried Aβ42 resolubilized in DMSO to a concentration of 5 mM (22.5 mg/mL) followed by dilution 100 μM (0.45 mg/mL) in ice-cold Ham's F-12 media (phenol red free). Following incubation at 4° C. (from 24-48 h), insoluble material was removed by centrifugation 14,000 rpm for 15 minutes in a tabletop centrifuge. Supernatant containing soluble, Aβ42 monomer and oligomers was used immediately for immunoprecipitation.

Immunoprecipitation/Western Blot protocol: Aβ 42 oligomers (1.2 μg/mL) were immunoprecipitated overnight at 4° C. with 5 μg/mL anti-Aβ antibody and 30-40 μL Protein G agarose beads. Incubations were spun at 3,000 rpm for 5 min at 4° C. in an Eppendorf tabletop centrifuge. Supernatants were discarded and beads were washed for 20 min at 4° C. in the following 3 wash buffers: 1st wash—1 mL 0.5 M NaCl STEN buffer; 2nd wash—1 mL SDS-STEN buffer; and 3rd wash—1 mL 1×STEN buffer. Following each wash, beads were collected by centrifugation at 6,000 g for 5 min at 4° C. Following the final wash step, antibody/Aβ complexes were eluted with 14 μL 2× Tris-Glycine Sample Buffer. Samples were heated for 5 min at 100° C. and spun for 5 min at 14,000 rpm. Supernatatants were loaded into NuPAGE 12% Bis-Tris pre-cast gels and run in MES running buffer at 200 V for approximately 1 h (until gel front reached bottom of gel). Gel contents were transferred to a nitrocellulose membrane using the Novex transfer box and NuPAGE transfer buffer with 20% methanol. Transfer was performed at 25 V for 1 h. To increase Western Blot sensitivity, the membrane was heated in PBS as follows: microwaved in pipette box lid (one membrane per lid) on high for 3-4 min, making certain PBS came to a boil. Membrane was then cooled for 1.5 min, flipped and microwaving was repeated. Membrane was then blocked with 5% NFDM in TBST for 0.5 hr at RT. Blocking solution was removed and a solution of detection antibody (6E10 at 1 μg/mL) was added to the membrane and allowed to incubate for 1 hr at RT with shaking. The membrane was then washed 3 times by incubation with 1% NFDM in TBST for 5 minutes at RT with shaking. Following the washes, a solution of secondary antibody (peroxidase-labeled goat anti-mouse IgG) diluted 1:5000 in 1% NFDM was added to the membrane and allowed to incubate with shaking at RT for 30 minutes. The membrane was then washed in TBST as before. The membrane was developed using the ECL+Plus Detection System as follows: 100 pit Solution B was added to 4 mL of Solution A; the mixture was then added to the membrane and incubated for 5 minutes at room temperature without shaking. The membrane was then exposed to film in a dark room for 10 sec, 30 sec, 1 min, and 5 min, and the film was processed using a Kodak X-OMAT film processor. If re-exposure was necessary, subsequent exposure times were adjusted based on initial result.

Discussion: Antibodies 1.1, 1.2, 1.7 and 1.9 were assessed for their ability to bind to soluble, oligomeric species of Aβ42 using an immunoprecipitation/Western blot procedure. Antibodies 1.1, 1.2, 1.7 and 1.9 and the controls, murine mAb 4G8, all demonstrated the ability to bind to soluble, monomeric and oligomeric Aβ42 species. Based on a set of molecular weight standards, the primary species captured by immunoprecipitation corresponded to a molecular weight consistent with Aβ42 monomer (i.e., 4-5 kD). Additionally, Aβ42 species with apparent molecular weights corresponding to Aβ42 dimer, trimer, and tetramer (ie, 8-9 kD, 12-14 kD and 16-18 kD, respectively) were also immunoprecipitated.

Example 5

Immunohistochemical Analysis of Antibodies on Tg2576 Mouse Brain and Human Brain Sections The ability of antibodies 1.1, 1.2, 1.7 and 1.9 to bind to native amyloid plaques in situ was evaluated in unfixed fresh frozen tissue sections of human AD brain and of Tg2576 transgenic mouse brains.

Tissue Specimens: Animals sacrifices with inhalation of $CO_2$ and were perfused with saline. Brains were dissected out from the skull and bisected at the mid-line. Half of the brain is frozen on dry ice for future biochemical study and the other half is embedded in OCT embedding medium and frozen on dry ice for histology studies. Frozen human cortex from a 74-year old female Alzheimer's Disease subject and an 81-year old normal female subject were obtained from the Human Brain and Spinal Fluid Resource Center (CA Greater Los Angeles Healthcare System, Los Angeles, Calif.).

Histology: 14 µm-thick fresh-frozen coronal serial sections of mouse brains or the cerebral cortex of a human AD brain are cut using a cryostat microtome. Sections are thaw-mounted onto Fisher "plus" microscope slides and briefly air-dried. Sections are stored at –20° C. until use. At the time of staining, sections are warmed to room temperature and the endogenous tissue peroxidase activity is destroyed by incubating with 3% $H_2O_2$ in PBS for 15 minutes.

For evaluation of antibodies 1.1, 1.2, and 1.9 on mouse brains, sections are incubated in a blocking solution (3% normal goat serum/5% normal horse serum/0.25% carrageenan lambda/0.1% triton/PBS) for 1 hour. Sections are incubated with 1 µg/ml test antibody in the above blocking solution at 4° C. overnight. Sections are then incubated with 2 µg/ml biotinylated goat anti-human IgG on the shaker at room temperature for 1 hour.

For evaluation of antibodies 1.1, 1.2, and 1.9 on human brains, sections are incubated in a blocking solution (3% normal goat serum/5% normal horse serum/0.25% carrageenan lambda/0.1% triton/PBS) for 1 hour. Sections are incubated with 1 µg/ml biotinylated test antibody in the above blocking solution at 4° C. overnight.

Antigen is detected by ABC/DAB protocol as described in Yan et al, *J. Comp. Neurol.*, 378:135-157 (1997). Sections are dehydrated and cover-slipped with mounting medium.

Unfixed sections of a 20 month-old Tg25476 mouse brain containing a substantial amount of amyloid plaques were used to test the ability of antibodies to recognize native mouse amyloid plaques. A commercially available anti-Aβ antibody, mAb 4G8, was used as a positive control. Blinded samples were scored visually for plaque number, intensity, and non-specific background, and assigned a score from 1-5, with 5 representing the most intense staining. Antibodies 1.1, 1.2, 1.7 and 1.9 all stained Aβ plaques with high intensity (score=5) and with low to medium non-specific tissue binding (score=1-2). Irrelevant mouse monoclonal IgG showed no staining as expected.

Next, unfixed sections from a 74 year-old AD brain was used to evaluate if antibodies could recognize human amyloid plaques. Consistent with results on transgenic mouse tissue, all of antibodies 1.1, 1.2, 1.7 and 1.9 efficiently bound unfixed plaques. Irrelevant mouse monoclonal IgG showed no staining as expected.

Immunohistochemistry analysis as described above was repeated using various other human anti-Aβ antibodies (1.14, 1.15, 5.1, 5.2, 5.3, 6.14, 6.18, 6.27, 6.7, 7.2, 7.11, 7.28, 7.29, 8.32, 8.53, 8.50 and 8.57 on unfixed sections of a 19 month-old Tg25476 mouse brain containing a substantial amount of amyloid plaques. The staining intensity observed is set forth in Table 6 below. Irrelevant mouse monoclonal IgG showed no staining as expected.

TABLE 6

Staining intensities of Tg25476 mouse brain sections

| Antibody | IHC Score |
|---|---|
| 1.14 | 3 |
| 1.15 | 4 |
| 5.1 | 5 |
| 5.2 | 4+/5 |
| 5.3 | 5 |
| 6.14 | 4+/5 |
| 6.18 | 5 |
| 6.27 | 5+ |
| 6.7 | 5 |
| 7.2 | 3–/4+ |
| 7.11 | 4+/5 |
| 7.28 | 4 |
| 7.29 | 4 |
| 7.32 | 3+ |
| 8.53 | 3 |
| 8.50 | 1+/2 |
| 8.57 | 1+/2 |

Example 6

Functional Activity of Antibodies in Ex Vivo Phagocytosis Assay

In this ex vivo phagocytosis assay, candidate antibodies were characterized for their ability to induce phagocytosis of amyloid deposits in brain sections of Tg2576 mice or a human AD patient. Human-derived or humanized antibodies cannot be dosed chronically in a murine model of disease. The phagocytosis assay has been shown to be a good predictor of in vivo antibody efficacy (reduction of plaque burden) in mouse models of Alzheimer's disease. Antibody efficacy appears to be dependent on both binding to unfixed plaques and avidity.

Cell line culture. IC-21 and other cells were obtained from ATCC and culture in RPMI (Gibco BRL) supplemented with 2 mM L-glutamine, 1.5 g/L sodium bicarbonate, 4.5 g/L glucose, 10 mM HEPES (Gibco BRL), 1.0 mM sodium pyruvate (Gibco BRL) and 10% fetal bovine serum. Confluent cultures of IC-21 cells were detached from the T-75 plastic culture flask with 1% trypsin (Gibco BRL). The cell suspension was centrifuged at 1000 rpm and resuspended in the assay medium consisting of hybridoma-serum free medium with 1% FBS, glutamine, penicillin/streptomycin and 5 ng/ml mGM-CSF to a density of $1.6 \times 10^6$ cells/mL prior to use in the phagocytosis assay.

Phagocytosis assay. The antibodies were tested at a concentration ranging from 0.0001 µg/ml to 10 µg/ml. For selected antibodies, a full range of dose-response curves was generated. Briefly, a 10 µm cryostat section of 18-19 month-old female Tg2576 mouse brains were thawed and mounted onto poly-lysine coated glass coverslips and placed in wells of 24-well tissue culture plates. The coverslips were washed twice with the assay medium. Control or anti-Aβ antibodies were added at 2× final concentration in the 0.15 ml assay medium for 1 hour at incubator (37° C., 5% $CO_2$). 0.15 ml of microglial cells (phagocytosis competent IC-21 cells) were then seeded at a density of $1.6 \times 10^6$ cells/ml assay medium. The cultures were incubated in a humidified incubator (37° C., 5% $CO_2$) for 24 hours or more. At the end of the incubation, ex vivo samples were fixed with 4% paraformaldehyde for 1 hour at room temperature and washed with PBS. Sections were then incubated with blocking solution consisting of 5% normal goat serum (Vector, Burlingame, Calif.) and 0.4% Triton-X100 at room temperature for 2 hours. Specimens were incubated overnight at 4° C. in block buffer and stained with biotinylated mouse antibody 6E10 (3 µg/mL) (Senetek, St. Louis, Mo.) and rat anti-CD11b) 10 µg/mL) (or rat anti-CD45 and rat anti-F4/80, Serotec, Raleigh, N.C.) followed by a streptavidin-FITC (Vector Labs, Burlingame, Calif.) and goat anti-rat IgG-Cy3 or rat anti-rat IgG-texas red (Jackson ImmunoResearch, West Grove, PS). The sections were observed, and photographed with a confocal microscope (Nikon) using SimplePCI software (Compix Inc., PA). Amyloid plaques (diameter of 10-100 µm), microglia (diameter of 10-20 µm) and internalized amyloid (green inside red ring representing microglia surface stain) can easily be distinguished by using confocal microscopy with optical planes of 0.5 µm thickness. Any plaque that was associated with an IC21 cell containing internalized amyloid was counted as a positive event.

Analysis. For quantification of phagocytosis, one brain section per concentration point was used, covering antibody concentrations in the range of 0.0001-10 µg/ml. 50-100 cortical plaques were examined at 40× magnification, and both, partially and completely internalized plaques were counted as positive events. The percentage of plaques being phagocytosed was calculated and plotted over the antibody concentration. Determination of $EC_{50}$, defined as the concentration of test antibody at which 50% of plaques count as positive events as described above, together with a maximum percentage reached at 10 µg/ml, allowed ranking of antibodies with regard to phagocytic potency. Data were plotted and $EC_{50}$ values were determined by using the Prism software v4.01 (GraphPad, San Diego, Calif.).

Amyloid plaques remained intact and no phagocytosis was observed in the presence of 0.001-10 µg/ml irrelevant mouse IgG. In contrast, after incubation of adjacent sections in the presence of 10 µg/ml antibody, extracellular amyloid deposits were almost completely resolved and instead were localized within the microglial cells.

To confirm that this was internalization, confocal microscopy was used to scan serially focal planes of 0.5 µm thickness from top to bottom of plaques at 40× objective. The Z-series of optical planes showed that in the presence of 10 µg of antibody, microglia engulfed all amyloid; however, in the presence of mouse IgG control antibody, exogenous microglial cells remained in a confocal plane above the tissue section and contained no amyloid deposits, whereas amyloid remained in the plaques with the tissue plane. These results demonstrate that the tested antibodies had the ability to trigger phagocytosis of amyloid and lead to amyloid clearance.

Results and Discussion: In order to quantify antibody induced phagocytosis of amyloid, an ex vivo phagocytosis experiment was performed on antibodies 1.1, 1.2, 1.7 and 1.9 in full concentration titration (0.0001, 0.001, 0.01, 0.1, 1.0, 3, and 10 µml). Phagocytic events were defined as partially and completely internalized amyloid plaques as described above. The percentage of plaques being phagocytosed was calculated and plotted over the antibody concentration. Antibodies 1.1, 1.2, 1.7 and 1.9 induced 75-90% phagocytosis. In the presence of control mouse IgG, no phagocytosis was seen. $EC_{50}$ values for antibodies 1.1, 1.2 and 1.9 were 0.6-0.8 µg/ml. This was equivalent to the $EC_{50}$ value for a positive control antibody of 0.6 µg/ml. Antibody 1.7 induced a slightly lower amount of phagocytosis ($EC_{50}$=2.0 µg/ml), which was not observed in a repeated assay. The assay was repeated and these data with respect to antibodies 1.1, 1.2 and 1.9 were confirmed. Specifically, in the repeated assay antibodies 1.1, 1.2 and 1.9 induced similar amounts of phagocytosis (i.e., $EC_{50}$ ranging from 0.3-1.0 µg/ml). In the repeated assay, antibody 1.7 induced amounts of phagocytosis similar to those of antibodies 1.1, 1.2 and 1.9. Taken together, these data indicate that fully human Aβ-specific monoclonal antibodies 1.1, 1.2, 1.7 and 1.9 induced efficient phagocytosis of brain-derived amyloid plaques.

Example 7

Treatment of APP Transgenic Tg2576 Mice

The ability of peripherally administered anti-Aβ antibodies 1.1, 1.2, 1.7, 1.9, 1.14, 1.15, 6.18, 6.27, 7.2, 7.11, 7.28 and 8.57 to reduce amyloid plaque burden is evaluated in APP transgenic Tg2576 mice overexpressing Aβ. Studies with murine antibodies of similar affinity and avidity indicate that it is possible to identify amyloid phagocytosing microglial cells after just a single i.p. injection in vivo. Thus, functional activity of antibodies 1.1, 1.2, 1.7, 1.9, 1.14, 1.15, 6.18, 6.27, 7.2, 7.11, 7.28 and 8.57, can be evaluated qualitatively in this assay by identifying amyloid phagocytosis by endogenous microglia.

Treatment: At 13, 14, 15, 16, 17 or older months of age, mice are treated with a single intraperitoneal injection with control vehicle, or test antibody.

PK Sampling: Blood samples (50-100 µL) for PK analysis are collected from mice from the test antibody and control antibody group into serum separator tubes (Microtainer Brand) through the tail vein at pre-dose, e.g., 24 hrs after the $1^{st}$ dose, and pre-necropsy, e.g., 7 days post-dose. At the end of the study, animals are euthanized by $CO_2$ inhalation followed immediately by the collection from both dose groups of approximately 1 mL of blood through cardiopuncture into a serum separator tube (Microtainer Brand) for PK analysis. Serum samples are prepared and stored at −80° C. until analysis for levels of test article by time-resolved fluorescence immunoassay.

Brain Dissection: Following the blood collection, the brain is dissected out from the skull and bisected at the mid-line. Half of the brain is frozen on dry ice for future biochemical study and the other half is embedded in OCT embedding medium and frozen on dry ice for histology studies.

Histology: 14 mm-thick fresh frozen coronal serial sections are cut in a cryostat microtome. Sections are thaw-mounted onto Fisher "plus" microscope slides and air-dried. Sections were stored at −20° C. until use. At the time of staining, sections are warmed to room temperature and fixed in 4% paraformaldehyde/0.1 M phosphate buffer, pH 7.2, for 1 hr. The endogenous tissue peroxidase activity is destroyed by incubating with 3% H$_2$O$_2$ in PBS for 20 min. Sections are then incubated with 88% formic acid for 20 min to expose Aβ epitope and then with blocking solution (3% normal goat serum/5% normal horse serum/0.25% carrageenan lambda/0.1% triton/PBS) for 1 hr. Sections are incubated with 0.5 μg/mL biotinylated anti-human Aβ monoclonal antibody 4G8 (Senetek, St. Louis, Mo.) or a control biotinylated mouse myeloma IgG (Sigma, St. Louis, Mo.) in the above blocking solution at 4° C. overnight. The antigen is detected by ABC/DAB protocol as described in Yan et al., *J. Comp. Neurol.*, 378:135-157 (1997). Sections are dehydrated and cover-slipped with mounting medium. Some sections are used for thioflavine-S staining according to standard histology protocol to detect fibril form of amyloid plaques in the brain parenchyma and amyloid plaque associated with cerebral blood vessels (cerebral amyloid angiopathy, CAA).

In vivo phagocytosis: The brain sections are fixed with 4% paraformaldehyde for 1 hr followed by incubation with blocking solution (same as above) for 1 hr. The sections are then incubated overnight with 10 μg/mL of biotinylated-6E10 (Senetek, St. Louis, Mo.) and rabbit anti-CSF-1R antiserum (Upstate, Lake Placid, N.Y.) diluted 1:250. The sections are stained with streptavidin-FITC (diluted 1:200) and goat anti-rabbit IgG-Texas Red (Vector Lab, Burlingame, Calif.) (diluted 1:200). The sections are then analyzed using a confocal microscope.

All the quantitative results are analyzed by one-way ANOVA test followed by Newman-Keuls test using Prism software version 4.01 (GraphPad Software, San Diego, Calif.). All results are expressed as the mean±error of mean.

Little or no plaques are present in the brains of Tg2576 mice at age 7.5-8 months. By age 13.5-14 months, substantial numbers of amyloid plaques are expected to exist in the cortex and hippocampus of the control animals. As the animals grow older, their plaque burden increases. Examination of the cingulate cortex, piriform cortex, and hippocampus is also performed.

The ability of activated microglia to phagocytose Aβ after the treatment with anti-amyloid antibody is studied. Sections from the three treatment groups are double stained with a plaque marker and an activated microglial marker and then examined under a confocal microscope. In the control group, Aβ deposits are expected to remain intact with no indication of phagocytosis. In the treated groups, the Aβ deposits are expected to be surrounded by an increased level of activated microglia compared to the level of activated microglia in the control group, indicating the initiation of an increased phagocytic response. Treatment with antibodies 1.1, 1.2, 1.7, 1.9, 1.14, 1.15, 6.18, 6.27, 7.2, 7.11, 7.28 and 8.57 are expected to increase the number of phagocytic events.

The above example is expected to indicate that treatment with anti-Aβ antibodies results in increased phagocytosis of amyloid plaque burden.

Example 8

Treatment of APP Transgenic Tg2576 Mice with mAb 2.1 IgG

The ability of peripherally administered anti-Aβ antibody 2.1 (comprising heavy and light chains of SEQ ID NOS: 49 and 51) to reduce amyloid plaque burden was evaluated in APP transgenic Tg2576 mice overexpressing Aβ. Antibody 2.1 is a murine surrogate for antibodies 1.1, 1.2 and 1.9, with similar binding avidity and affinity for Aβ monomers and fibrils as antibodies 1.1, 1.2 and 1.9.

Treatment: 9 month-old Tg2576 mice were treated weekly through i.p. route with murine monoclonal anti-Aβ 2.1 IgG in PBS at doses of 0 (started with 4 males, 6 females, 2 females died), 1.5 (started with 2 males, 8 females, 1 male and 1 female died), 4.5 (started with 4 males, 6 females, no death), 15 (started with 4 males, 6 females, 2 males and 1 female died), and 45 mg/kg (started with 4 males, 6 females, 1 male and 1 female died) in the volume of 5 ml/kg. The duration of treatment was 24 weeks. Blood samples (50-100 μl) were collected through tail vein at pre-dose, 4 hours after the 1st, 8th, 16th, 24th injections and one time just before the 24$^{th}$ injection, 6 time points in total. Seven days after the 24$^{th}$ injection, CSF and blood from cardiac puncture was collected.

Brain Dissection: All the animals were flushed with 5 ml of saline through the heart. The brain was then dissected out from the skull and bisected at the mid-line. Half of the brain was frozen on dry ice for future biochemical study and the other half was embedded in OCT tissue medium and then frozen on dry ice for histology studies.

Histology: 14 μm-thick fresh frozen coronal serial sections were cut in a cryostat microtome. Sections were thaw mounted onto the Fisher "plus" microscope slides and air-dried. Sections were stored at −20° C. until use. At the time of staining, sections were warmed to room temperature and fixed in 4% paraformaldehyde/0.1 M phosphate buffer, pH 7.2 for 1 hr. The endogenous tissue peroxidase activity was destroyed by incubating with 3% H$_2$O$_2$ in PBS for 20 min. Sections were then incubated with 88% formic acid for 20 min to expose Aβ epitope and then with blocking solution (3% normal goat serum/5% normal horse serum/0.25% carrageenan lambda/0.1% triton/PBS) for 1 hr. Sections were incubated with 0.5 μg/ml biotinylated anti-human Aβ monoclonal antibody 4G8 or a control mouse myeloma IgG (Sigma, St. Louis, Mo.) in the above blocking solution at 4° C. over night. The antigen was detected by ABC/DAB protocol as described (Yan et al., 1997). Sections were dehydrated and cover-slipped with mounting medium.

Morphological data analysis: Stained sections were examined under a light microscope. Digital images were taken under the microscope equipped with a digital camera. For amyloid plaque burden, the images were analyzed with Meta-Morph software (Universal Imaging Corp., West Chester, Pa.). Seven sections (1 out of every 5 serial sections) of each animal containing cingulate cortex (between Bregma 1.54 mm to −0.1 mm) (Franklin and Paxinos, 1997) and 8 sections of each animal containing hippocampus (between Bregma −1.7 mm to −2.8 mm) were used for the analysis. The area of interest was manually outlined under 4× magnification. The software was programmed to measure the numbers of plaques, the average size of plaques and the integrated plaque staining gray scale. The percentage of area covered by plaques was calculated by multiplying the number of plaques with the average size of plaques divided by the area of interest and time 100.

Data analysis: All the quantitative results were analyzed by one-way ANOVA test and followed by Donett t test.

FIGS. 2A-2D shows quantitative morphological analysis of the plaque burden in cingulate cortex. Only the treatment of 45 mg/k resulted in a significant reduction of plaque burden (50% reduction vs. PBS, p<0.05). The plaque burden in the hippocampus shows a trend of reduction with increased dosage of 2.1 treatment, but did not reach the statistically significant level.

Figure 3A:
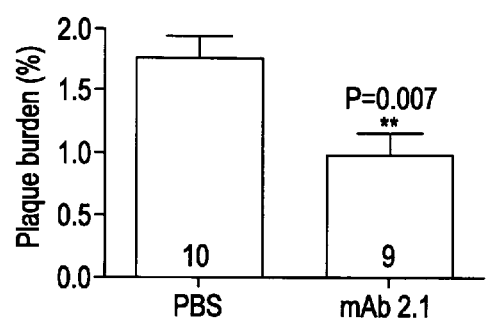
FIGS. 3A-3D illustrate quantitative morphological analysis of the plaque burden in cingulate cortex after treatment (3× per week) with mAb 2.1 IgG.
Figure 3B:
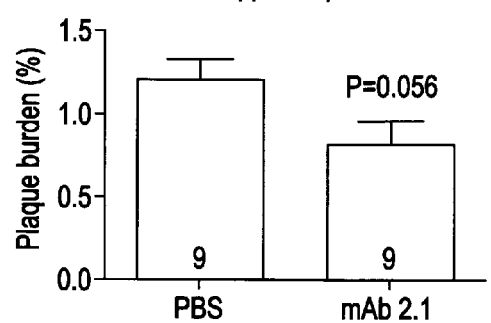
Figure 3C:
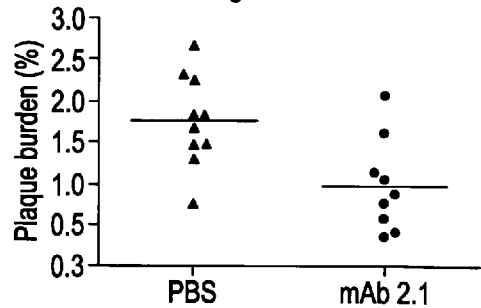
Figure 3D:
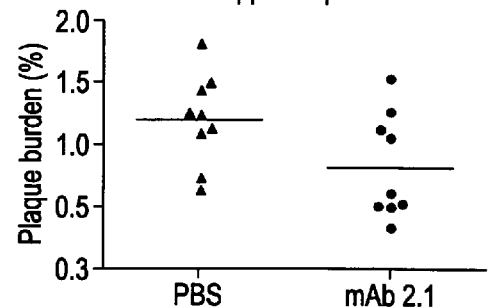

The above assay was repeated with a more frequent dosing regimen of 3× per week. Compared with PBS treatment, 1.5 mg/kg mAb 2.1 treatment resulted in a significant (p=0.007) 44% plaque burden reduction in the cingulate cortex (FIGS. 3A-3D). In these same animals, mAb 2.1 treatment resulted in 32% plaque burden reduction in the hippocampus but that did not reach statistical significance (p=0.056).

Example 9

Pharmacokinetic Study of Antibodies Following Single IV Dose Administration to Male Cynomolgus Monkeys The following Example characterizes the single-dose pharmacokinetics of monoclonal antibodies 1.1, 1.2 and 1.9 administered to male cynomolgus monkeys as an intravenous (IV) bolus injection.

A total of nine drug-naïve male cynomolgus monkeys (Vietnamese origin, 3.1-4.9 kg at time of dose administration) were obtained from Covance Laboratories, Inc. Madison, Wis. The animals were assigned to Groups 1, 2 or 3 based on body weight and received one of the three treatments set forth in Table 5 below.

TABLE 5

| Group No. | Antibodies | Route | Nominal Dose (mg/kg) | Target Dose Conc. (mg/mL) | Dose Volume (mL/kg) | n/group |
|---|---|---|---|---|---|---|
| 1 | 1.1 | IV | 4.5 | 3 | 1.5 | 3 |
| 2 | 1.2 | IV | 4.5 | 3 | 1.5 | 3 |
| 3 | 1.9 | IV | 4.5 | 3 | 1.5 | 3 |

Antibodies 1.1, 1.2 or 1.9 were administered as a single IV bolus injection at a dose of 4.5 mg/kg via the saphenous vein. Blood for determination of serum 1.1, 1.2 or 1.9 antibody concentrations was collected from each animal prior to dose administration and at 0.83, 0.25, 0.5, 1, 4, 8, 24, 48, 72, 120, 168, 240, 336, 504, 672, 840, 1172 and 1512 hours postdose. All blood samples were collected from the femoral vein. 1.1, 1.2 and 1.9 antibody concentrations in serum were quantified using a non-validated ELISA method. Pharmacokinetic analysis was conducted using noncompartmental methods.

Following intravenous bolus administration, the initial concentration at time zero ($C_0$) was estimated by back-extrapolation of the first two observed serum concentration values to time zero using linear/log regression. The initial volume of distribution ($V_0$) was calculated as IV dose/$C_0$. No noncompartmental analysis was conducted in one group 1 animal (antibody 1.1, 4.5 mg/kg), since $C_0$, and thus $V_0$, could not be determined due to the actual peak serum concentration which was observed at 8 hours postdose. The terminal phase rate constant ($\lambda_z$) was determined by linear regression of the natural logarithms of at least three or more measurable concentrations in the terminal phase. The terminal phase half-life ($t_{1/2,z}$) was calculated as $\ln(2)/\lambda_z$. The area under the serum concentration-time curve from time zero to the time of the last quantifiable concentration ($C_{last}$), $AUC_{0-t}$, was calculated using the linear/log trapezoidal method. The area under the serum concentration-time curve from the time of the last quantifiable concentration to infinity ($AUC_{t-inf}$) was estimated as predicted $C_{last}/\lambda_z$. The area under the serum concentration-time curve from time zero to infinity ($AUC_{0-inf}$) was calculated as $AUC_{0-t}+AUC_{t-inf}$. Systemic clearance (CL) was calculated as IV dose/$AUC_{0-inf}$. The volume of distribution at steady state ($V_{ss}$) was calculated as AUMC0-inf/AUC0-inf×CL, where $AUMC_{0-inf}$ is the area under the first moment curve from time zero to infinity.

Results: Following a single IV administration of antibody 1.1, 1.2 or 1.9 to monkeys, the antibody serum concentrations declined in a biphasic manner with an overall mean terminal phase half-life of 8, 10, and 7 days for antibodies 1.1, 1.2 and 1.9, respectively. See Table 6, below. The exposure (based on $C_0$ and $AUC_{0-inf}$) of the antibodies were ranked in the following order: antibody 1.2>antibody 1.9> and antibody 1.1. Because the dosage was administered intravenously, the $C_0$ is a surrogate for $C_{max}$.

TABLE 6

| Group | $C_0$ (μg/mL) | $AUC_{0-inf}$ (hr · μg/mL) | CL (mL/hr/kg) | $t_{1/2,z}$ (day) | $V_{ss}$ (mL/kg) | $V_0$ (mL/kg) |
|---|---|---|---|---|---|---|
| Antibody 1.1, n = 2 | | | | | | |
| 1 | 2.67 (NC) | 221 (NC) | 20.7 (NC) | 7.64 (NC) | 4470 (NC) | 1690 (NC) |
| Antibody 1.2, n = 3 | | | | | | |
| 2 | 84.0 (10.1) | 13200 (2370) | 0.350 (0.0662) | 9.61 (0.167) | 128 (8.48) | 54.1 (6.14) |
| Antibody 1.9, n = 2 | | | | | | |
| 3 | 36.4 (4.85) | 2430 (284) | 1.87 (0.230) | 7.25 (1.03) | 525 (80.2) | 125 (15.5) |

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. An isolated antibody that specifically binds to amyloid-beta 1-42 (Aβ42) with a dissociation rate constant ($k_d$) of about $1 \times 10^{-4}$ $s^{-1}$ or less as measured by surface plasmon resonance, and that comprises a light chain and a heavy chain, comprising:
   (a) a CDRL1 sequence as set forth in SEQ ID NO: 15;
   (b) a CDRL2 sequence as set forth in SEQ ID NO: 16;
   (c) a CDRL3 sequence as set forth in SEQ ID NO: 17;
   (d) a CDRH1 sequence as set forth in SEQ ID NO: 18;
   (e) a CDRH2 sequence as set forth in SEQ ID NO: 19; and
   (f) a CDRH3 sequence as set forth in SEQ ID NO: 20.

2. The antibody of claim 1, wherein said antibody comprises a heavy chain variable region comprising the amino acid sequence set forth in SEQ ID NO: 12 and a light chain variable region comprising the amino acid sequence set forth in SEQ ID NO: 14.

3. The antibody of any one of claims 1 or 2, wherein the antibody is of an IgA, IgG, IgE, IgD or IgM isotype.

4. The antibody of claim 3, wherein the antibody is an IgG antibody.

5. The antibody of claim 4, wherein the antibody is an IgG antibody and comprises two heavy chains and two light chains.

6. The antibody of claim 1, wherein the light chain comprises the amino acid sequence of amino acids 21-239 of SEQ ID NO:137.

7. The antibody of claim 1, wherein the heavy chain comprises the amino acid sequence of amino acids 20-470 of SEQ ID NO:139.

8. The antibody of claim 1, wherein the light chain comprises the amino acid sequence of amino acids 21-239 of SEQ ID NO:137 and the heavy chain comprises the amino acid sequence of amino acids 20-470 of SEQ ID NO:139.

9. The antibody of claim 3, wherein the antibody is an IgG antibody and is a single chain Fv antibody fragment, an Fab fragment, F(ab')$_2$ fragment, an Fd, a domain antibody (dAb), a diabody, a maxibody or a nanobody.

10. An isolated nucleic acid encoding the antibody of any of claims 1 or 2.

11. A vector comprising the nucleic acid of claim 10.

12. A host cell comprising the vector of claim 11.

13. A method of producing an antibody of claim 1 or 2, comprising culturing the host cell of claim 12 such that the nucleic acid is expressed to produce the antibody.

14. The method of claim 13, further comprising the step of recovering the antibody from the host cell culture.

15. A method of treating a neurodegenerative or CNS disorder associated with amyloid-beta in a mammal by administering to said mammal a therapeutically effective amount of the antibody of any of claims 1 or 2.

16. A method of treating an amyloidogenic disease in a mammal by administering to said mammal a therapeutically effective amount of the antibody of any of claim 1 or 2.

17. The method of claim 16, wherein the amyloidogenic disease is selected from the group consisting of Alzheimer's disease (AD), mild cognitive impairment, Parkinson's Disease with dementia, Down's Syndrome, Diffuse Lewy Body (DLB) disease, Cerebral Amyloid Angiopathy (CAA), vascular dementia, and mixed dementia.

18. The method of claim 16, wherein the mammal is human.

19. The method of claim 16, wherein the administering is performed intrathecally.

20. A pharmaceutical composition, comprising the antibody of claim 1 or claim 2, and a pharmaceutically acceptable carrier.

* * * * *

UNITED STATES PATENT AND TRADEMARK OFFICE
CERTIFICATE OF CORRECTION

PATENT NO. : 8,414,893 B2  
APPLICATION NO. : 12/809563  
DATED : April 9, 2013  
INVENTOR(S) : Biere-Citron et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Thirtieth Day of September, 2014

Michelle K. Lee
*Deputy Director of the United States Patent and Trademark Office*

SEQUENCE LISTING

<160> NUMBER OF SEQ ID NOS: 170

<210> SEQ ID NO 1
<211> LENGTH: 357
<212> TYPE: DNA
<213> ORGANISM: Homo sapiens

<400> SEQUENCE: 1
caggtcacct tgaaggagtc tggtcctgtg ctggtgaaac ccacagagac cctcacgctg      60
acctgcaccg tctctgggtt ctcactcagc aatgctagaa tgagtgtgag ctggatccgt     120
cagcccccag ggaaggccct ggagtggctt gcacacattt tttcgaatga cgaaaaatcc     180
tacagcacat ctctgaagag caggctcacc atctccaagg acacctccaa aagccaggtg     240
gtccttacca tgaccaacat ggaccctgtg acacagcca catattactg tgcacggatc      300
cggggtacgg tgggttatga ctactggggc cagggaaccc tggtcaccgt ctcctca        357

<210> SEQ ID NO 2
<211> LENGTH: 119
<212> TYPE: PRT
<213> ORGANISM: Homo sapiens

<400> SEQUENCE: 2

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Ser Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Arg Gly Thr Val Gly Tyr Asp Tyr Trp Gly Gln Gly
            100                 105                 110

Thr Leu Val Thr Val Ser Ser
        115

<210> SEQ ID NO 3
<211> LENGTH: 336
<212> TYPE: DNA
<213> ORGANISM: Homo sapiens

<400> SEQUENCE: 3
gatattgtga tgacccagac tccactctcc tcacctgtca cccttggaca gccggcctcc      60
atctcctgca ggtctagtca aagcctcgta cacagtgatg aaacaccta cttgagttgg      120 cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tactactgca tgcaaattac acaatttcct     300
ctcactttcg gcggagggac caaggtggag atcaaa                              336

<210> SEQ ID NO 4
<211> LENGTH: 112
<212> TYPE: PRT

-continued

<213> ORGANISM: Homo sapiens

<400> SEQUENCE: 4

```
Asp Ile Val Met Thr Gln Thr Pro Leu Ser Pro Val Thr Leu Gly
1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ile
                85                  90                  95

Thr Gln Phe Pro Leu Thr Phe Gly Gly Gly Thr Lys Val Glu Ile Lys
            100                 105                 110
```

<210> SEQ ID NO 5
<211> LENGTH: 16
<212> TYPE: PRT
<213> ORGANISM: Homo sapiens

<400> SEQUENCE: 5

```
Arg Ser Ser Gln Ser Leu Val His Ser Asp Gly Asn Thr Tyr Leu Ser
1               5                  10                  15
```

<210> SEQ ID NO 6
<211> LENGTH: 7
<212> TYPE: PRT
<213> ORGANISM: Homo sapiens

<400> SEQUENCE: 6

```
Lys Ile Ser Asn Arg Phe Ser
1               5
```

<210> SEQ ID NO 7
<211> LENGTH: 9
<212> TYPE: PRT
<213> ORGANISM: Homo sapiens

<400> SEQUENCE: 7

```
Met Gln Ile Thr Gln Phe Pro Leu Thr
1               5
```

<210> SEQ ID NO 8
<211> LENGTH: 7
<212> TYPE: PRT
<213> ORGANISM: Homo sapiens

<400> SEQUENCE: 8

```
Asn Ala Arg Met Ser Val Ser
1               5
```

<210> SEQ ID NO 9
<211> LENGTH: 16
<212> TYPE: PRT
<213> ORGANISM: Homo sapiens

<400> SEQUENCE: 9

```
His Ile Phe Ser Asn Asp Glu Lys Ser Tyr Ser Thr Ser Leu Lys Ser
1               5                  10                  15
```

<210> SEQ ID NO 10
<211> LENGTH: 8
<212> TYPE: PRT
<213> ORGANISM: Homo sapiens

<400> SEQUENCE: 10

Arg Gly Thr Val Gly Tyr Asp Tyr
1               5

<210> SEQ ID NO 11
<211> LENGTH: 363
<212> TYPE: DNA
<213> ORGANISM: Homo sapiens

<400> SEQUENCE: 11

```
caggtcacct tgaaggagtc tggtcctgtg ctgctgaaac ccacagagac cctcacgctg      60
acctgcaccg tctctgggtt ctcactcagc aatgctagaa tgggtgtgag ctggatccgt     120
cagcccccag ggaaggccct ggagtggctt gcacacattt tttcgaatga cgaaaaatcc     180
tacatcacat ctctgaagag caggctcacc atctccaagg acacctccaa aagccaggtg     240
gtccttacca tgaccaacat ggaccctgtg acacagcca catattactg tgcacgata      300 cccctacgat ccccgggtgc ttttgatatc tggggccaag ggacaatggt caccgtctct     360
tca                                                                    363
```

<210> SEQ ID NO 12
<211> LENGTH: 121
<212> TYPE: PRT
<213> ORGANISM: Homo sapiens

<400> SEQUENCE: 12

Gln Val Thr Leu Lys Glu Ser Gly Pro Val Leu Leu Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ile Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Thr Ala Thr Tyr Tyr
                85                  90                  95

Cys Ala Arg Ile Pro Leu Arg Ser Pro Gly Ala Phe Asp Ile Trp Gly
            100                 105                 110

Gln Gly Thr Met Val Thr Val Ser Ser
        115                 120

<210> SEQ ID NO 13
<211> LENGTH: 336
<212> TYPE: DNA
<213> ORGANISM: Homo sapiens

<400> SEQUENCE: 13

```
gatattgtga tgacccagac tccactctcc tcacctgtca cccttggaca gccggcctcc      60
atctcctgca ggtctagtca aagcctcgta cacagtgatg gaaacaccta cttgaattgg     120
cttcagcaga ggccaggcca gcctccaaga ctcctaattt ataagatttc taaccggttc     180
tctggggtcc cagacagatt cactggcagt ggggcaggga cagatttcac actgaaaatc     240
```

```
agcagggtgg aagctgagga tgtcggggtt tatacctgca tgcaagttac acaatttcct    300
ctcaccttcg gccaagggac acgactggag attaaa                              336
```

<210> SEQ ID NO 14
<211> LENGTH: 112
<212> TYPE: PRT
<213> ORGANISM: Homo sapiens

<400> SEQUENCE: 14

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Thr Gly Ser Gly Ala Gly Thr Asp Phe Thr Leu Lys Ile
65                  70                  75                  80

Ser Arg Val Glu Ala Glu Asp Val Gly Val Tyr Thr Cys Met Gln Val
                85                  90                  95

Thr Gln Phe Pro Leu Thr Phe Gly Gln Gly Thr Arg Leu Glu Ile Lys
            100                 105                 110
```

<210> SEQ ID NO 15
<211> LENGTH: 16
<212> TYPE: PRT
<213> ORGANISM: Homo sapiens

<400> SEQUENCE: 15

```
Arg Ser Ser Gln Ser Leu Val His Ser Asp Gly Asn Thr Tyr Leu Asn
1               5                   10                  15
```

<210> SEQ ID NO 16
<211> LENGTH: 7
<212> TYPE: PRT
<213> ORGANISM: Homo sapiens

<400> SEQUENCE: 16

```
Lys Ile Ser Asn Arg Phe Ser
1               5
```

<210> SEQ ID NO 17
<211> LENGTH: 9
<212> TYPE: PRT
<213> ORGANISM: Homo sapiens

<400> SEQUENCE: 17

```
Met Gln Val Thr Gln Phe Pro Leu Thr
1               5
```

<210> SEQ ID NO 18
<211> LENGTH: 7
<212> TYPE: PRT
<213> ORGANISM: Homo sapiens

<400> SEQUENCE: 18

```
Asn Ala Arg Met Gly Val Ser
1               5
```

<210> SEQ ID NO 19

```
<211> LENGTH: 16
<212> TYPE: PRT
<213> ORGANISM: Homo sapiens

<400> SEQUENCE: 19

His Ile Phe Ser Asn Asp Glu Lys Ser Tyr Ile Thr Ser Leu Lys Ser
1               5                   10                  15

<210> SEQ ID NO 20
<211> LENGTH: 10
<212> TYPE: PRT
<213> ORGANISM: Homo sapiens

<400> SEQUENCE: 20

Pro Leu Arg Ser Pro Gly Ala Phe Asp Ile
1               5                   10

<210> SEQ ID NO 21
<211> LENGTH: 357
<212> TYPE: DNA
<213> ORGANISM: Homo sapiens

<400> SEQUENCE: 21
caggtcacct tgaaggagtc tggtcctgtg ctggtgaaac ccacagagac cctcacgctg      60
acctgcaccg tctctgggtt ctcactcagc aatgctagaa tgagtgtgag ctggatccgt     120
cagcccccag ggaaggccct ggagtggctt gcacacattt tttcgaatga cgaaaaatcc     180
tacagcacat ctctgaagag caggctcacc atctccaagg acacctccaa aagccaggtg     240
gtccttacca tgaccaacat ggaccctgtg gacacagcca catattactg tgcacggatc     300
cggggtacgg tgggttttga ctactggggc cagggaaccc tggtcaccgt ctcctca       357

<210> SEQ ID NO 22
<211> LENGTH: 119
<212> TYPE: PRT
<213> ORGANISM: Homo sapiens

<400> SEQUENCE: 22

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Ser Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
        50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Arg Gly Thr Val Gly Phe Asp Tyr Trp Gly Gln Gly
            100                 105                 110

Thr Leu Val Thr Val Ser Ser
        115

<210> SEQ ID NO 23
<211> LENGTH: 336
<212> TYPE: DNA
<213> ORGANISM: Homo sapiens

<400> SEQUENCE: 23
```

```
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tactactgca tgcaagttac acaatttcct     300
ctcactttcg gcggagggac caaggtggag atcaaa                               336
```

<210> SEQ ID NO 24
<211> LENGTH: 112
<212> TYPE: PRT
<213> ORGANISM: Homo sapiens

<400> SEQUENCE: 24

Asp Ile Val Met Thr Gln Thr Pro Leu Ser Ser Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Thr Gln Phe Pro Leu Thr Phe Gly Gly Gly Thr Lys Val Glu Ile Lys
            100                 105                 110

<210> SEQ ID NO 25
<211> LENGTH: 16
<212> TYPE: PRT
<213> ORGANISM: Homo sapiens

<400> SEQUENCE: 25

Arg Ser Ser Gln Ser Leu Val His Ser Asp Gly Asn Thr Tyr Leu Ser
1               5                   10                  15

<210> SEQ ID NO 26
<211> LENGTH: 7
<212> TYPE: PRT
<213> ORGANISM: Homo sapiens

<400> SEQUENCE: 26

Lys Ile Ser Asn Arg Phe Ser
1               5

<210> SEQ ID NO 27
<211> LENGTH: 9
<212> TYPE: PRT
<213> ORGANISM: Homo sapiens

<400> SEQUENCE: 27

Met Gln Val Thr Gln Phe Pro Leu Thr
1               5

<210> SEQ ID NO 28
<211> LENGTH: 7
<212> TYPE: PRT
<213> ORGANISM: Homo sapiens

<400> SEQUENCE: 28

Asn Ala Arg Met Ser Val Ser
1               5

<210> SEQ ID NO 29
<211> LENGTH: 16
<212> TYPE: PRT
<213> ORGANISM: Homo sapiens

<400> SEQUENCE: 29

His Ile Phe Ser Asn Asp Glu Lys Ser Tyr Ser Thr Ser Leu Lys Ser
1               5                   10                  15

<210> SEQ ID NO 30
<211> LENGTH: 8
<212> TYPE: PRT
<213> ORGANISM: Homo sapiens

<400> SEQUENCE: 30

Arg Gly Thr Val Gly Phe Asp Tyr
1               5

<210> SEQ ID NO 31
<211> LENGTH: 363
<212> TYPE: DNA
<213> ORGANISM: Homo sapiens

<400> SEQUENCE: 31
caggtcacct tgaaggagtc tggtcctgtg ctggtgaaac ccacagagac cctcacgctg     60
acctgcaccg tctctgggtt ctcactcagc aatgctagaa tgggtgtgag ctggatccgt    120
cagcccccag ggaaggccct ggagtggctt gcacacattt tttcgaatga cgaaaaatcc    180
tacagcacat ctctgaagag caggctcacc atctccaagg acaccttcaa aagccaggtg    240
gtccttacca tgaccaacat ggaccctgtg gacacagcca catattactg tgcacggata    300
cccctacgat ccccgggtgc ttttgatatc tggggccaag ggacaatggt caccgtctct    360
tca                                                                  363

<210> SEQ ID NO 32
<211> LENGTH: 121
<212> TYPE: PRT
<213> ORGANISM: Homo sapiens

<400> SEQUENCE: 32

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Phe Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Pro Leu Arg Ser Pro Gly Ala Phe Asp Ile Trp Gly
            100                 105                 110

Gln Gly Thr Met Val Thr Val Ser Ser
        115                 120

<210> SEQ ID NO 33
<211> LENGTH: 336
<212> TYPE: DNA
<213> ORGANISM: Homo sapiens

<400> SEQUENCE: 33

```
gaaattgtga tgacccagac tccactctcc tcacctgtca cccttggaca gccggcctcc      60
atctcctgca ggtctagtca aagcctcgta cacagtgatc gaaacaccta cttgagttgg     120
cttcagcaga ggccaggcca gcctccaaga ctcctcattt ataagatttc taaccgattc     180
tctggggtcc cagacagatt cagtggcagt ggggcaggga cagatttcac actgaaaatc     240
agcagggtgg aggctgagga tgtcggggtt tattactgca tgcaaactac acaacttcct     300
ctcactttcg gccaagggc acgactggag attaaa                                336
```

<210> SEQ ID NO 34
<211> LENGTH: 112
<212> TYPE: PRT
<213> ORGANISM: Homo sapiens

<400> SEQUENCE: 34

```
Glu Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Leu Pro Leu Thr Phe Gly Gln Gly Ala Arg Leu Glu Ile Lys
            100                 105                 110
```

<210> SEQ ID NO 35
<211> LENGTH: 16
<212> TYPE: PRT
<213> ORGANISM: Homo sapiens

<400> SEQUENCE: 35

```
Arg Ser Ser Gln Ser Leu Val His Ser Asp Arg Asn Thr Tyr Leu Ser
1               5                   10                  15
```

<210> SEQ ID NO 36
<211> LENGTH: 7
<212> TYPE: PRT
<213> ORGANISM: Homo sapiens

<400> SEQUENCE: 36

```
Lys Ile Ser Asn Arg Phe Ser
1               5
```

<210> SEQ ID NO 37
<211> LENGTH: 9
<212> TYPE: PRT
<213> ORGANISM: Homo sapiens

<400> SEQUENCE: 37

```
Met Gln Thr Thr Gln Leu Pro Leu Thr
1               5

<210> SEQ ID NO 38
<211> LENGTH: 7
<212> TYPE: PRT
<213> ORGANISM: Homo sapiens

<400> SEQUENCE: 38

Asn Ala Arg Met Gly Val Ser
1               5

<210> SEQ ID NO 39
<211> LENGTH: 16
<212> TYPE: PRT
<213> ORGANISM: Homo sapiens

<400> SEQUENCE: 39

His Ile Phe Ser Asn Asp Glu Lys Ser Tyr Ser Thr Ser Leu Lys Ser
1               5                   10                  15

<210> SEQ ID NO 40
<211> LENGTH: 10
<212> TYPE: PRT
<213> ORGANISM: Homo sapiens

<400> SEQUENCE: 40

Pro Leu Arg Ser Pro Gly Ala Phe Asp Ile
1               5                   10

<210> SEQ ID NO 41
<211> LENGTH: 16
<212> TYPE: PRT
<213> ORGANISM: Homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 41

His Ile Phe Ser Asn Asp Glu Lys Ser Tyr Xaa Thr Ser Leu Lys Ser
1               5                   10                  15

<210> SEQ ID NO 42
<211> LENGTH: 7
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 42

Asn Ala Arg Met Xaa Val Ser
1               5

<210> SEQ ID NO 43
<211> LENGTH: 43
<212> TYPE: PRT
<213> ORGANISM: Homo sapiens

<400> SEQUENCE: 43

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

-continued

Gly Leu Met Val Gly Gly Val Val Ile Ala Thr
         35                  40

<210> SEQ ID NO 44
<211> LENGTH: 723
<212> TYPE: DNA
<213> ORGANISM: Homo sapiens

<400> SEQUENCE: 44
atggacatga ggctccctgc tcagctcctg gggctgctaa tgctctgggt cccaggatcc    60
agtggggatg ttctgatgac tcagtctcca ctctccctgc ccgtcaccct tggacagccg   120
gcctccatct cctgcaggtc tagtcaaagc atcgtacaca gtaacggaaa cacctacttg   180
gagtggtatc tgcagaggcc aggccaatct ccaaagctcc taatttataa ggtttctaac   240
cggttctctg ggtcccaga cagattcagc ggcagtgggt caggcactga tttcacactg   300
aaaatcagca gggtggaggc tgaggatgtt ggggtttatt actgcttcca aggtagccac   360
gttcctctga cgtcggcgc agggaccaag ctggaaatca acggactgt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                  723

<210> SEQ ID NO 45
<211> LENGTH: 241
<212> TYPE: PRT
<213> ORGANISM: Homo sapiens

<400> SEQUENCE: 45

Met Asp Met Arg Leu Pro Ala Gln Leu Leu Gly Leu Leu Met Leu Trp
1               5                   10                  15
Val Pro Gly Ser Ser Gly Asp Val Leu Met Thr Gln Ser Pro Leu Ser
            20                  25                  30
Leu Pro Val Thr Leu Gly Gln Pro Ala Ser Ile Ser Cys Arg Ser Ser
        35                  40                  45
Gln Ser Ile Val His Ser Asn Gly Asn Thr Tyr Leu Glu Trp Tyr Leu
    50                  55                  60
Gln Arg Pro Gly Gln Ser Pro Lys Leu Leu Ile Tyr Lys Val Ser Asn
65                  70                  75                  80
Arg Phe Ser Gly Val Pro Asp Arg Phe Ser Gly Ser Gly Ser Gly Thr
                85                  90                  95
Asp Phe Thr Leu Lys Ile Ser Arg Val Glu Ala Glu Asp Val Gly Val
            100                 105                 110
Tyr Tyr Cys Phe Gln Gly Ser His Val Pro Leu Thr Phe Gly Ala Gly
        115                 120                 125
Thr Lys Leu Glu Ile Lys Arg Thr Val Ala Ala Pro Ser Val Phe Ile
    130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
        210                 215                 220

His Gln Gly Leu Ser Ser Pro Val Thr Lys Ser Phe Asn Arg Gly Glu
225                 230                 235                 240

Cys

<210> SEQ ID NO 46
<211> LENGTH: 1410
<212> TYPE: DNA
<213> ORGANISM: Homo sapiens

<400> SEQUENCE: 46

| | |
|---|---:|
| atggacacac tttgctccac gctcctgctg ctgaccatcc cttcatgggt cttgtcccag | 60 |
| gtcaccttga aggagtctgg tcctgcgctg gtgaaaccca cacagaccct cacgctgacc | 120 |
| tgcaccttct ctgggttctc actccgcact agtggaatgg gcgtgggctg gatccgtcag | 180 |
| cccccaggaa aggccctgga gtggcttgcc cacatttggt gggatgatga aaagagctac | 240 |
| aacccatctc tgaagagcca gctcaccatc tctaaggaca cctccaaaaa ccaggtggtc | 300 |
| cttacaatga ccaacatgga ccctgtggac acagccacat attactgtgc acgcagaaac | 360 |
| tattactacg acgactactt cgcctactgg ggccagggca ccctggtcac cgtctctagt | 420 |
| gcctccacca agggcccatc ggtcttcccc ctggcaccct cctccaagag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagaa agttgagccc | 720 |
| aaatcttgtg acaaaactca cacatgccca ccgtgcccag cacctgaact cctgggggga | 780 |
| ccgtcagtct tcctcttccc cccaaaaccc aaggacaccc tcatgatctc ccggacccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag ggcagccccg agaaccacag gtgtacaccc tgcccccatc ccgggatgag | 1140 |
| ctgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctat agcaagctca ccgtggacaa gagcaggtgg | 1320 |
| cagcagggga acgtcttctc atgctccgtg atgcatgagg ctctgcacaa ccactacacg | 1380 |
| cagaagagcc tctccctgtc tccgggtaaa | 1410 |

<210> SEQ ID NO 47
<211> LENGTH: 470
<212> TYPE: PRT
<213> ORGANISM: Homo sapiens

<400> SEQUENCE: 47

Met Asp Thr Leu Cys Ser Thr Leu Leu Leu Thr Ile Pro Ser Trp
1               5                   10                  15

Val Leu Ser Gln Val Thr Leu Lys Glu Ser Gly Pro Ala Leu Val Lys

```
                    20                  25                  30
Pro Thr Gln Thr Leu Thr Leu Thr Cys Thr Phe Ser Gly Phe Ser Leu
                35                  40                  45
Arg Thr Ser Gly Met Gly Val Gly Trp Ile Arg Gln Pro Pro Gly Lys
            50                  55                  60
Ala Leu Glu Trp Leu Ala His Ile Trp Trp Asp Asp Lys Ser Tyr
65                  70                  75                  80
Asn Pro Ser Leu Lys Ser Gln Leu Thr Ile Ser Lys Thr Ser Lys
                85                  90                  95
Asn Gln Val Val Leu Thr Met Thr Asn Met Asp Pro Val Asp Thr Ala
                100                 105                 110
Thr Tyr Tyr Cys Ala Arg Arg Asn Tyr Tyr Asp Asp Tyr Phe Ala
            115                 120                 125
Tyr Trp Gly Gln Gly Thr Leu Val Thr Val Ser Ser Ala Ser Thr Lys
            130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
            210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
            290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Asp Glu Leu Thr Lys Asn
            370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
            435                 440                 445
```

Ser Val Met His Glu Ala Leu His Asn His Tyr Thr Gln Lys Ser Leu
            450                 455                 460

Ser Leu Ser Pro Gly Lys
465                 470

<210> SEQ ID NO 48
<211> LENGTH: 714
<212> TYPE: DNA
<213> ORGANISM: Mus musculus

<400> SEQUENCE: 48
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcagat ctagtcagag cattgtacat agtaatggaa acacctattt agaatggtac   180
ctgcagaaac aggccagtc tccaaagctc ctgatctaca agtttccaa ccgatttct    240 ggggtcccag acaggttcag tggcagtgga tcaggacag atttcacact caagatcagc   300
agagtggagg ctgaggatct gggagtttat tactgctttc aaggttcaca tgttccgctc   360
acgttcggtg ctgggaccaa gctggagctg aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660 actcacaaga catcaacttc acccattgtc aagagcttca caggaatga gtgt          714

<210> SEQ ID NO 49
<211> LENGTH: 238
<212> TYPE: PRT
<213> ORGANISM: Mus musculus

<400> SEQUENCE: 49

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Leu Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser 180                 185                 190
Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
        210                 215                 220

Ser Thr Ser Pro Ile Val Lys Ser Phe Asn Arg Asn Glu Cys
225                 230                 235

<210> SEQ ID NO 50
<211> LENGTH: 1392
<212> TYPE: DNA
<213> ORGANISM: Mus musculus

<400> SEQUENCE: 50

```
atggacaggc ttacttcctc attcctgctg ctgattgtcc ctgcatatgt cttgtcccaa     60
gttactctaa aagagtctgg ccctgggata ttgaagccct cacagaccct cagtctgact    120
tgttctttct ctgggttttc actgagaact tctggtatgg gtgtaggctg gattcgtcag    180
ccttcaggga agggtctgga gtggctggca cacatttggt gggatgatga taagtcctat    240
aacccatccc tgaagagcca gctcacaatc tccaaggata cctccagaaa ccaggtattc    300
ctcaagatca ccagtgtgga cactgcagat actgccactt actactgtgc tcgaaggaac    360
tattattacg acgactactt tgcctactgg ggccaaggca ccactctcac agtctcctca    420
gccaaaacga cacccccatc tgtctatcca ctggcccctg gatctgctgc ccaaactaac    480
tccatggtga ccctgggatg cctggtcaag ggctatttcc ctgagccagt gacagtgacc    540
tggaactctg gatccctgtc cagcggtgtg cacaccttcc cagctgtcct gcagtctgac    600
ctctacactc tgagcagctc agtgactgtc cctccagcac ctggcccag cgagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc ccaaggatgt gctcaccatt actctgactc ctaaggtcac gtgtgttgtg    840
gtagacatca gcaaggatga tcccgaggtc cagttcagct ggtttgtaga tgatgtggag    900
gtgcacacag ctcagacgca accccgggag gagcagttca acagcacttt ccgctcagtc    960
agtgaacttc ccatcatgca tcaggactgg ctcaatggca aggagttcaa atgcagggtc   1020
aacagtgcag ctttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc cagcggagaa ctacaagaac actcagccca tcatggacac agatggctct   1260
tacttcgtct acagcaagct caatgtgcag aagagcaact gggaggcagg aaatactttc   1320
acctgctctg tgttacatga gggcctgcac aaccaccata tgagaagag cctctcccac   1380
tctcctggta aa                                                      1392
```

<210> SEQ ID NO 51
<211> LENGTH: 464
<212> TYPE: PRT
<213> ORGANISM: Mus musculus

<400> SEQUENCE: 51

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
            20                  25                  30

```
Pro Ser Gln Thr Leu Ser Leu Thr Cys Ser Phe Ser Gly Phe Ser Leu
            35                  40                  45

Arg Thr Ser Gly Met Gly Val Gly Trp Ile Arg Gln Pro Ser Gly Lys
 50                  55                  60

Gly Leu Glu Trp Leu Ala His Ile Trp Trp Asp Asp Lys Ser Tyr
 65                  70                  75                  80

Asn Pro Ser Leu Lys Ser Gln Leu Thr Ile Ser Lys Asp Thr Ser Arg
                    85                  90                  95

Asn Gln Val Phe Leu Lys Ile Thr Ser Val Asp Thr Ala Asp Thr Ala
                100                 105                 110

Thr Tyr Tyr Cys Ala Arg Arg Asn Tyr Tyr Asp Asp Tyr Phe Ala
            115                 120                 125

Tyr Trp Gly Gln Gly Thr Thr Leu Thr Val Ser Ala Lys Thr Thr
        130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
            195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
                260                 265                 270

Thr Pro Lys Val Thr Cys Val Val Asp Ile Ser Lys Asp Asp Pro
    275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
                340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
```

<210> SEQ ID NO 52
<211> LENGTH: 378
<212> TYPE: DNA
<213> ORGANISM: Homo sapiens

<400> SEQUENCE: 52

```
gaggtgcagc tggtggagtc tgggggaggc ttggtacagc ctgggggtc cctgagactc      60
tcctgtgcag cctctggatt caccttcagt agctatagca tgaactgggt ccgccaggct    120
ccagggaagg gctggagtg gtttcatac attagtagaa gtagtagtgc catatactac    180
gcagactctg tgaagggccg attcaccatc tccagagaca atgccaagaa ttcactgtat    240
ctgcaaatga acagcctgag agacgaggac acggctgtgt attactgtgc gagagagact    300
acagtaacta cgaggttta ctactactac tacggtgtgg acgtctgggg ccaagggacc    360
acggtcaccg tctcctca                                                  378
```

<210> SEQ ID NO 53
<211> LENGTH: 126
<212> TYPE: PRT
<213> ORGANISM: Homo sapiens

<400> SEQUENCE: 53

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Tyr Ile Ser Arg Ser Ser Ser Ala Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Asp Glu Asp Thr Ala Val Tyr Tyr Cys
                85                  90                  95
Ala Arg Glu Thr Thr Val Thr Thr Arg Phe Tyr Tyr Tyr Tyr Gly
            100                 105                 110
Val Asp Val Trp Gly Gln Gly Thr Thr Val Thr Val Ser Ser
        115                 120                 125

<210> SEQ ID NO 54
<211> LENGTH: 321
<212> TYPE: DNA
<213> ORGANISM: Homo sapiens

<400> SEQUENCE: 54

```
gacatccaga tgacccagtc tccatcttcc gtgtctgcat ctgtaggaga cagagtcacc     60
atcacttgtc gggcgagtca gggtattagt agctggttag cctggtttca gcagaaacca   120
gggaaagccc ctaagctcct gatctatgct gcatctagtt tgcaaagtgg ggtcccctca   180
aggttcagcg gcagtggatc tgggacagat ttcactctca ccatcagcag cctgcagcct   240
gaagattttg caacttacta ttgtcaacag gctaacagtt tccctcggac gttcggccaa   300
gggaccaagg tggaaatcaa a                                             321
```

<210> SEQ ID NO 55
<211> LENGTH: 107
<212> TYPE: PRT

<213> ORGANISM: Homo sapiens

<400> SEQUENCE: 55

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 56
<211> LENGTH: 11
<212> TYPE: PRT
<213> ORGANISM: Homo sapiens

<400> SEQUENCE: 56

Arg Ala Ser Gln Gly Ile Ser Ser Trp Leu Ala
1               5                   10

<210> SEQ ID NO 57
<211> LENGTH: 7
<212> TYPE: PRT
<213> ORGANISM: Homo sapiens

<400> SEQUENCE: 57

Ala Ala Ser Ser Leu Gln Ser
1               5

<210> SEQ ID NO 58
<211> LENGTH: 9
<212> TYPE: PRT
<213> ORGANISM: Homo sapiens

<400> SEQUENCE: 58

Gln Gln Ala Asn Ser Phe Pro Arg Thr
1               5

<210> SEQ ID NO 59
<211> LENGTH: 5
<212> TYPE: PRT
<213> ORGANISM: Homo sapiens

<400> SEQUENCE: 59

Ser Tyr Ser Met Asn
1               5

<210> SEQ ID NO 60
<211> LENGTH: 17
<212> TYPE: PRT
<213> ORGANISM: Homo sapiens

<400> SEQUENCE: 60

Tyr Ile Ser Arg Ser Ser Ala Ile Tyr Tyr Ala Asp Ser Val Lys
1               5                   10                  15

Gly

```
<210> SEQ ID NO 61
<211> LENGTH: 17
<212> TYPE: PRT
<213> ORGANISM: Homo sapiens

<400> SEQUENCE: 61
```

Glu Thr Thr Val Thr Thr Arg Phe Tyr Tyr Tyr Tyr Gly Val Asp
1               5                   10                  15

Val

```
<210> SEQ ID NO 62
<211> LENGTH: 363
<212> TYPE: DNA
<213> ORGANISM: Homo sapiens

<400> SEQUENCE: 62
```

| | |
|---|---|
| gaggtgcagc tgttggagtc tgggggaggc ttggtacagc ctggggggtc cctgagactc | 60 |
| tcctgtgcag cctctggatt cacctttagc agctatgcca tgagctgggt ccgccaggct | 120 |
| ccagggaagg ggctggagtg ggtctcagct attagtggtc gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtat attactgtgc gaaagatcgg | 300 |
| ggtcttacta aggttcgggg ctttgactac tggggccagg gaaccctggt caccgtctcc | 360 |
| tca | 363 |

```
<210> SEQ ID NO 63
<211> LENGTH: 121
<212> TYPE: PRT
<213> ORGANISM: Homo sapiens

<400> SEQUENCE: 63
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Thr Lys Val Arg Gly Phe Asp Tyr Trp Gly
            100                 105                 110

Gln Gly Thr Leu Val Thr Val Ser Ser
        115                 120

```
<210> SEQ ID NO 64
<211> LENGTH: 342
<212> TYPE: DNA
<213> ORGANISM: Homo sapiens

<400> SEQUENCE: 64
```

| | |
|---|---|
| gatgttgtga tgactcagtc tccattctcc ctgcccgtca cccttggaca gccggcctcc | 60 |
| atctcctgca ggtctagtca aagcctcgtg tacagtgatg gaaacaccct cttgaattgg | 120 | tttcagcaga ggccaggcca atctccaagg cgcctcattt ataaggtttc taagtgggac    180 tctggggtcc cagacagatt cagcggcagt gggtcaggca ctgatttcac actgaaaatc    240 agcagggtgg aggctgagga tgttgggggtt tattactgca tgcaaggtac acactggcct    300 cggggattta ctttcggccc tgggaccaaa gtggatatca aa                       342

<210> SEQ ID NO 65
<211> LENGTH: 114
<212> TYPE: PRT
<213> ORGANISM: Homo sapiens

<400> SEQUENCE: 65

Asp Val Val Met Thr Gln Ser Pro Phe Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Ser Leu Asn Trp Phe Gln Gln Arg Pro Gly Gln Ser
        35                  40                  45

Pro Arg Arg Leu Ile Tyr Lys Val Ser Lys Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Gly Phe Thr Phe Gly Pro Gly Thr Lys Val Asp
            100                 105                 110

Ile Lys

<210> SEQ ID NO 66
<211> LENGTH: 16
<212> TYPE: PRT
<213> ORGANISM: Homo sapiens

<400> SEQUENCE: 66

Arg Ser Ser Gln Ser Leu Val Tyr Ser Asp Gly Asn Thr Ser Leu Asn
1               5                   10                  15

<210> SEQ ID NO 67
<211> LENGTH: 7
<212> TYPE: PRT
<213> ORGANISM: Homo sapiens

<400> SEQUENCE: 67

Lys Val Ser Lys Trp Asp Ser
1               5

<210> SEQ ID NO 68
<211> LENGTH: 11
<212> TYPE: PRT
<213> ORGANISM: Homo sapiens

<400> SEQUENCE: 68

Met Gln Gly Thr His Trp Pro Arg Gly Phe Thr
1               5                   10

<210> SEQ ID NO 69
<211> LENGTH: 5
<212> TYPE: PRT
<213> ORGANISM: Homo sapiens

<400> SEQUENCE: 69

```
Ser Tyr Ala Met Ser
1               5
```

<210> SEQ ID NO 70
<211> LENGTH: 17
<212> TYPE: PRT
<213> ORGANISM: Homo sapiens

<400> SEQUENCE: 70

```
Ala Ile Ser Gly Arg Gly Gly Ser Thr Tyr Tyr Ala Asp Ser Val Lys
1               5                   10                  15

Gly
```

<210> SEQ ID NO 71
<211> LENGTH: 12
<212> TYPE: PRT
<213> ORGANISM: Homo sapiens

<400> SEQUENCE: 71

```
Asp Arg Gly Leu Thr Lys Val Arg Gly Phe Asp Tyr
1               5                   10
```

<210> SEQ ID NO 72
<211> LENGTH: 378
<212> TYPE: DNA
<213> ORGANISM: Homo sapiens

<400> SEQUENCE: 72

```
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg gctttcatac attagtagtc gtagtagtac catatactac     180
gcagactctg tgaagggccg attcaccatc tccagagaca atgccaagaa ctcactgtat     240
ctgcaaatga acagcctgag agacgaggac acggctgtgt attactgtgc gagagagcga     300
actggaacta cgaggtatta ctactactac tacggtatgg acgtctgggg ccaagggacc     360
acggtcaccg tctcctca                                                   378
```

<210> SEQ ID NO 73
<211> LENGTH: 126
<212> TYPE: PRT
<213> ORGANISM: Homo sapiens

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Leu
        35                  40                  45

Ser Tyr Ile Ser Ser Arg Ser Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Arg Thr Gly Thr Thr Arg Tyr Tyr Tyr Tyr Tyr Gly
            100                 105                 110

Met Asp Val Trp Gly Gln Gly Thr Thr Val Thr Val Ser Ser
```

<210> SEQ ID NO 74
<211> LENGTH: 321
<212> TYPE: DNA
<213> ORGANISM: Homo sapiens

<400> SEQUENCE: 74

```
gacatccaga tgacccagtc tccatcttcc gtgtctgcat ctgtaggaga cagagtcacc      60
atcacttgtc gggcgagtca gggtattagc agctggttag cctggtctca gcagaaacca     120
gggaaagccc ctaaactcct gatctatgct gcatccagtt tgcaaagtgg ggtcccatca     180
cggttcagcg gcagtggatc tgggacagat ttcactctca ccatcagcag cctgcagcct     240
gaagattttg caacttacta ttgtcaacag gctaacagtt tccctcggac gttcggccaa     300
gggaccaagg tggaaatcaa a                                               321
```

<210> SEQ ID NO 75
<211> LENGTH: 107
<212> TYPE: PRT
<213> ORGANISM: Homo sapiens

<400> SEQUENCE: 75

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Ser Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 76
<211> LENGTH: 11
<212> TYPE: PRT
<213> ORGANISM: Homo sapiens

<400> SEQUENCE: 76

Arg Ala Ser Gln Gly Ile Ser Ser Trp Leu Ala
1               5                   10

<210> SEQ ID NO 77
<211> LENGTH: 7
<212> TYPE: PRT
<213> ORGANISM: Homo sapiens

<400> SEQUENCE: 77

Ala Ala Ser Ser Leu Gln Ser
1               5

<210> SEQ ID NO 78
<211> LENGTH: 9
<212> TYPE: PRT
<213> ORGANISM: Homo sapiens

<400> SEQUENCE: 78

```
Gln Gln Ala Asn Ser Phe Pro Arg Thr
1               5
```

<210> SEQ ID NO 79
<211> LENGTH: 5
<212> TYPE: PRT
<213> ORGANISM: Homo sapiens

<400> SEQUENCE: 79

```
Ser Tyr Ser Met Asn
1               5
```

<210> SEQ ID NO 80
<211> LENGTH: 17
<212> TYPE: PRT
<213> ORGANISM: Homo sapiens

<400> SEQUENCE: 80

```
Tyr Ile Ser Ser Arg Ser Ser Thr Ile Tyr Tyr Ala Asp Ser Val Lys
1               5                   10                  15

Gly
```

<210> SEQ ID NO 81
<211> LENGTH: 17
<212> TYPE: PRT
<213> ORGANISM: Homo sapiens

<400> SEQUENCE: 81

```
Glu Arg Thr Gly Thr Thr Arg Tyr Tyr Tyr Tyr Tyr Gly Met Asp
1               5                   10                  15

Val
```

<210> SEQ ID NO 82
<211> LENGTH: 360
<212> TYPE: DNA
<213> ORGANISM: Homo sapiens

<400> SEQUENCE: 82

```
caggtgcagc tgcaggagtc gggcccagga ctggtgaagc cttcgaaaac cctgtccctc      60
acctgcactg tctctggtgg ctccatcagt agttactact ggagctggat ccggcagccc     120
gccgggaagg gactggagtg gattgggcgt atctatacca gtggaagcac caacctcaac     180
ccctccctca agagtcgagt caccatgtca atagacacgt ccaagagcca gttctccctg     240
aagttgagtt ctgtgaccgc cgcggacacg gccgtgtatt actgtgcgag actggaacta     300
cggaactact actacggtat ggacgtctgg ggccaaggga ccacggtcac cgtctcctca     360
```

<210> SEQ ID NO 83
<211> LENGTH: 120
<212> TYPE: PRT
<213> ORGANISM: Homo sapiens

<400> SEQUENCE: 83

```
Gln Val Gln Leu Gln Glu Ser Gly Pro Gly Leu Val Lys Pro Ser Lys
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Leu Asn Pro Ser Leu Lys
    50                  55                  60
```

Ser Arg Val Thr Met Ser Ile Asp Thr Ser Lys Ser Gln Phe Ser Leu
65                  70                  75                  80

Lys Leu Ser Ser Val Thr Ala Ala Asp Thr Ala Val Tyr Tyr Cys Ala
            85                  90                  95

Arg Leu Glu Leu Arg Asn Tyr Tyr Gly Met Asp Val Trp Gly Gln
            100                 105                 110

Gly Thr Thr Val Thr Val Ser Ser
        115                 120

<210> SEQ ID NO 84
<211> LENGTH: 330
<212> TYPE: DNA
<213> ORGANISM: Homo sapiens

<400> SEQUENCE: 84
cagtctgtgc tgactcagcc accctcagcg tctgggaccc ccgggcagag ggtcaccctc      60
tcttgttctg gaagcagttc caacatcgga agtaattatg tatactggta ccagcagctc     120
ccaggaaagg cccccaaact cctcatctat aggaataatc agcggccctc agggtccct      180 gaccgattct ctggctccaa gtctggcacc tcagcctccc tggccatcag tgggctccgg     240
tccgaggatg aggctgatta ttactgtgca gcatgggatg acagcctgag tggtcgggta     300
ttcggcggag ggaccaagct gaccgtccta                                       330

<210> SEQ ID NO 85
<211> LENGTH: 110
<212> TYPE: PRT
<213> ORGANISM: Homo sapiens

<400> SEQUENCE: 85

Gln Ser Val Leu Thr Gln Pro Pro Ser Ala Ser Gly Thr Pro Gly Gln
1               5                   10                  15

Arg Val Thr Leu Ser Cys Ser Gly Ser Ser Ser Asn Ile Gly Ser Asn
            20                  25                  30

Tyr Val Tyr Trp Tyr Gln Gln Leu Pro Gly Lys Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
            85                  90                  95

Ser Gly Arg Val Phe Gly Gly Gly Thr Lys Leu Thr Val Leu
            100                 105                 110

<210> SEQ ID NO 86
<211> LENGTH: 13
<212> TYPE: PRT
<213> ORGANISM: Homo sapiens

<400> SEQUENCE: 86

Ser Gly Ser Ser Ser Asn Ile Gly Ser Asn Tyr Val Tyr
1               5                   10

<210> SEQ ID NO 87
<211> LENGTH: 7
<212> TYPE: PRT
<213> ORGANISM: Homo sapiens

<400> SEQUENCE: 87

-continued

Arg Asn Asn Gln Arg Pro Ser
1               5

<210> SEQ ID NO 88
<211> LENGTH: 11
<212> TYPE: PRT
<213> ORGANISM: Homo sapiens

<400> SEQUENCE: 88

Ala Ala Trp Asp Asp Ser Leu Ser Gly Arg Val
1               5                   10

<210> SEQ ID NO 89
<211> LENGTH: 5
<212> TYPE: PRT
<213> ORGANISM: Homo sapiens

<400> SEQUENCE: 89

Ser Tyr Tyr Trp Ser
1               5

<210> SEQ ID NO 90
<211> LENGTH: 16
<212> TYPE: PRT
<213> ORGANISM: Homo sapiens

<400> SEQUENCE: 90

Arg Ile Tyr Thr Ser Gly Ser Thr Asn Leu Asn Pro Ser Leu Lys Ser
1               5                   10                  15

<210> SEQ ID NO 91
<211> LENGTH: 12
<212> TYPE: PRT
<213> ORGANISM: Homo sapiens

<400> SEQUENCE: 91

Leu Glu Leu Arg Asn Tyr Tyr Tyr Gly Met Asp Val
1               5                   10

<210> SEQ ID NO 92
<211> LENGTH: 378
<212> TYPE: DNA
<213> ORGANISM: Homo sapiens

<400> SEQUENCE: 92
caggtgcagc tggtggagtc tgggggaggc gtggtccagc ctggggaggtc cctgagactc      60
tcctgtgcag cgtctggatt caccttcagt agctatggca tgcactgggt ccgccaggct     120
ccaggcaagg gctggagtg gtggcagtt atatggtatg atggaagtaa taaatactat     180
gcagactccg tgaagggccg attcaccatc tccagagaca tttccaagaa cacgctgtat     240
ctgcaaatga acagcctgag agccgaggac acggctgtgt attactgtgc gaggagcggc     300
cccccccttgt atagtgggat ctactactac tacggtatgg acgtctgggg ccaagggacc     360
acggtcaccg tctcctca                                                    378

<210> SEQ ID NO 93
<211> LENGTH: 126
<212> TYPE: PRT
<213> ORGANISM: Homo sapiens

<400> SEQUENCE: 93

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
         20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Ile Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Gly Pro Pro Leu Tyr Ser Gly Ile Tyr Tyr Tyr Tyr Gly
                100                 105                 110

Met Asp Val Trp Gly Gln Gly Thr Thr Val Thr Val Ser Ser
                115                 120                 125

<210> SEQ ID NO 94
<211> LENGTH: 324
<212> TYPE: DNA
<213> ORGANISM: Homo sapiens

<400> SEQUENCE: 94
tcttctgagc tgactcagga ccctgctgtg tctgtggcct tgggacagac agtcaggatc    60
acatgccaag gagacagcct cagagcctat tatgcacact ggtaccagca gaagccagga   120
caggcccctg tgcttgtcat ctatggtaaa acaaccggcc ctcagggat cccagaccga   180 ttctctggct ccaactcagg aaacacagct tccttgacca tcactggggc tcaggcggaa   240
gatgaggctg actattactg taactcccgg gacagcagtg gtaaccatgt ggtattcggc   300
ggagggacca aactgaccgt ccta                                          324

<210> SEQ ID NO 95
<211> LENGTH: 108
<212> TYPE: PRT
<213> ORGANISM: Homo sapiens

<400> SEQUENCE: 95

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ala Tyr Tyr Ala
                 20                  25                  30

His Trp Tyr Gln Gln Lys Pro Gly Gln Ala Pro Val Leu Val Ile Tyr
                 35                  40                  45

Gly Lys Asn Asn Arg Pro Ser Gly Ile Pro Asp Arg Phe Ser Gly Ser
 50                  55                  60

Asn Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
                100                 105

<210> SEQ ID NO 96
<211> LENGTH: 11
<212> TYPE: PRT
<213> ORGANISM: Homo sapiens

<400> SEQUENCE: 96

Gln Gly Asp Ser Leu Arg Ala Tyr Tyr Ala His
```

<210> SEQ ID NO 97
<211> LENGTH: 7
<212> TYPE: PRT
<213> ORGANISM: Homo sapiens

<400> SEQUENCE: 97

Gly Lys Asn Asn Arg Pro Ser
1               5

<210> SEQ ID NO 98
<211> LENGTH: 11
<212> TYPE: PRT
<213> ORGANISM: Homo sapiens

<400> SEQUENCE: 98

Asn Ser Arg Asp Ser Ser Gly Asn His Val Val
1               5                   10

<210> SEQ ID NO 99
<211> LENGTH: 5
<212> TYPE: PRT
<213> ORGANISM: Homo sapiens

<400> SEQUENCE: 99

Ser Tyr Gly Met His
1               5

<210> SEQ ID NO 100
<211> LENGTH: 17
<212> TYPE: PRT
<213> ORGANISM: Homo sapiens

<400> SEQUENCE: 100

Val Ile Trp Tyr Asp Gly Ser Asn Lys Tyr Tyr Ala Asp Ser Val Lys
1               5                   10                  15

Gly

<210> SEQ ID NO 101
<211> LENGTH: 17
<212> TYPE: PRT
<213> ORGANISM: Homo sapiens

<400> SEQUENCE: 101

Ser Gly Pro Pro Leu Tyr Ser Gly Ile Tyr Tyr Tyr Tyr Gly Met Asp
1               5                   10                  15

Val

<210> SEQ ID NO 102
<211> LENGTH: 366
<212> TYPE: DNA
<213> ORGANISM: Homo sapiens

<400> SEQUENCE: 102
cagctgcagc tgcaggagtc gggcccagga ctggtgaagc cttcggagac cctgtccctc      60
acctgcactg tctctggtgg ctccatcagc agtagtcgtt actactgggg ctggatccgc     120
cagcccccag ggaaggggct ggagtggatt gggagtatct cttatcgtgg aaacacctac     180
tactacccgt ccctcaagag tcgagtcacc atatccgtag acacgtccaa gaaccagttt     240
tccctgaagc tgaactctgt gaccgccgca gacacggctg tgtattactg tgcgagacgg     300
acgtatagca gtggctggtc ttactttgac tactggggcc agggaaccct ggtcaccgtc     360
tcctca 366

<210> SEQ ID NO 103
<211> LENGTH: 122
<212> TYPE: PRT
<213> ORGANISM: Homo sapiens

<400> SEQUENCE: 103

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Ile Ser Tyr Arg Gly Asn Thr Tyr Tyr Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Arg Thr Tyr Ser Ser Gly Trp Ser Tyr Phe Asp Tyr Trp
            100                 105                 110

Gly Gln Gly Thr Leu Val Thr Val Ser Ser
        115                 120

<210> SEQ ID NO 104
<211> LENGTH: 324
<212> TYPE: DNA
<213> ORGANISM: Homo sapiens

<400> SEQUENCE: 104
tcctatgagc tgactcagcc atactcaatg tcagtggcca cagcacagat ggccaggatc      60
acctgtgggg gaaacaacat tggaagtaaa gctgtgcact ggtaccagca aaagccaggc     120
caggaccctg tgctggtcat ctatagcgat agcaaccggc cctcagggat ccctgagcga     180
ttctctggct ccaacccagg gaacaccgcc accctaacca tcagcaggat cgaggctggg     240
gatgaggcta attattactg tcaggtgtgg gacagtagta gtgatcattg ggtgttcggc     300
ggagggacca agctgaccgt ccta                                            324

<210> SEQ ID NO 105
<211> LENGTH: 108
<212> TYPE: PRT
<213> ORGANISM: Homo sapiens

<400> SEQUENCE: 105

Ser Tyr Glu Leu Thr Gln Pro Tyr Ser Met Ser Val Ala Thr Ala Gln
1               5                   10                  15

Met Ala Arg Ile Thr Cys Gly Gly Asn Asn Ile Gly Ser Lys Ala Val
            20                  25                  30

His Trp Tyr Gln Gln Lys Pro Gly Gln Asp Pro Val Leu Val Ile Tyr
        35                  40                  45

Ser Asp Ser Asn Arg Pro Ser Gly Ile Pro Glu Arg Phe Ser Gly Ser
    50                  55                  60

Asn Pro Gly Asn Thr Ala Thr Leu Thr Ile Ser Arg Ile Glu Ala Gly
65                  70                  75                  80

Asp Glu Ala Asn Tyr Tyr Cys Gln Val Trp Asp Ser Ser Ser Asp His
                85                  90                  95

```
Trp Val Phe Gly Gly Gly Thr Lys Leu Thr Val Leu
            100                 105
```

<210> SEQ ID NO 106
<211> LENGTH: 11
<212> TYPE: PRT
<213> ORGANISM: Homo sapiens

<400> SEQUENCE: 106

```
Gly Gly Asn Asn Ile Gly Ser Lys Ala Val His
1               5                   10
```

<210> SEQ ID NO 107
<211> LENGTH: 7
<212> TYPE: PRT
<213> ORGANISM: Homo sapiens

<400> SEQUENCE: 107

```
Ser Asp Ser Asn Arg Pro Ser
1               5
```

<210> SEQ ID NO 108
<211> LENGTH: 11
<212> TYPE: PRT
<213> ORGANISM: Homo sapiens

<400> SEQUENCE: 108

```
Gln Val Trp Asp Ser Ser Ser Asp His Trp Val
1               5                   10
```

<210> SEQ ID NO 109
<211> LENGTH: 7
<212> TYPE: PRT
<213> ORGANISM: Homo sapiens

<400> SEQUENCE: 109

```
Ser Ser Arg Tyr Tyr Trp Gly
1               5
```

<210> SEQ ID NO 110
<211> LENGTH: 16
<212> TYPE: PRT
<213> ORGANISM: Homo sapiens

<400> SEQUENCE: 110

```
Ser Ile Ser Tyr Arg Gly Asn Thr Tyr Tyr Tyr Pro Ser Leu Lys Ser
1               5                   10                  15
```

<210> SEQ ID NO 111
<211> LENGTH: 12
<212> TYPE: PRT
<213> ORGANISM: Homo sapiens

<400> SEQUENCE: 111

```
Arg Thr Tyr Ser Ser Gly Trp Ser Tyr Phe Asp Tyr
1               5                   10
```

<210> SEQ ID NO 112
<211> LENGTH: 357
<212> TYPE: DNA
<213> ORGANISM: Homo sapiens

<400> SEQUENCE: 112

```
gaggtgcagc tggtggagtc tgggggaggc ttggtaaagc ctggggggtc ccttagactc      60
```

```
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag cgtgtatta ctgttccact     300 gggtatagca gtggctgggt ccctggggc agggaaccc tggtcacggt ctcctca         357
```

```
<210> SEQ ID NO 113
<211> LENGTH: 119
<212> TYPE: PRT
<213> ORGANISM: Homo sapiens

<400> SEQUENCE: 113
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ser Thr Gly Tyr Ser Ser Gly Trp Val Pro Trp Gly Gln Gly
            100                 105                 110

Thr Leu Val Thr Val Ser Ser
        115

```
<210> SEQ ID NO 114
<211> LENGTH: 330
<212> TYPE: DNA
<213> ORGANISM: Homo sapiens

<400> SEQUENCE: 114
cagtctgtgt tgacgcagcc gccctcagtg tctgcggccc caggacagaa ggtcaccatc    60
tcctgctctg gaagcagctc aacattggga ataattatg tattctggta ccagcagctc    120
ccaggaacag cccccaaaact cctcatttat gacaataata gcgaccctc agggattcct    180 gaccgattct ctggctccaa gtctggcacg tcagccaccc tggcatcac cggactccag    240 actggggacg aggccgatta ttactgcgga acatgggata gcagcctgag tgctggggtg    300
ttcggcggag ggaccaaggt gaccgcccta                                     330
```

```
<210> SEQ ID NO 115
<211> LENGTH: 110
<212> TYPE: PRT
<213> ORGANISM: Homo sapiens

<400> SEQUENCE: 115
```

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Phe Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser

```
                    50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Val Phe Gly Gly Gly Thr Lys Val Thr Ala Leu
            100                 105                 110

<210> SEQ ID NO 116
<211> LENGTH: 13
<212> TYPE: PRT
<213> ORGANISM: Homo sapiens

<400> SEQUENCE: 116

Ser Gly Ser Ser Ser Asn Ile Gly Asn Asn Tyr Val Phe
 1               5                  10

<210> SEQ ID NO 117
<211> LENGTH: 7
<212> TYPE: PRT
<213> ORGANISM: Homo sapiens

<400> SEQUENCE: 117

Asp Asn Asn Lys Arg Pro Ser
 1               5

<210> SEQ ID NO 118
<211> LENGTH: 11
<212> TYPE: PRT
<213> ORGANISM: Homo sapiens

<400> SEQUENCE: 118

Gly Thr Trp Asp Ser Ser Leu Ser Ala Gly Val
 1               5                  10

<210> SEQ ID NO 119
<211> LENGTH: 5
<212> TYPE: PRT
<213> ORGANISM: Homo sapiens

<400> SEQUENCE: 119

Asn Ala Trp Met Ser
 1               5

<210> SEQ ID NO 120
<211> LENGTH: 19
<212> TYPE: PRT
<213> ORGANISM: Homo sapiens

<400> SEQUENCE: 120

Arg Ile Lys Ser Lys Thr Asp Gly Gly Thr Thr Asp Tyr Ala Ala Pro
 1               5                  10                  15

Val Lys Gly

<210> SEQ ID NO 121
<211> LENGTH: 8
<212> TYPE: PRT
<213> ORGANISM: Homo sapiens

<400> SEQUENCE: 121

Gly Tyr Ser Ser Gly Trp Val Pro
 1               5
```

```
<210> SEQ ID NO 122
<211> LENGTH: 378
<212> TYPE: DNA
<213> ORGANISM: Homo sapiens

<400> SEQUENCE: 122
gaggtgcagc tggtgcagtc tggagcagag gtgaaaaagc ccggggagtc tctgaagatc      60
tcctgtaaga gttctggata cagctttacc agctactgga tcggctgggt gcgccagatg     120
cccgggaaag gcctggagtg gatggggatc atctatcctg gtgactctgc aaccagatac     180
agcccgtcct tccaaggcca ggtcaccatc tcagccgaca gtccatcagc caccgcctac     240
ctgcagtgga gcagcctgaa ggcctcggac accgccatgt attactgtgc agacatgag      300 aagcagctgg tacgaaatat agctgtggct ggttcctttg actactgggg ccagggaacc     360
ctggtcaccg tctcctca                                                   378

<210> SEQ ID NO 123
<211> LENGTH: 126
<212> TYPE: PRT
<213> ORGANISM: Homo sapiens

<400> SEQUENCE: 123

Glu Val Gln Leu Val Gln Ser Gly Ala Glu Val Lys Lys Pro Gly Glu
1               5                   10                  15

Ser Leu Lys Ile Ser Cys Lys Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Ala Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Lys Gln Leu Val Arg Asn Ile Ala Val Ala Gly Ser
            100                 105                 110

Phe Asp Tyr Trp Gly Gln Gly Thr Leu Val Thr Val Ser Ser
        115                 120                 125

<210> SEQ ID NO 124
<211> LENGTH: 324
<212> TYPE: DNA
<213> ORGANISM: Homo sapiens

<400> SEQUENCE: 124
gaaattgtgt tgacgcagtc tccaggcacc ctgtctttgt ctccagggga aagagccacc      60
ctctcctgca gggccagtca gagtgttagc agcaagtact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagact ttgcagtgta ttactgtcag cagtattata gttcaccgct cactttcggc     300
ggagggacca aggtggagat caaa                                            324

<210> SEQ ID NO 125
<211> LENGTH: 108
<212> TYPE: PRT
<213> ORGANISM: Homo sapiens

<400> SEQUENCE: 125
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Lys
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Ser Ser Pro
                85                  90                  95

Leu Thr Phe Gly Gly Gly Thr Lys Val Glu Ile Lys
            100                 105
```

<210> SEQ ID NO 126
<211> LENGTH: 12
<212> TYPE: PRT
<213> ORGANISM: Homo sapiens

<400> SEQUENCE: 126

```
Arg Ala Ser Gln Ser Val Ser Ser Lys Tyr Leu Ala
1               5                   10
```

<210> SEQ ID NO 127
<211> LENGTH: 7
<212> TYPE: PRT
<213> ORGANISM: Homo sapiens

<400> SEQUENCE: 127

```
Gly Ala Ser Ser Arg Ala Thr
1               5
```

<210> SEQ ID NO 128
<211> LENGTH: 9
<212> TYPE: PRT
<213> ORGANISM: Homo sapiens

<400> SEQUENCE: 128

```
Gln Gln Tyr Tyr Ser Ser Pro Leu Thr
1               5
```

<210> SEQ ID NO 129
<211> LENGTH: 5
<212> TYPE: PRT
<213> ORGANISM: Homo sapiens

<400> SEQUENCE: 129

```
Ser Tyr Trp Ile Gly
1               5
```

<210> SEQ ID NO 130
<211> LENGTH: 17
<212> TYPE: PRT
<213> ORGANISM: Homo sapiens

<400> SEQUENCE: 130

```
Ile Ile Tyr Pro Gly Asp Ser Ala Thr Arg Tyr Ser Pro Ser Phe Gln
1               5                   10                  15

Gly
```

<210> SEQ ID NO 131
<211> LENGTH: 17
<212> TYPE: PRT
<213> ORGANISM: Homo sapiens

<400> SEQUENCE: 131

His Glu Lys Gln Leu Val Arg Asn Ile Ala Val Ala Gly Ser Phe Asp
1               5                   10                  15

Tyr

<210> SEQ ID NO 132
<211> LENGTH: 717
<212> TYPE: DNA
<213> ORGANISM: Homo sapiens

<400> SEQUENCE: 132

```
atgaggctcc ctgctcagct cctggggctg ctaatgctct gggtccctgg atccagtggg      60
gatattgtga tgacccagac tccactctcc tcacctgtca cccttggaca gccggcctcc     120
atctcctgca ggtctagtca agcctcgta cacagtgatg aaacaccta cttgagttgg       180
cttcagcaga ggccaggcca gcctccaaga ctcctaattt ataagatttc taaccggttc     240
tctggggtcc cagacagatt cagtggcagt ggggcaggga cagatttcac actgaaaatc     300
agcagggtgg aagctgagga tgtcggggtt tactactgca tgcaaattac acaatttcct    360
ctcactttcg gcggagggac caaggtggag atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt        717
```

<210> SEQ ID NO 133
<211> LENGTH: 239
<212> TYPE: PRT
<213> ORGANISM: Homo sapiens

<400> SEQUENCE: 133

Met Arg Leu Pro Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
                20                  25                  30

Val Thr Leu Gly Gln Pro Ala Ser Ile Ser Cys Arg Ser Ser Gln Ser
            35                  40                  45

Leu Val His Ser Asp Gly Asn Thr Tyr Leu Ser Trp Leu Gln Gln Arg
        50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Ile Thr Gln Phe Pro Leu Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu

```
145                 150                 155                 160
Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 134
<211> LENGTH: 1404
<212> TYPE: DNA
<213> ORGANISM: Homo sapiens

<400> SEQUENCE: 134
atggacacac tttgctacac actcctgctg ctgaccaccc cttcctgggt cttgtcccag      60
gtcaccttga aggagtctgg tcctgtgctg gtgaaaccca cagagaccct cacgctgacc     120
tgcaccgtct ctgggttctc actcagcaat gctagaatga gtgtgagctg gatccgtcag     180
cccccaggga aggccctgga gtggcttgca cacattttt cgaatgacga aaatcctac      240 agcacatctc tgaagagcag gctcaccatc tccaaggaca cctccaaaag ccaggtggtc     300
cttaccatga ccaacatgga ccctgtggac acagccacat attactgtgc acggatccgg     360
ggtacggtgg gttatgacta ctggggccag ggaaccctgg tcaccgtctc ctcagcctcc     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcaccca gacctacatc      660 tgcaacgtga atcacaagcc cagcaacacc aaggtggaca gagagttga gcccaaatct      720 tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctatagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                           1404

<210> SEQ ID NO 135
<211> LENGTH: 468
<212> TYPE: PRT
<213> ORGANISM: Homo sapiens

<400> SEQUENCE: 135
```

-continued

```
Met Asp Thr Leu Cys Tyr Thr Leu Leu Leu Thr Thr Pro Ser Trp
1               5                   10                  15

Val Leu Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Ser Asn Ala Arg Met Ser Val Ser Trp Ile Arg Gln Pro Pro Gly Lys
    50                  55                  60

Ala Leu Glu Trp Leu Ala His Ile Phe Ser Asn Asp Glu Lys Ser Tyr
65                  70                  75                  80

Ser Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
            100                 105                 110

Thr Tyr Tyr Cys Ala Arg Ile Arg Gly Thr Val Gly Tyr Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
```

```
                420            425            430
Val Asp Lys Ser Arg Trp Gln Gln Gly Asn Val Phe Ser Cys Ser Val
            435                440                445
Met His Glu Ala Leu His Asn His Tyr Thr Gln Lys Ser Leu Ser Leu
            450                455                460
Ser Pro Gly Lys
465

<210> SEQ ID NO 136
<211> LENGTH: 717
<212> TYPE: DNA
<213> ORGANISM: Homo sapiens

<400> SEQUENCE: 136
atgaggctcc ctgctcagct cctggggctg ctaatgctct gggtccctgg atccagtggg      60
gatattgtga tgacccagac tccactctcc tcacctgtca cccttggaca gccggcctcc     120
atctcctgca ggtctagtca aagcctcgta cacagtgatg gaaacaccta cttgaattgg     180
cttcagcaga ggccaggcca gcctccaaga ctcctaattt ataagatttc taaccggttc     240
tctggggtcc cagacagatt cactggcagt ggggcaggga cagatttcac actgaaaatc     300
agcagggtgg aagctgagga tgtcggggtt tatacctgca tgcaagttac acaatttcct     360
ctcaccttcg gccaagggac acgactggag attaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt       717

<210> SEQ ID NO 137
<211> LENGTH: 239
<212> TYPE: PRT
<213> ORGANISM: Homo sapiens

<400> SEQUENCE: 137

Met Arg Leu Pro Ala Gln Leu Leu Gly Leu Leu Met Leu Trp Val Pro
1               5                  10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Thr Gly Ser Gly Ala Gly Thr Asp Phe
                85                  90                  95

Thr Leu Lys Ile Ser Arg Val Glu Ala Glu Asp Val Gly Val Tyr Thr
            100                 105                 110

Cys Met Gln Val Thr Gln Phe Pro Leu Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160
```

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 138
<211> LENGTH: 1410
<212> TYPE: DNA
<213> ORGANISM: Homo sapiens

<400> SEQUENCE: 138

```
atggacacac tttgctacac actcctgctg ctgaccaccc cttcctgggt cttgtcccag      60
gtcaccttga aggagtctgg tcctgtgctg ctgaaaccca cagagaccct cacgctgacc     120
tgcaccgtct ctgggttctc actcagcaat gctagaatgg gtgtgagctg gatccgtcag     180
cccccaggga aggccctgga gtggcttgca cacattttttt cgaatgacga aaaatcctac    240
atcacatctc tgaagagcag gctcaccatc tccaaggaca cctccaaaag ccaggtggtc     300
cttaccatga ccaacatgga ccctgtggac acagccacat attactgtgc acggataccc     360
ctacgatccc cgggtgcttt tgatatctgg ggccaaggga caatggtcac cgtctcttca     420
gcctccacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccgtgcccag cacctgaact cctggggggga    780
ccgtcagtct tcctcttccc cccaaaaccc aaggacaccc tcatgatctc ccggaccect     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gcagccccg agaaccacag gtgtacaccc tgcccccatc ccgggaggag     1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcaggggga acgtcttctc atgctccgtg atgcatgagg ctctgcacaa ccactacacg    1380
cagaagagcc tctcactgtc tccgggtaaa                                     1410
```

<210> SEQ ID NO 139
<211> LENGTH: 470
<212> TYPE: PRT
<213> ORGANISM: Homo sapiens

<400> SEQUENCE: 139

```
Met Asp Thr Leu Cys Tyr Thr Leu Leu Leu Thr Thr Pro Ser Trp
1               5                   10                  15

Val Leu Ser Gln Val Thr Leu Lys Glu Ser Gly Pro Val Leu Lys
            20                  25                  30

Pro Thr Glu Thr Leu Thr Leu Cys Thr Val Ser Gly Phe Ser Leu
            35                  40                  45

Ser Asn Ala Arg Met Gly Val Ser Trp Ile Arg Gln Pro Pro Gly Lys
50                  55                  60

Ala Leu Glu Trp Leu Ala His Ile Phe Ser Asn Asp Glu Lys Ser Tyr
65                  70                  75                  80

Ile Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
                100                 105                 110

Thr Tyr Tyr Cys Ala Arg Ile Pro Leu Arg Ser Pro Gly Ala Phe Asp
            115                 120                 125

Ile Trp Gly Gln Gly Thr Met Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430
```

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
        450                 455                 460

Ser Leu Ser Pro Gly Lys
465             470

<210> SEQ ID NO 140
<211> LENGTH: 717
<212> TYPE: DNA
<213> ORGANISM: Homo sapiens

<400> SEQUENCE: 140
atgaggctcc ctgctcagct cctggggctg ctaatgctct gggtccctgg atccagtggg      60
gaaattgtga tgacccagac tccactctcc tcacctgtca cccttggaca gccggcctcc     120
atctcctgca ggtctagtca aagcctcgta cacagtgatc gaaacaccta cttgagttgg     180
cttcagcaga ggccaggcca gcctccaaga ctcctcattt ataagatttc taaccgattc     240
tctggggtcc cagacagatt cagtggcagt ggggcaggga cagatttcac actgaaaatc     300
agcagggtgg aggctgagga tgtcggggtt tattactgca tgcaaactac acaacttcct     360
ctcactttcg gccaagggc acgactgag attaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt       717

<210> SEQ ID NO 141
<211> LENGTH: 239
<212> TYPE: PRT
<213> ORGANISM: Homo sapiens

<400> SEQUENCE: 141

Met Arg Leu Pro Ala Gln Leu Leu Gly Leu Leu Met Leu Trp Val Pro
1               5                   10                  15

Gly Ser Ser Gly Glu Ile Val Met Thr Gln Thr Pro Leu Ser Ser Pro
                20                  25                  30

Val Thr Leu Gly Gln Pro Ala Ser Ile Ser Cys Arg Ser Ser Gln Ser
        35                  40                  45

Leu Val His Ser Asp Arg Asn Thr Tyr Leu Ser Trp Leu Gln Gln Arg
    50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Thr Thr Gln Leu Pro Leu Thr Phe Gly Gln Gly Ala Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 142
<211> LENGTH: 1410
<212> TYPE: DNA
<213> ORGANISM: Homo sapiens

<400> SEQUENCE: 142

| atggacacac | tttgctacac | actcctgctg | ctgaccaccc | cttcctgggt | cttgtcccag | 60 |
| gtcaccttga | aggagtctgg | tcctgtgctg | gtgaaaccca | cagagaccct | cacgctgacc | 120 |
| tgcaccgtct | ctgggttctc | actcagcaat | gctagaatgg | gtgtgagctg | gatccgtcag | 180 |
| cccccaggga | aggccctgga | gtggcttgca | cacatttttt | cgaatgacga | aaaatcctac | 240 |
| agcacatctc | tgaagagcag | gctcaccatc | tccaaggaca | ccttcaaaag | ccaggtggtc | 300 |
| cttaccatga | ccaacatgga | ccctgtggac | acagccacat | attactgtgc | acggataccc | 360 |
| ctacgatccc | cggtgctttt | gatatctggg | gccaaggga | caatggtcac | cgtctcttca | 420 |
| gcctccacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagag | agttgagccc | 720 |
| aaatcttgtg | acaaaactca | cacatgccca | ccgtgcccag | cacctgaact | cctgggggga | 780 |
| ccgtcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cgcgggagga | gcagtacaac | 960 |
| agcacgtacc | gtgtggtcag | cgtcctcacc | gtcctgcacc | aggactggct | gaatggcaag | 1020 |
| gagtacaagt | gcaaggtctc | caacaaagcc | ctcccagccc | catcgagaa | aaccatctcc | 1080 |
| aaagccaaag | ggcagccccg | agaaccacag | gtgtacaccc | tgcccccatc | ccgggaggag | 1140 |
| atgaccaaga | accaggtcag | cctgacctgc | ctggtcaaag | gcttctatcc | cagcgacatc | 1200 |
| gccgtggagt | gggagagcaa | tgggcagccg | gagaacaact | acaagaccac | gcctcccgtg | 1260 |
| ctggactccg | acggctcctt | cttcctctat | agcaagctca | ccgtggacaa | gagcaggtgg | 1320 |
| cagcagggga | acgtcttctc | atgctccgtg | atgcatgagg | ctctgcacaa | ccactacacg | 1380 |
| cagaagagcc | tctccctgtc | tccgggtaaa | | | | 1410 |

<210> SEQ ID NO 143
<211> LENGTH: 470
<212> TYPE: PRT
<213> ORGANISM: Homo sapiens

<400> SEQUENCE: 143

Met Asp Thr Leu Cys Tyr Thr Leu Leu Leu Leu Thr Thr Pro Ser Trp

```
                1               5                   10                  15
            Val Leu Ser Gln Val Thr Leu Lys Glu Ser Gly Pro Val Leu Val Lys
                            20                  25                  30

Pro Thr Glu Thr Leu Thr Leu Thr Cys Thr Val Ser Gly Phe Ser Leu
                            35                  40                  45

Ser Asn Ala Arg Met Gly Val Ser Trp Ile Arg Gln Pro Pro Gly Lys
                            50                  55                  60

Ala Leu Glu Trp Leu Ala His Ile Phe Ser Asn Asp Glu Lys Ser Tyr
            65                  70                  75                  80

Ser Thr Ser Leu Lys Ser Arg Leu Thr Ile Ser Lys Asp Thr Phe Lys
                            85                  90                  95

Ser Gln Val Val Leu Thr Met Thr Asn Met Asp Pro Val Asp Thr Ala
                            100                 105                 110

Thr Tyr Tyr Cys Ala Arg Ile Pro Leu Arg Ser Pro Gly Ala Phe Asp
                            115                 120                 125

Ile Trp Gly Gln Gly Thr Met Val Thr Val Ser Ala Ser Thr Lys
                            130                 135                 140

Gly Pro Ser Val Phe Pro Leu Ala Pro Ser Ser Lys Ser Thr Ser Gly
            145                 150                 155                 160

Gly Thr Ala Ala Leu Gly Cys Leu Val Lys Asp Tyr Phe Pro Glu Pro
                            165                 170                 175

Val Thr Val Ser Trp Asn Ser Gly Ala Leu Thr Ser Gly Val His Thr
                            180                 185                 190

Phe Pro Ala Val Leu Gln Ser Ser Gly Leu Tyr Ser Leu Ser Ser Val
                            195                 200                 205

Val Thr Val Pro Ser Ser Ser Leu Gly Thr Gln Thr Tyr Ile Cys Asn
                            210                 215                 220

Val Asn His Lys Pro Ser Asn Thr Lys Val Asp Lys Arg Val Glu Pro
            225                 230                 235                 240

Lys Ser Cys Asp Lys Thr His Thr Cys Pro Pro Cys Pro Ala Pro Glu
                            245                 250                 255

Leu Leu Gly Gly Pro Ser Val Phe Leu Phe Pro Pro Lys Pro Lys Asp
                            260                 265                 270

Thr Leu Met Ile Ser Arg Thr Pro Glu Val Thr Cys Val Val Val Asp
                            275                 280                 285

Val Ser His Glu Asp Pro Glu Val Lys Phe Asn Trp Tyr Val Asp Gly
                            290                 295                 300

Val Glu Val His Asn Ala Lys Thr Lys Pro Arg Glu Glu Gln Tyr Asn
            305                 310                 315                 320

Ser Thr Tyr Arg Val Val Ser Val Leu Thr Val Leu His Gln Asp Trp
                            325                 330                 335

Leu Asn Gly Lys Glu Tyr Lys Cys Lys Val Ser Asn Lys Ala Leu Pro
                            340                 345                 350

Ala Pro Ile Glu Lys Thr Ile Ser Lys Ala Lys Gly Gln Pro Arg Glu
                            355                 360                 365

Pro Gln Val Tyr Thr Leu Pro Pro Ser Arg Glu Glu Met Thr Lys Asn
                            370                 375                 380

Gln Val Ser Leu Thr Cys Leu Val Lys Gly Phe Tyr Pro Ser Asp Ile
            385                 390                 395                 400

Ala Val Glu Trp Glu Ser Asn Gly Gln Pro Glu Asn Asn Tyr Lys Thr
                            405                 410                 415

Thr Pro Pro Val Leu Asp Ser Asp Gly Ser Phe Phe Leu Tyr Ser Lys
                            420                 425                 430
```

```
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 144
<211> LENGTH: 990
<212> TYPE: DNA
<213> ORGANISM: Homo sapiens

<400> SEQUENCE: 144
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccga gaaccacagg tgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 145
<211> LENGTH: 330
<212> TYPE: PRT
<213> ORGANISM: Homo sapiens

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 146
<211> LENGTH: 978
<212> TYPE: DNA
<213> ORGANISM: Homo sapiens

<400> SEQUENCE: 146
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
```

```
gtcttctcat gctccgtgat gcatgaggct ctgcacaacc actacacgca gaagagcctc    960
tccctgtctc cgggtaaa                                                  978
```

<210> SEQ ID NO 147
<211> LENGTH: 326
<212> TYPE: PRT
<213> ORGANISM: Homo sapiens

<400> SEQUENCE: 147

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 148
<211> LENGTH: 321
<212> TYPE: DNA
<213> ORGANISM: Homo sapiens -continued

<400> SEQUENCE: 148

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct caatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                              321
```

<210> SEQ ID NO 149
<211> LENGTH: 107
<212> TYPE: PRT
<213> ORGANISM: Homo sapiens

<400> SEQUENCE: 149

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 150
<211> LENGTH: 318
<212> TYPE: DNA
<213> ORGANISM: Homo sapiens

<400> SEQUENCE: 150

```
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag   240
tcccacagaa gctacagctg ccaggtcacg catgaaggga gcaccgtgga aaagacagtg   300
gcccctacag aatgttca                                                318
```

<210> SEQ ID NO 151
<211> LENGTH: 106
<212> TYPE: PRT
<213> ORGANISM: Homo sapiens

<400> SEQUENCE: 151

```
Gly Gln Pro Lys Ala Asn Pro Thr Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45
```

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 152
<211> LENGTH: 318
<212> TYPE: DNA
<213> ORGANISM: Homo sapiens

<400> SEQUENCE: 152
ggtcagccca aggctgcccc ctcggtcact ctgttcccgc cctcctctga ggagcttcaa        60
gccaacaagg ccacactggt gtgtctcata agtgacttct acccgggagc cgtgacagtg       120
gcctggaagg cagatagcag ccccgtcaag gcgggagtgg agaccaccac accctccaaa       180
caaagcaaca acaagtacgc ggccagcagc tatctgagcc tgacgcctga gcagtggaag       240
tcccacagaa gctacagctg ccaggtcacg catgaaggga gcaccgtgga aagacagtg        300 gcccctacag aatgttca                                                    318

<210> SEQ ID NO 153
<211> LENGTH: 106
<212> TYPE: PRT
<213> ORGANISM: Homo sapiens

<400> SEQUENCE: 153

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 154
<211> LENGTH: 318
<212> TYPE: DNA
<213> ORGANISM: Homo sapiens

<400> SEQUENCE: 154
ggtcagccca aggctgcccc ctcggtcact ctgttcccac cctcctctga ggagcttcaa        60
gccaacaagg ccacactggt gtgtctcata agtgacttct acccgggagc cgtgacagtg       120
gcctggaagg cagatagcag ccccgtcaag gcgggagtgg agaccaccac accctccaaa       180
caaagcaaca acaagtacgc ggccagcagc tacctgagcc tgacgcctga gcagtggaag       240
tcccacaaaa gctacagctg ccaggtcacg catgaaggga gcaccgtgga aagacagtg        300 gcccctacag aatgttca                                                       318

<210> SEQ ID NO 155
<211> LENGTH: 106
<212> TYPE: PRT
<213> ORGANISM: Homo sapiens

<400> SEQUENCE: 155

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 156
<211> LENGTH: 318
<212> TYPE: DNA
<213> ORGANISM: Homo sapiens

<400> SEQUENCE: 156
ggtcagccca aggctgcccc atcggtcact ctgttcccgc cctcctctga ggagcttcaa    60
gccaacaagg ccacactggt gtgcctgatc agtgacttct acccgggagc tgtgaaagtg   120
gcctggaagg cagatggcag ccccgtcaac acgggagtgg agaccaccac accctccaaa   180
cagagcaaca acaagtacgc ggccagcagc tacctgagcc tgacgcctga gcagtggaag   240
tcccacagaa gctacagctg ccaggtcacg catgaaggga gcaccgtgga agacagtg     300 gcccctgcag aatgtgca                                                  318

<210> SEQ ID NO 157
<211> LENGTH: 106
<212> TYPE: PRT
<213> ORGANISM: Homo sapiens

<400> SEQUENCE: 157

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ala
            100                 105

<210> SEQ ID NO 158
<211> LENGTH: 318
<212> TYPE: DNA
<213> ORGANISM: Homo sapiens

<400> SEQUENCE: 158

```
ggtcagccca aggctgcccc ctcggtcact ctgttccac cctcctctga ggagcttcaa    60
gccaacaagg ccacactggt gtgtctcgta agtgacttct acccgggagc cgtgacagtg   120
gcctggaagg cagatggcag ccccgtcaag gtgggagtgg agaccaccaa accctccaaa   180
caaagcaaca acaagtatgc ggccagcagc tacctgagcc tgacgcccga gcagtggaag   240
tcccacagaa gctacagctg ccgggtcacg catgaaggga gcaccgtgga aagacagtg    300
gcccctgcag aatgctct                                                 318
```

<210> SEQ ID NO 159
<211> LENGTH: 106
<212> TYPE: PRT
<213> ORGANISM: Homo sapiens

<400> SEQUENCE: 159

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 160
<211> LENGTH: 17
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: If the amino acid in position 4 is Ser, Xaa = any amino acid except Ser
<220> FEATURE:
<221> NAME/KEY: misc_feature
<222> LOCATION: (8)..(8)
<223> OTHER INFORMATION: If the amino acid in position 4 is Ser, Xaa = any amino acid except Ile

<400> SEQUENCE: 160

Tyr Ile Ser Xaa Xaa Ser Ser Xaa Ile Tyr Tyr Ala Asp Ser Val Lys
1               5                   10                  15

Gly

<210> SEQ ID NO 161
<211> LENGTH: 17
<212> TYPE: PRT

```
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 161

Glu Xaa Thr Xaa Thr Thr Arg Xaa Tyr Tyr Tyr Tyr Tyr Gly Xaa Asp
1               5                   10                  15

Val

<210> SEQ ID NO 162
<211> LENGTH: 12
<212> TYPE: PRT
<213> ORGANISM: Homo sapiens
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 162

Arg Ala Ser Gln Xaa Xaa Ser Ser Xaa Xaa Leu Ala
1               5                   10

<210> SEQ ID NO 163
<211> LENGTH: 336
<212> TYPE: DNA
<213> ORGANISM: Artificial sequence
<220> FEATURE:
<223> OTHER INFORMATION: Human/mouse chimera sequence

<400> SEQUENCE: 163
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                               336

<210> SEQ ID NO 164
<211> LENGTH: 112
<212> TYPE: PRT
<213> ORGANISM: Artificial sequence
<220> FEATURE:
<223> OTHER INFORMATION: Human/mouse chimera sequence

<400> SEQUENCE: 164

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
                   20                  25                  30
Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
             100                 105                 110

<210> SEQ ID NO 165
<211> LENGTH: 363
<212> TYPE: DNA
<213> ORGANISM: Artificial sequence
<220> FEATURE:
<223> OTHER INFORMATION: Human/mouse chimera sequence

<400> SEQUENCE: 165
caagttactc taaaagagtc tggccctggg atattgaagc cctcacagac cctcagtctg      60
acttgttctt tctctgggtt ttcactgaga acttctggta tgggtgtagg ctggattcgt     120
cagccttcag ggaagggtct ggagtggctg gcacacattt ggtgggatga tgataagtcc     180
tataacccat ccctgaagag ccagctcaca atctccaagg ataccctccag aaaccaggta    240 ttcctcaaga tcaccagtgt ggacactgca gatactgcca cttactactg tgctcgaagg     300
aactattatt acgacgacta ctttgcctac tggggccaag gcaccactct caccgtctct     360
agt                                                                   363

<210> SEQ ID NO 166
<211> LENGTH: 121
<212> TYPE: PRT
<213> ORGANISM: Artificial sequence
<220> FEATURE:
<223> OTHER INFORMATION: Human/mouse chimera sequence

<400> SEQUENCE: 166

Gln Val Thr Leu Lys Glu Ser Gly Pro Gly Ile Leu Lys Pro Ser Gln
 1               5                  10                  15

Thr Leu Ser Leu Thr Cys Ser Phe Ser Gly Phe Ser Leu Arg Thr Ser
             20                  25                  30

Gly Met Gly Val Gly Trp Ile Arg Gln Pro Ser Gly Lys Gly Leu Glu
         35                  40                  45

Trp Leu Ala His Ile Trp Trp Asp Asp Asp Lys Ser Tyr Asn Pro Ser
     50                  55                  60

Leu Lys Ser Gln Leu Thr Ile Ser Lys Asp Thr Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Arg Asn Tyr Tyr Tyr Asp Asp Tyr Phe Ala Tyr Trp Gly
             100                 105                 110

Gln Gly Thr Thr Leu Thr Val Ser Ser
         115                 120

<210> SEQ ID NO 167
<211> LENGTH: 714
<212> TYPE: DNA
<213> ORGANISM: Artificial sequence
```

```
<220> FEATURE:
<223> OTHER INFORMATION: Human/mouse chimera sequence

<400> SEQUENCE: 167
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca aagtttccaa ccgattttct     240
ggggtcccag acaggttcag tggcagtgga tcaggacag atttcacact caagatcagc      300
agagtggagg ctgaggatct gggagtttat tactgctttc aaggttcaca tgttccgctc     360
acgttcggtg ctgggaccaa gctggagctg aaacggactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660
acccatcagg gcctgagctc gcccgtcaca aagagcttca caggggaga gtgt              714

<210> SEQ ID NO 168
<211> LENGTH: 238
<212> TYPE: PRT
<213> ORGANISM: Artificial sequence
<220> FEATURE:
<223> OTHER INFORMATION: Human/mouse chimera sequence

<400> SEQUENCE: 168

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Leu Thr Phe Gly Ala Gly Thr Lys Leu
            115                 120                 125

Glu Leu Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205
```

Asp Tyr Glu Lys His Lys Val Tyr Ala Cys Glu Val Thr His Gln Gly
 210                 215                 220

Leu Ser Ser Pro Val Thr Lys Ser Phe Asn Arg Gly Glu Cys
225                 230                 235

<210> SEQ ID NO 169
<211> LENGTH: 1410
<212> TYPE: DNA
<213> ORGANISM: Artificial sequence
<220> FEATURE:
<223> OTHER INFORMATION: Human/mouse chimera sequence

<400> SEQUENCE: 169

```
atggacaggc ttacttcctc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagaact tctggtatgg gtgtaggctg gattcgtcag     180
ccttcaggga agggtctgga gtggctggca cacatttggt gggatgatga taagtcctat     240
aacccatccc tgaagagcca gctcacaatc tccaaggata cctccagaaa ccaggtattc     300
ctcaagatca ccagtgtgga cactgcagat actgccactt actactgtgc tcgaaggaac     360
tattattacg acgactactt tgcctactgg ggccaaggca ccactctcac cgtctctagt     420
gcctccacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cgcgggagga gcagtacaac     960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa                                     1410
```

<210> SEQ ID NO 170
<211> LENGTH: 470
<212> TYPE: PRT
<213> ORGANISM: Artificial sequence
<220> FEATURE:
<223> OTHER INFORMATION: Human/mouse chimera sequence

<400> SEQUENCE: 170

Met Asp Arg Leu Thr Ser Ser Phe Leu Leu Leu Ile Val Pro Ala Tyr
1               5                   10                  15

```
Val Leu Ser Gln Val Thr Leu Lys Glu Ser Gly Pro Gly Ile Leu Lys
             20                  25                  30

Pro Ser Gln Thr Leu Ser Leu Thr Cys Ser Phe Ser Gly Phe Ser Leu
         35                  40                  45

Arg Thr Ser Gly Met Gly Val Gly Trp Ile Arg Gln Pro Ser Gly Lys
 50                  55                  60

Gly Leu Glu Trp Leu Ala His Ile Trp Trp Asp Asp Lys Ser Tyr
 65                  70                  75                  80

Asn Pro Ser Leu Lys Ser Gln Leu Thr Ile Ser Lys Asp Thr Ser Arg
                 85                  90                  95

Asn Gln Val Phe Leu Lys Ile Thr Ser Val Asp Thr Ala Asp Thr Ala
                100                 105                 110

Thr Tyr Tyr Cys Ala Arg Arg Asn Tyr Tyr Asp Asp Tyr Phe Ala
         115                 120                 125

Tyr Trp Gly Gln Gly Thr Thr Leu Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
        435                 440                 445
```

```
Ser Val Met His Glu Ala Leu His Asn His Tyr Thr Gln Lys Ser Leu
    450                 455                 460

Ser Leu Ser Pro Gly Lys
465                 470
```